United States Patent
Labib et al.

(10) Patent No.: US 9,751,049 B2
(45) Date of Patent: Sep. 5, 2017

(54) COMPOSITIONS AND METHODS OF CLEANING POLYVINYL PYRROLIDONE-BASED HEMODIALYSIS FILTRATION MEMBRANE ASSEMBLIES

(71) Applicant: Princeton Trade and Technology, Inc., Princeton, NJ (US)

(72) Inventors: Mohamed Emam Labib, Princeton, NJ (US); Yacoob Tabani, Basking Ridge, NJ (US)

(73) Assignee: Novaflux Inc., Princeton, NJ (US)

(*) Notice: Subject to any disclaimer, the term of this patent is extended or adjusted under 35 U.S.C. 154(b) by 0 days.

(21) Appl. No.: 14/623,230

(22) Filed: Feb. 16, 2015

(65) Prior Publication Data

US 2015/0343386 A1 Dec. 3, 2015

Related U.S. Application Data

(60) Provisional application No. 62/005,365, filed on May 30, 2014.

(51) Int. Cl.
*B01D 65/06* (2006.01)
*C11D 7/06* (2006.01)
(Continued)

(52) U.S. Cl.
CPC ............... *B01D 65/06* (2013.01); *A61L 2/00* (2013.01); *A61L 9/00* (2013.01); *B01D 65/02* (2013.01);
(Continued)

(58) Field of Classification Search
CPC ..... A61M 1/1682; A61M 1/169; B01D 61/30; B01D 65/02; B01D 65/022; B01D 65/06;
(Continued)

(56) References Cited

U.S. PATENT DOCUMENTS 4,789,467 A * 12/1988 Lindsay ............... A61M 1/169
210/103
4,878,951 A 11/1989 Pochard et al.
(Continued)

OTHER PUBLICATIONS

Spahl, Richard James, "FCE: Groundbreaking Measurement of Free Chlorine Disinfecting Power in a Handheld Instrucment," 2012, Myron L Company, 12 pages.*
(Continued)

*Primary Examiner* — Bobby Ramdhanie
*Assistant Examiner* — Patrick Orme
(74) *Attorney, Agent, or Firm* — Posz Law Group, PLC

(57) ABSTRACT

A method and a composition of cleaning and reprocessing a hemodialysis filtration membrane assembly that employs polyvinylpyrrolidone-containing membranes, the method comprising the step of treating the assembly with an aqueous mixture or a gas-liquid mixture comprising an inorganic base and from 100 to 1,000 ppm of a hypochlorite salt, wherein the mixture has a pH between about 12.0 and about 12.5, an oxidation reduction potential of less than 0.5 volts, a temperature of 40° to 55° C. and wherein the mole % of hypochlorous acid, HOCl, relative to the sum of hypochlorous acid plus hypochlorite anion, —OCl, is less than 0.004%.

19 Claims, 13 Drawing Sheets

(51) Int. Cl.
| | |
|---|---|
| C11D 7/10 | (2006.01) |
| C11D 7/16 | (2006.01) |
| B01D 65/02 | (2006.01) |
| C11D 3/395 | (2006.01) |
| C11D 3/48 | (2006.01) |
| A61L 2/00 | (2006.01) |
| A61L 9/00 | (2006.01) |
| B01D 63/02 | (2006.01) |
| B01D 71/68 | (2006.01) |

(52) U.S. Cl.
CPC ............ *C11D 3/3956* (2013.01); *C11D 3/48* (2013.01); *C11D 7/06* (2013.01); *C11D 7/10* (2013.01); *C11D 7/16* (2013.01); *B01D 63/02* (2013.01); *B01D 71/68* (2013.01); *B01D 2321/04* (2013.01); *B01D 2321/08* (2013.01); *B01D 2321/162* (2013.01); *B01D 2321/164* (2013.01); *B01D 2321/168* (2013.01); *B01D 2321/18* (2013.01)

(58) Field of Classification Search
CPC ........ B01D 65/22; B01D 71/06; B01D 71/68; B01D 2321/04; B01D 2321/164; B01D 2321/168; B01D 2321/18; B01D 2321/185; B08B 2209/022
See application file for complete search history.

(56) References Cited

U.S. PATENT DOCUMENTS

| | | | |
|---|---|---|---|
| 5,139,675 | A | 8/1992 | Arnold et al. |
| 6,379,617 | B1 | 4/2002 | Spickermann |
| 6,655,394 | B1* | 12/2003 | Tanaka ................. B01D 65/022 134/22.1 |
| 6,679,274 | B2 | 1/2004 | Gruszczynski et al. |
| 6,945,257 | B2 | 9/2005 | Tabani et al. |
| 7,367,346 | B2 | 5/2008 | Tabani et al. |
| 8,361,944 | B2 | 1/2013 | Smith et al. |
| 8,647,443 | B2 | 2/2014 | Zhang et al. |
| 8,651,284 | B2 | 2/2014 | Wechs et al. |
| 2002/0112743 | A1* | 8/2002 | Tabani ................. A61C 1/0076 134/22.12 |
| 2004/0007255 | A1* | 1/2004 | Labib ................. A61M 1/1682 134/30 |
| 2010/0078047 | A1 | 4/2010 | Labib et al. |
| 2011/0048967 | A1* | 3/2011 | Pettee ................. C25B 1/34 205/766 |
| 2012/0093689 | A1 | 4/2012 | Thonhauser et al. |

OTHER PUBLICATIONS

"Reduction Potential" [online, retrieved on May 16, 2016], Wikipedia, 7 pages.*
International Search Report and Written Opinion of the International Searching Authority mailed Jul. 8, 2015 in corresponding International Patent Application No. PCT/US2015/026392.
GAMBRO. Polyflux. TM. L, 2008.
Association for the Advancement of Medical Instrumentation: Reuse of Hemodialyzers, ANSI/AAMI RD47:2002, Association for the Advancement of Medical Instrumentation, Arlington, VA, (2002).
Cheung, A. K., N. W. Levin, T. Greene, L. Agodoa, J. Bailey, G. Beck, W. Clark, A. S. Levey, J. K. Leypoldt, D. B. Omit, M. V. Rocco, G. Schulman, S. Schwab, B. Teehan, and G. Eknoyan, "Effects of high-flux hemodialysis on clinical outcomes: results of the HEMO study," J. Am. Soc. Nephrol., 14:3251-63, (2003).
Vanholder, R. and R De Smet, "Pathophysiologic effects of uremic retention solutes," J. Am. Soc. Nephrol., 10:1815-23, (1999).
Kaplan, A. A., Halley, S. E., Lapkin, R. A. and Graeber, C. W., "Dialysate protein losses with bleach processed polysulfone dialyzers," Kidney Int., 47:573-578, (1995).
Wienk, I. M., Meuleman, E. B., Borneman, Z., Van Den Boomgaard, T. H and Smolders, C. A., "Chemical treatment of membranes of a polymer blend: mechanism of the reaction of hypochlorite with poly(vinylpyrrolidone)," J. Polym. Sci., Part A: Polym. Chem., 33(1):49-54, (1995).
Gaudichet-Maurin, E., Thominette, F., "Ageing of polysulfone ultrafiltration membranes in contact with bleach solutions," Journal of Membrane Science 282(1-2):198-204, (2006).
Pellegrin, B., Prulho, R., Rivaton, A., Therias, S., Gardette, J-L, Gaudichet-Maurin, E., and Causserand, C., "Multi-scale analysis of hypochlorite induced PES/PVP ultrafiltration membranes degradation," Journal of Membrane Science 447:287-296, (2013).
Rouaix, S., Causserand, C., and Aimar, P., "Experimental study of the effects of hypochlorite on polysulfone membrane properties," Journal of Membrane Science 277(1-2):137-147, (2006).
Morti, S. M., and Zydney, A. L., "Protein-membrane interactions during hemodialysis: effects on solute transport," Amer. Soc. Artif. Intern. Organs J., 44, 319-326, (1998).
Wolff, S. H., and Zydney A.L., "Effect of bleach on the transport characteristics of polysulfone hemodialyzers," J. Membrane Sci. 243:389-399, (2004).
Wolff, S .H., and Zydney, A. L., "Effect of peracetic acid reprocessing on the transport characteristics of polysulfone hemodialyzers," Artif. Organs, 29(2):166-73, (2005).
Bosch, J. et al., Polyflux® Revaclear: The Next Generation in High-Flux Dialyzers, Gambro, www.gambro.com.

* cited by examiner

Polyethersulfone (PES)

Polyvinylpyrrolidone (PVP)

Scheme 1

Scheme 2

Figure 11: Schematic drawing of experimental apparatus used to determine dialyzer clearance.

COMPOSITIONS AND METHODS OF CLEANING POLYVINYL PYRROLIDONE-BASED HEMODIALYSIS FILTRATION MEMBRANE ASSEMBLIES

TECHNICAL FIELD

The technical field relates in general to compositions and methods for cleaning membrane assemblies which employ synthetic membranes that contain polyvinylpyrrolidone (PVP). The compositions and methods are effective in cleaning the hemodialysis membrane and the entire dialysis membrane assembly to restore the membrane clearance functions for small and middle molecules while minimizing damage to its porous structure and surface chemistry.

BACKGROUND

Dialysis is the most common method for treating patients with acute and chronic kidney disease termed as AKD and CKD, respectively. Hemodialysis is the most frequently prescribed dialysis treatment modality with more than two million CKD patients being treated worldwide annually which require performing more than 350 million treatments per year. Dialysis treatment involves circulating the patient's blood outside of the body through an extracorporeal circuit which consists of plastic blood tubing and a special membrane filter known as a hemodialyzer (dialyzer) with the aid of a dialysis machine that monitors and maintains blood flow and administers dialysate into the other side of the membrane at the same time. CKD patients require frequent dialysis treatment, three times per week or 156 times per year. The hemodialysis treatment is normally performed with large surface area (1.5-2.5 $m^2$) hollow fiber dialyzer comprised of thousands of hollow fiber capillaries encased in a clear plastic cylindrical housing (shell) 4 to 7 centimeters in diameter. There are two separate fluid compartments within the hemodialyzer, namely, the blood compartment and the dialysate compartment. Blood normally flows inside the lumens of the hollow fibers (blood compartment) and dialysate flows outside the hollow fibers within the external housing. The two compartments are sealed from each other and communicate only through the dialysis membrane where diffusion and convection transport takes place during dialysis.

The walls of the hollow fibers comprise the dialysis membrane where uremic toxins are removed from the patient's blood during the hemodialysis treatment, normally lasting 4 hours or more per treatment. This semi-permeable dialysis membrane separates the blood and dialysate buffer compartments and is specifically designed to allow the passage of certain sized uremic molecules (solutes) blood into dialysate while at the same time preventing the loss of other vital larger molecules such as albumin during the treatment. During hemodialysis, blood flows inside the lumens of the hollow fibers in one direction while the dialysate (bicarbonate buffer) flows on the outside of the hollow fibers in the opposite direction. This counter flow arrangement creates special pressure drop profile within the hemodialyzer which facilitates ultrafiltration to take place between the blood and dialysate during the treatment. This internal ultrafiltration process results in what is called convective flow of larger uremic toxin molecules (molecular weight between 500 Daltons and 25-30 kD) along with fluid resulting in their clearance/removal from the patient's blood. In this context, convective clearance resulting from ultrafiltration occurs via fluid exchange through the pore structure of the membrane with pore diameter in the range of 5 to 15 nm for high flux dialyzers. The ultrafiltration functionality of the membrane is simultaneously used to remove the excess fluid/water accumulated in the patient body during intradialytic time (approximately 2 days) with the aid of the dialysis machine and thus maintains the dry weight of the patient at the desired level as prescribed by the nephrologist. At the same time, electrolytes and dissolved gases in the dialysate buffer solution cross the membrane into the blood to chemically balance its composition as it is returned to the patient during dialysis treatment. Historically, dialysis was performed with low flux dialyzers with low ultrafiltration coefficient (<10 ml/hour/mmHg) and was thus limited to removing low molecular weight uremic toxins such as electrolytes, urea and creatinine. During the past 20 years, high-flux dialyzers with high ultrafiltration coefficient (>60 ml/hr/mmHg) have become the most common dialyzers used to perform hemodialysis. The main difference between low and high flux dialysis membranes relates to the surface density and size distribution of their pore structure.

For economic and environmental reasons, dialyzer reuse is commonly practiced worldwide. In the United States, about 50% of dialysis clinics still process and reuse the dialyzers. The currently accepted standard for dialyzer processing and reuse in the United States are those issued by the American Association for the Advancement of Medical Instrumentation (AAMI). AAMI guidelines were developed to ensure that a dialyzer's urea clearance will not fall below 90% of its first use baseline value. Since it is not practical to determine the urea clearance value before each use, AAMI standards regard measurement of the blood compartment volume of the dialyzer, referred to as the "total cell volume" (TCV), as equally satisfactory. Therefore, a dialyzer must maintain a TCV of greater than 80% of its original baseline TCV to ensure that its urea clearance is within the acceptable range as required by the AAMI guidelines.

During reprocessing, the dialyzer is normally flushed with reverse osmosis (RO) water to remove any remaining residual blood and the TCV is then measured. If the dialyzer passes the 80% TCV criterion and is leak-free (no broken fibers), it is then high-level disinfected with an FDA-approved liquid germicide. Peracetic acid (PAA) is widely used to perform this step which requires at least 11 hours of dwell time, with the dialyzer fully filled with about 1200 to 1700 ppm PAA, before the dialyzer can be used to perform the next treatment. According to AAMI guideline, the dialyzer must be issued to the patient and used by the same patient until it fails. This practice is required to eliminate the risk of cross contamination/infection among patients.

Recently, the importance of effective clearance of middle molecular weight uremic toxins (500 to about 25,000 Daltons) by high-flux dialyzers on clinical outcomes has been recognized as necessary to decrease mortality and morbidity of cardiovascular disease in CKD patients, the main cause of mortality in this group of patients (Cheung et al, 2003). Close to 100 different uremic molecules have been identified, many of which are in this middle molecular weight range (Vanholder et al, 1999). Many of such middle molecules are removed or cleared from blood via convective flow due to the internal ultrafiltration process taking place in the dialyzer during high-flux dialysis. The convective clearance by ultrafiltration depends directly on the pore size distribution of the pore structure of the membrane which becomes fouled, clogged and compromised during the course of the hemodialysis treatment. Therefore, any effective cleaning process must ensure that the membrane retains its effectiveness in removing middle molecular weight uremic toxins during each and every dialysis treatment.

An equally essential consideration associated with dialyzer reuse concerns the effect of the cleaning composition and cleaning method on the chemical composition and the pore size distribution of the hollow-fiber dialysis membrane. Modern hollow fiber dialysis membranes are based on durable engineering polymers which can be made into hollow fibers in large scale manufacturing. Polysulfone (PS), polyethersulfone (PES) and their copolymers have become the main base polymers used to make hemodialysis hollow fiber membranes because of their superior mechanical properties and their propensity to form membrane structure. Since PES and its copolymer variants are intrinsically hydrophobic and not hemocompatible, a blend of PES and polyvinylpyrrolidone (PVP) is currently employed to impart hydrophilicity to the membrane surface and to make it hemocompatible. FIG. 1 shows a chemical formula for polyethersulfone (PES) and polyvinylpyrrolidone (PVP), respectively. At the right level of PVP (2-5%) in the blend, the interior skin surface (fiber lumen) of the membrane becomes hydrophilic and hemocompatible. The current process of hollow fiber manufacturing is designed to make an asymmetric membrane with the PVP-rich skin layer located at the lumen side of the hollow fibers where blood comes in contact with during dialysis. Basically, the membrane skin layer at the lumen surface controls the sieving coefficient of larger molecules as well as imparting the hemocompatibility function of the dialyzer. However, PVP is much less chemically resistant compared to PES and is attacked by strong chemicals used to clean/process the dialyzer for reuse. Exposure of the dialysis membrane to harsh chemicals during cleaning can lead to PVP erosion, increasing membrane hydrophobicity, opening/widening of membrane pores, shifting of the pore size distribution to larger sizes and eventually leading to leakage of important serum proteins such as albumin. Other consequences to the PVP erosion and loss can also lead to hemo-incompatibility and to activation of the immune system including the complement system due to change in surface chemistry, increased surface roughness, and increased hydrophobicity.

Dialyzer reuse has been practiced in dialysis clinics for more than 45 years because of the high cost of early hemodialyzers. The dialyzer reuse practice has witnessed many developments over the years, and was initially done manually by dialysis technicians. The first widely used automated dialyzer reprocessing system was made by the Fresenius Company (DRS-4) to replace the manual processing of dialyzers and was based on cleaning the dialyzer with a commercial bleach solution followed by disinfection with a formaldehyde solution. DRS-4 automated the manual practice to some extent and was based on first cleaning the dialyzer with about 0.5 to 1.0% un-buffered commercial hypochlorite bleach solution at pH about 7.5 to 9.0. According to this system, the dialyzer must be first cleaned manually with RO water at the sink to remove blood clots and residual blood. This step was followed by cleaning the dialyzer with commercial bleach at the above concentrations for several minutes at about 37° C. The dialyzer was then rinsed after the bleach cleaning using AAMI RO water, filled with formaldehyde or glutaraldehye germicide and then stored in an oven at elevated temperature overnight to achieve high level disinfection. This process, termed bleach-formaldehyde method, was the main practice in dialyzer reuse for many years and was practiced in 90% of dialysis clinics in the United States. The main limitation of this practice was recognized when dialyzers processed according to this method led to albumin loss in CKD patient during dialysis as reported by Kaplan (Kaplan et al, 1995). Many subsequent reports elucidated that the loss of PVP from the membrane due to attack by hypochlorite bleach during processing was the main cause of albumin loss found in dialysis patients.

In recognition to these issues, the industry has moved towards using peracetic acid as the only agent to process and disinfect the dialyzer for reuse. Within a few years, peracetic acid dialyzer reprocessing completely replaced the bleach-formaldehyde process and has remained the main processing method since 1985. However, it was quickly recognized that peracetic acid processing, although it does not affect the PVP layer, it does not remove residual fouling protein from the dialyzer membrane. As a result, the pore structure of the membrane becomes clogged after one or two uses resulting in a significant loss in clearing middle molecules during dialysis. In other words, the high flux dialyzer becomes low flux dialyzer after only one or two treatments when the dialyzer is processed with peracetic acid. Being highly acidic, peracetic acid was found to denature residual patient proteins and make them tenaciously adhere to the inside of the pores and onto the lumen surface of the hollow fiber membrane. These undesired outcomes have been found to degrade the clearance of middle molecules including beta-2 microglobulin (Cheung et al, 2003). In addition, since peracetic acid itself does not clean the dialyzer, a very time consuming manual cleaning step must be employed to remove residual blood and clots from the dialyzer before it is filled peracetic acid. This manual step was found to require about 70% of the reuse technician time and to expose patients to risk of infection. Hence, peracetic acid reprocessing system has fallen out of favor due to the significant loss in middle molecules clearance and because of high risk of infection arising from the manual cleaning step. Therefore, new cleaning compositions and methods are most urgently needed to deliver safe and effective outcomes in reprocessing hemodialyzers without compromising the middle molecules clearance and without affecting the pore size distribution of the dialysis membrane. These desired compositions and methods are also needed to decrease the cost of delivering dialysis and to eliminate the tremendous medical waste arising from the disposal of single-use non-biodegradable dialyzers in landfills. It is now estimated that more than 350 million hemodialyzers will need to be disposed of in landfills every year if the dialysis industry would adopt the single-use option to treat CKD patients worldwide.

The dialysis industry is very much concerned about the degradation of PVP containing PES membranes since such degradation will impact the effectiveness of dialysis treatment and may result in health risks due to loss albumin from patients during dialysis. Loss and erosion of PVP from dialysis membranes can also affect the hemocompatibility resulting in adverse effects on the immune system such as inducing the compliment activation.

Exposure of PVP-containing PES membranes to hypochlorite solutions results in selective leaching of the PVP from the membrane. The PES component of the membrane is fairly resistant to hypochlorite, but the damaging effect on the membrane only takes place when PVP is leached out form the pore structure of the membrane (Wienk et al., 1995; Gaudichet-Maurin et al., 2006).

Wienk et al., (1995) proposed that the selective elimination of PVP from the membrane matrix may follow two main distinct mechanisms as follows (FIG. 2): a) chain session of PVP resulting in molecular weight reduction which is followed by the PVP component being washed out from the membrane structure, and b) oxidation of PVP in alkaline solutions at pH 11.5 with pyrrolidone ring opening in agreement with the work of Anderson et al., (1979). Although the above two mechanisms were advanced by Wienk et al. (1995), their experimental results indicate that the decrease in the molecular weight of PVP is the highest at pH 11.5 which is contradictory to the reactions proposed in their paper.

U.S. Pat. Nos. 6,945,257 and 7,367,346 introduced the two-phase treatment method to clean and process dialyzers and showed that this method is effective in recovering the TCV of patient dialyzers. According to their disclosure, cleaning solutions with pH higher than 7.0 as well as those with pH in the acid region (<pH 7.0) can be used to clean the dialyzers and recover TCV according to this method. The use of solutions based on hydrogen peroxide or peroxy acids for processing hemodialyzers is known in the dialysis industry. U.S. Pat. Nos. 6,945,257 and 7,367,346 use a cleaning solution at pH 11.3 because this pH is higher than the is-electric point of the most basic serum protein known and they suggest cleaning at this pH value for the purpose of making all serum proteins negatively-charged when in contact with the cleaning solution, thus facilitating the removal of all serum proteins from the membrane surface because of electrostatic repulsion. However it is noted that the pH 11.3 solution is not hypochlorite based. While the cleaning solutions of embodiments may be useful for several purposes, they fail to disclose the use of a hypochlorite composition for cleaning at a pH of at least 12.0. As it will become evident in the following discussion, the above conditions provided in U.S. Pat. Nos. 6,945,257 and 7,367,346 do not provide guidance regarding compositions that prevent the degradation of PVP-containing dialysis membranes.

Pellegrin at al., (2013) performed a multi-scale analysis of hypochlorite induced PES-PVP membrane degradation in relation to using such membranes in drinking water purification which normally contains low-level chlorine (maximum 100 ppm) for the purpose of disinfection. These authors concluded that high reactivity of PVP to hypochlorite at the maximum reaction rate takes place at neutral to slightly basic pH (up to pH 8.0). The degradation of the PVP component in PES-PVP ultrafiltration membranes reported by these authors is in agreement with the findings by Kaplan et al., (1995) where exposure of PVP-containing dialysis membranes to un-buffered NaOCl was found to result in albumin loss in patients during dialysis. Rouaix et al., (2006) also explored the effect of hypochlorite on PVP-containing membranes in applications related to drinking water purification and concluded that the application of these membranes at pH 8.0 and 10.0 should be avoided and that the reaction of hypochlorite with the membrane structure is a temperature activated process. These authors did not investigate the effect of hypochlorite beyond the concerns of applications of drinking water purification.

The food industry extensively employs ultrafiltration membrane separation processes where frequent membrane cleaning is required to restore water-flux during production. The most prevalent membrane used in the food industry is based only on PES without PVP inclusion and therefore this industry is not concerned about membrane degradation due to PVP. The cleaning process in the food industry is normally preformed in two steps: (i) an alkaline cleaning step at pH up to 11.3 and this is normally followed by (ii) an acid cleaning step performed at pH about 3.0 to 4.0. The latter acid step is employed to dissolve the calcium scale deposited in the membrane mostly in the dairy industry such as in the process of whey separation. The cleaning solutions used this industry normally include different surfactants.

In the biotechnology industry, either polysulfone (PS) or polyethersulfone (PES) membranes are used to perform separation processes. These membranes are normally cleaned at very high pH (>pH 13) based on 0.5N NaOH and sometimes with the addition of NaOCl; however, there is no concern about the degradation of membranes used in biotechnology separations because they do not contain PVP. The cleaning compositions used in these applications while useful for cleaning certain membranes are not applicable to the medical equipment of dialysis membrane assemblies.

As mentioned above, in order to clean dialysis membrane assemblies or dialyzers, the dialysis industry for many years used commercial bleach solutions at 0.5% to 1.0%, or 5,000 to 10,000 ppm without pH adjustments. Based on the dissociation properties of NaOCl, the effective concentration free chlorine or HOCl used in the DRS-4 method at the expected pH is estimated to be in a range of about 5000 ppm. The DRS-4 method was found to cause a significant degradation of the polysulfone-based membranes that include PVP and was manifested clinically by patient's albumin loss in dialysis treatment. The dialysis industry reacted to this in two ways: 1) by reformulating the polymer blend of PES-PVP to make more hypochlorite-resistant dialysis membrane, and 2) by moving away from hypochlorite cleaning of dialysis membrane altogether.

The low pH of peracetic acid and its non-specific reactions with proteins are now recognized as the main limitations of this method. Hence, peracetic acid is currently recognized as a disinfectant solution only.

Until now, there has been a compromise in the formulation of the cleaning compositions for dialyzers between the cleaning power required to effectively remove blood protein residue and the influence of the cleaning composition on degrading the membrane material especially with respect to the pore structure of the membrane. This degradation has been recognized to be mostly due to the chemical erosion of PVP component of the dialysis membrane. For example, peracetic acid which is the most widely used agent in dialyzer reprocessing, does not lead to erosion of PVP in PVP/PES-based membranes but also has been associated with a decrease in TCV and a significant decrease in the clearance of middle molecules because of the incomplete removal of fouling protein residue from the pores and surface of the (Cheung et al., 2003). As mentioned above, earlier cleaning systems based on un-buffered bleach solutions such as those used DRS-4, were found to remove PVP from the membrane, cause further damage to other polymers (possibly polysulfone), shift the pore size distribution to large pore sizes and lead to albumin loss from patients during dialysis treatment.

Particularly with the advent of high-flux dialyzers and with the recognition of the importance of the clearance of middle molecules during dialysis, the peracetic acid method limitations have become unacceptable in treating dialysis patients. In this context, the acid pH and inability of peracetic acid to remove the irreversibly-adsorbed protein form the pore structure of the dialysis membrane are now accepted as the main limitation of the PAA (peracetic acid) method. Another major limitation of the peracetic acid dialyzer processing method includes the need to manually clean the dialyzer before disinfecting the dialyzer prior to automated processing. The manual handling during PAA processing has also resulted in several episodes of infection in dialysis patients as reported by the Center for Disease Control (CDC). Due to the above limitations and high labor cost, the peracetic acid method for dialyzer processing has fallen out of favor in the industry.

For more than thirty (30) years, the dialysis industry has been unsuccessful in solving the problem of membrane degradation arising due to PVP erosion from cleaning hemodialyzers. Considering the inherent limitations of cleaning dialysis membranes with peracetic acid or similar approaches, there is an urgent need for compositions and methods that can effectively restore and regenerate the performance of PVP-containing dialysis membranes and recover of the clearance of small and middle molecular weight uremic molecules without degradation or adverse effects to dialysis patients.

SUMMARY

Accordingly, one or more embodiments provide improved compositions and methods for cleaning, reprocessing and regenerating hemodialysis membrane assemblies that employ polyvinylpyrrolidone (PVP)-containing membranes, and to recover the clearance of middle molecules function of the membrane after each dialysis treatment and for many dialysis treatments without loss in performance. The compositions and methods provide effective removal of membrane fouling proteins and other contamination arising from hemodialysis treatment (blood clots and the like) yet minimize damage to the membrane arising from chemical erosion of the PVP component (i.e., oxidation, breakdown, and dissolution/dispersion of the PVP). Surprisingly, a composition based on a hypochlorite salt solution with high pH and high alkalinity that is nearly HOCl-free and having an oxidation-reduction potential (ORP) of less than 0.5 volts was not strong enough to degrade PVP-containing membrane but sufficient enough to breakdown and remove membrane fouling proteins that cause loss of the clearance functions of said dialysis membranes.

Embodiments provide for cleaning the entire dialysis membrane assembly including the housing, tubing and membrane which employs polyvinylpyrrolidone-containing polymers such as polysulfone (PS) or polyethersulfone (PES). The intended dialysis membrane may be asymmetric with the membrane skin layer present at the fiber lumen side, or on the external surface of the hollow fiber, or on both the lumen and external surface of the hollow fiber; the latter is otherwise known as a "double-skinned" membrane.

One embodiment encompasses cleaning compositions comprising an inorganic base and from about 50 to about 1,000 ppm of a hypochlorite salt; less than 50 ppb free HOCl; a pH between about 12.2 and about 12.5 (high alkalinity); an oxidation-reduction potential of less than 0.5 volts; and a mole % of hypochlorous acid, HOCl, relative to the sum of hypochlorous acid plus hypochlorite anion (—OCl) of less than 0.004%. Each of these characteristics of the compositions has been found to be important to provide effective cleaning of PVP-containing hemodialysis membranes without causing damage to said membrane or erosion of the PVP component of the membrane.

In one embodiment of the composition, the hypochlorite salt is sodium hypochlorite, and the base salt providing the high alkalinity (total OH⁻ concentration) is sodium hydroxide.

One embodiment of the composition includes about 0.1% to about 0.5% by weight of sodium or potassium phosphate.

One embodiment of the composition further includes a salt that is a member selected from the group consisting of phosphates, benzoates, salicylates, citrates, carbonates, silicates and mixtures thereof.

In one embodiment, the composition contains about 50 to about 1,000 ppm sodium hypochlorite; about 0.1% to about 0.5% sodium phosphate and sufficient sodium hydroxide to provide a pH of about 12.2 to 12.5 during the cleaning of the dialysis membrane.

The preferred compositions include an entirely aqueous mixture of water-soluble inorganic compounds without organic surfactants. The compositions also preferably and additionally include preferred inorganic salts to modulate the rates of reaction with the PVP component of the dialysis membrane. The embodiments can target applications related to treating dialysis patients and/or other applications in biotechnology or other industries where control of protein separation is needed. The embodiments can cover uses in other treatment therapy modalities in addition to hemodialysis including but not limited to hemodiafiltration, hemofiltration, plasmapheress and the like. In special applications the compositions may also include organic surfactants and should not be limited to using all inorganic salts in all cases.

In another embodiment, removal of membrane fouling proteins that cause the loss of clearance functions of middle molecules during dialysis was found to require specific chemical reactions that act to cleave and facilitate desorption of such fouling proteins from the surface and pore structure of the dialysis membrane. Specifically, some forms of hypochlorite species and other related chemical species have been found to perform such reactions and are able to breakdown such fouling proteins and lead to their removal from the membrane.

The composition and method embodiments can be especially useful in the regeneration (recovery of small and middle molecule clearance function of the membrane to original baseline levels) of dialyzer membranes based on PS-PVP or PES-PVP composite hollow fibers. Other base primary polymers are also included as per the known art of making hemodialysis membranes and are not limited to PS and PES. According to an embodiment, the base polymer may also comprise polymer blends which may include polyamides alone or in addition to polysulfone-based polymers including those with aromatic linkages and other organic groups. Embodiments should not be limited to polysulfone-based base polymers as long as the blend includes PVP, its copolymers or derivatives or other similar hydrophilizing agents including polyethylene glycol (PEG) or the like. An embodiment can cover different PVP species irrespective of their molecular weight or molecular weight distribution, and no matter how the PVP component is distributed within the polymer blend.

Embodiments can encompass treatment methods of using the inventive compositions to clean hemodialysis membranes. In general, three modes of treatment can be employed: liquid backflow or backfiltration, two-phase treatment and static contact. These modes of treatment can be used individually or in combination and the cleaning treatment can also include various instruments or devices to deliver, control and monitor process variables such as solution conductivity, pH, oxidation reduction potential (ORP), hypochlorite concentration, temperature, pressure and flow rates. Embodiments may cover the needed delivery devices to add and proportion ingredients during the course of cleaning and processing.

In particular, a method of cleaning a hemodialysis filtration membrane assemblies having PVP-containing membranes, the method can comprise the step of treating the assembly for 5 to 10 minutes with a composition at a temperature of about 40° C. to about 55° C., the composition can comprise: an inorganic base/s; from about 50 to about 1,000 ppm of a hypochlorite salt; less than 100 ppb free HOCl; a pH between about 12.0 and about 12.5; an oxidation-reduction potential about 0.5 volts; and a mole % of hypochlorous acid, HOCl, relative to the sum of hypochlorous acid plus hypochlorite anion, is less than 0.004%.

In another embodiment the method also includes the step of immediately rinsing the assembly after exposure to the composition with reverse osmosis (RO) water at ambient temperature.

In yet another embodiment the reprocessing method also includes a step of acid polishing to further improve the effective of removing membrane fouling proteins.

In another embodiment the cleaning composition is supplied as a concentrate and the method further comprises the step of diluting and proportioning the concentrate immediately before application of the formed use composition to the dialysis membrane assemblies.

In yet another embodiment the treatment method includes the step of pumping the cleaning composition under pressure through one of the dialysate outlet tubes and allowing the composition to pass through the membrane and then exit the dialyzer assembly through the ports of the blood compartment and wherein during cleaning there are alternating cycles involving flow of the cleaning solution on the lumen side only for some time followed by backfiltration through the membrane for another period of time so that the cleaning composition is in contact with all the pores and the entire fiber surfaces at the same time but the total time of membrane exposure to the cleaning composition does not exceed 10 minutes. According to this embodiment the composition also cleans other parts and surfaces of the dialyzer including its headers, potted surface of fiber bundle and ports so that the entire dialyzer assembly is completely cleaned to remove patient material, including blood clots, protein residues as well as membrane fouling proteins.

In another embodiment the inventive composition is applied to the membrane assembly as a mixture of gas and liquid for 5 to 10 minutes and wherein the liquid fraction comprises the inventive composition and is provided to the assembly by backfiltration from the dialysate compartment at a temperature of about 40° C. to about 55° C. and at volumetric flow rates between 100 and 600 ml/minute and the gas fraction comprises compressed air delivered through the lumens of the hollow fiber membrane at the ambient temperature at volumetric flow rates between 50 to 150 liters per minute at STP and wherein the composition produces surface active protein fragments that decrease surface tension of the liquid fraction to less than 72 dynes/cm.

In yet another embodiment, a cleaning composition comprises a mixture of a gas and a liquid wherein the gas fraction is a compressed air and the liquid fraction is an inorganic base/s; from about 50 to about 1,000 ppm of a hypochlorite salt; less than 100 ppb free HOCl; a pH between at least 12.0 and about 12.5; an oxidation-reduction potential about 0.5 volts; and a mole % of hypochlorous acid, HOCl, relative to the sum of hypochlorous acid plus hypochlorite anion, is less than 0.004%. The gas-to-liquid ratio of this inventive composition is between about 200:1 and 500:1 and is either delivered directly to the lumen side of the dialyzer or formed in situ by mixing the gas with the back-filter liquid inside the fiber lumens of the dialyzer.

According to another embodiment the cleaning rate dialysis membrane is found to depend on the application temperature, hypochlorite salt concentration, and alkalinity as defined by hydroxide ion concentration and the oxidation-reduction potential of the composition. The high alkalinity of the composition may be further increased by the addition of phosphates or other similar alkalinity boosting salts. The high alkalinity is also desirable to ensure that the concentration of free chlorine (HOCl) is less than 0.004% of added hypochlorite salt concentration and that this is important in minimizing the degradation of the PVP component of the membrane. The cleaning rate according to the embodiment needs to achieve the removal of membrane fouling proteins in a short time (5 to 10 minutes) and to minimize the rate of degradation of the PVP component of the membrane. The rate of PVP degradation seems to be inversely dependent on the alkalinity of the cleaning composition and it needs to be controlled during the cleaning.

The compositions and methods of embodiments may be modified as needed by the user to optimize the cleaning of dialysis membranes made by different manufactures while minimizing membrane degradation.

As a further embodiment, an instrument or apparatus to perform fully automated cleaning and processing of dialyzers comprises delivering the inventive compositions to the dialyzers, adjusting and controlling the treatment parameters and monitoring the critical parameters so that no manual handling of the dialyzers is required.

Adopting dialyzer processing according to the compositions and treatment methods of an embodiment in the dialysis industry may be critical to decreasing the number of dialyzers needed to treat the more than the two (2) million CKD dialysis patients worldwide by a factor of 40 annually. Furthermore, adoption of the methods and compositions of an embodiment can reduce medical waste arising from hemodialyzer disposal in landfills by 97.5%. An embodiment is envisioned to enable the use of only 8.75 million dialyzers to treat all CKD patients worldwide instead of the 350 million single use dialyzers per year. Cost reduction to the healthcare system from this technology can be significant considering that the dialysis program is the largest cost item according to United States Centers for Medicare & Medicaid Services (CMS). As it will be detailed in the specification, the combination of the compositions and methods of embodiments can recover the clearance of uremic small and middle molecules of the dialyzer after each treatment to baseline values and thus there is no decline in the quality of treating patients compared to the single use practice.

Yet another embodiment comprises a membrane that has been treated with compositions and methods herein disclosed. In particular, exposure of PVP containing membranes to the compositions and methods herein disclosed appears to alter the membrane itself rendering it distinct from the membrane prior to exposure.

As demonstrated above, numerous embodiments are available for the user to optimize the composition and methods needed to treat specific membranes within the scope of the invention. Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

BRIEF DESCRIPTION OF THE DRAWINGS

The accompanying figures, where like reference numerals refer to identical or functionally similar elements and which together with the detailed description below are incorporated in and form part of the specification, serve to further illustrate various exemplary embodiments and to explain various principles and advantages in accordance with the embodiments.

DETAILED DESCRIPTION

Figure 1:
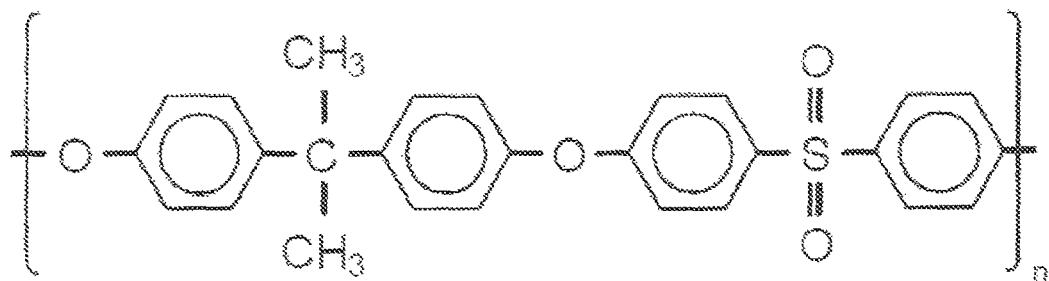
FIG. 1 is a molecular structure diagram of the primary polymer polyethersulfone (PES) and the hydrophilizing polymer polyvinylpyrrolidone (PVP) used to make the PVP-containing membrane according to an embodiment.
Figure 1:
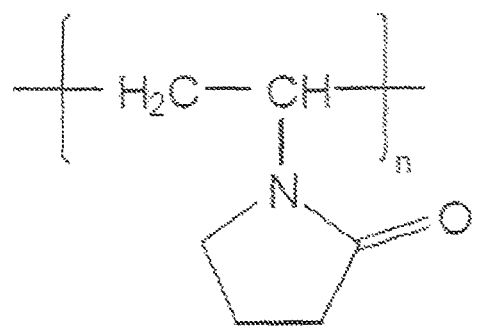

In overview, the present disclosure concerns improved methods and compositions for dialysis membrane cleaning. More particularly, various inventive concepts and principles are embodiments in systems, devices, and methods therein for effective removal from PVP containing dialysis membranes of middle molecular weight contaminating proteins without detrimental effect on the PVP content of the membrane.

The instant disclosure is provided to further explain in an enabling fashion the best modes of performing one or more embodiments. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

It is further understood that the use of relational terms such as first and second, and the like, if any, are used solely to distinguish one from another entity, item, or action without necessarily requiring or implying any actual such relationship or order between such entities, items or actions. It is noted that some embodiments may include a plurality of processes or steps, which can be performed in any order, unless expressly and necessarily limited to a particular order; i.e., processes or steps that are not so limited may be performed in any order.

As further discussed herein below, various inventive principles and combinations thereof are advantageously employed to maintain PVP dialysis membrane function while still providing removal of all contaminating material therefrom Composition Embodiments The compositions have the effect of removing tenaciously fouling serum proteins from dialysis membranes without attacking the PVP component of the membranes, thereby permitting multiple uses and withstanding more than 40 cleaning cycles without degradation in hemocompatibility or loss in the clearance of small and middle molecules. The contents of the cleaning composition will now be described. The composition of embodiments can comprise entirely inorganic salts that are completely soluble in pure water both in the form of concentrate and at the use concentration. The aqueous cleaning composition comprises an aqueous base and from about 50 to about 1,000 ppm of a hypochlorite salt, the mixture having high alkalinity with pH between 12.2 and 12.5 at the use concentration and where the pH remains within this range during cleaning. The composition also has the characteristic that the mole % of hypochlorous acid, HOCl, relative to the sum of hypochlorous acid plus hypochlorite anion (—OCl), is less than 0.004%. The concentration of HOCl or free chlorine in the composition is in the range of about 0.4 to 50 ppb. These nearly HOCl-free compositions have an oxidation-reduction potential of about or less than 0.5 volts. The compositions may also include a phosphate salt or other salts. Each of the characteristics of the composition will now be described in detail.

Hypochlorite Salts at pH 12.0-12.5

There are two classes of serum proteins that foul the dialysis membrane after dialysis treatment that degrade its performance. One class leads to loss of the dialyzer TCV and the other results in the loss of permeability with concomitant loss of convective flow leading to loss in the clearance of middle molecules of the membrane. The second class of membrane fouling proteins also results in the decrease of sieving coefficients of uremic middle molecules.

Using inorganic bases alone (e.g., NaOH) at the high pH conditions (12.0 to 12.8) to be only effective in recovering the TCV of PVP-containing hemodialyzers membranes (Example 2). However, despite the high pH conditions and high treatment temperature (about 40° C.-about 55° C.), the cross flow hydraulic permeability and clearance of the middle molecules remain highly impaired (about 50% of baseline values compared to a new dialyzer) even after exposing the membrane to a single dialysis treatment. Loss of membrane ability to remove middle molecular uremic toxins during dialysis treatment is unacceptable since this leads to development of cardiovascular disease which is the cause of mortality in CKD dialysis patients. Accordingly, cleaning compositions based with very high pH (high alkalinity) alone are insufficient to clean the membrane pore structure of dialysis membranes. Although high pH compositions do not adversely affect the PVP content of the membrane, they are not effective cleaning agents. These results indicated that although high pH solutions can solubilize and/or hydrolyze some residual proteins present in the lumen of the hollow fiber membrane and substantially recover TCV, they are almost entirely "ineffective" in removing highly adhering fouling proteins lodged in the pore structure of the membrane which are responsible for middle molecules clearance. This has led us to conclude that there are two classes of serum proteins that remain within the membrane after dialysis. Proteins of the first class can be partially solubilized/hydrolyzed and removed by compositions having high pH only, and proteins of the second class of membrane fouling proteins is resistant to high pH cleaning even at treatment temperatures about 50° C. or even higher. It also appears that proteins belonging to the second class are irreversibly adsorbed or irreversibly lodged in the pore structure of the membrane and cannot be removed with physical action of backfiltration treatment methods at high pH and high temperature.

The first class of membrane fouling proteins can be partially cleaned or removed by the action of high pH or high concentration of caustic only and is mostly responsible for the loss in TCV since they tend to heavily accumulate inside the fiber lumens and thus result in decreasing the effective volume of the hollow fibers. Cleaning of this class of serum proteins is faster at higher pH and higher temperature. Proteins in the class may comprise albumin and other high molecular weight serum proteins which are known to reversibly desorb from the polymeric surface of dialysis membranes.

The second class of membrane fouling proteins cannot be cleaned or removed by high caustic or high pH alone, and proteins in this class are responsible for clogging the pore structure of the dialysis membrane leading to the loss of permeability which results in the loss of convective clearance of uremic middle molecules. Uremic middle molecules here are defined as those having molecular weight from 0.5 kD to 30 kD, or even up to 60 kD. We found that membrane fouling proteins belonging to this second class advantageously used special chemical reactions with some form of hypochlorite compounds or species or other related reactive species such as those present in the inventive composition to remove them from the membrane. Such reactions lead to the breakdown of these fouling proteins into smaller fragments and/or cause change in their chemical properties leading to their desorption and ultimate removal from the membrane surface and form pore structure. These proteins seem to adsorb very irreversibly onto the surfaces of the membrane and onto the surface of the pore structure and that removing them advantageously used chemical reactions that lead to their breakdown into fragments, desorption, solubilization and then eventual removal from the membrane. Membrane fouling proteins belonging to this second class may include fibrinogen, fibronectin and other special molecules involved in thrombosis which are known to adsorb irreversibly onto native polymeric surfaces including those of dialysis membranes.

Figure 3:
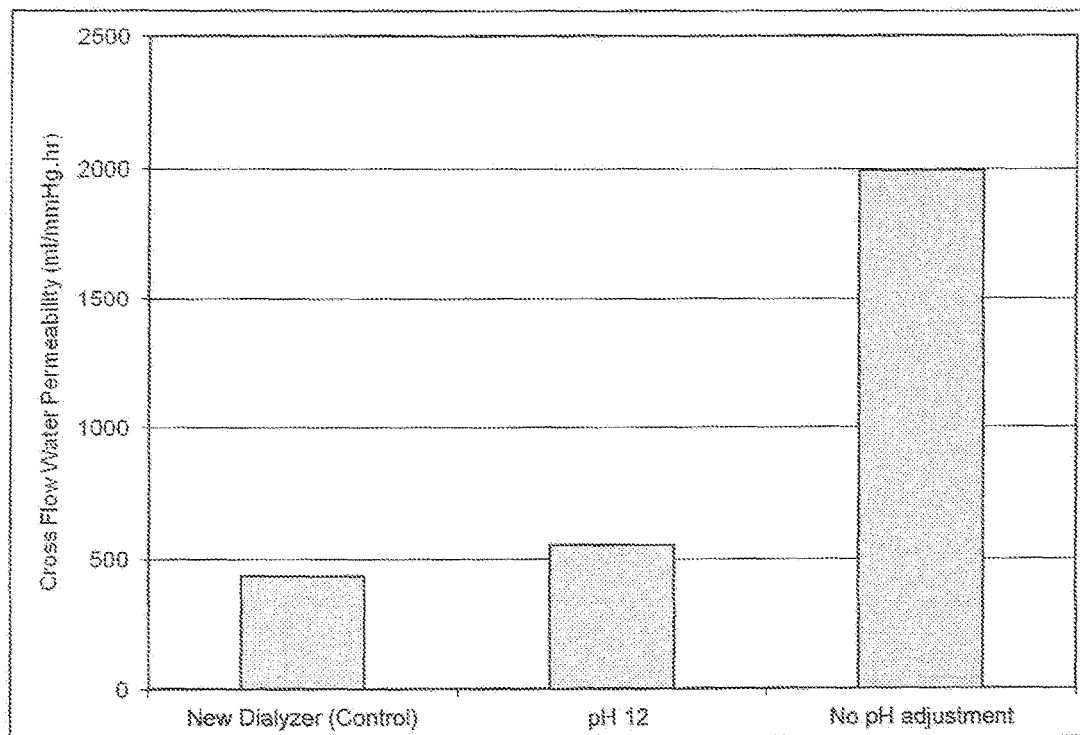
FIG. 3 is a graph showing the cross flow water permeability (Lp) of a Gambro Polyflux® 21R dialyzer after twenty (20) simulated cleaning cycles in the presence of a hypochlorite salt (500 ppm) at different pH conditions. Composition 1 was based on pH 12.3 and 500 ppm hypochlorite according to an embodiment. Composition 2 was made with 500 ppm hypochlorite using commercial bleach without pH adjustment (pH=8.0).

One of the novel inventive features of an embodiment of the composition is the use of a hypochlorite solution at a pH of at least 12.0 to about 12.5 during cleaning. FIG. 3 shows the cross-flow water permeability for Gambro POLYFLUX® 21R dialyzer after 20 simulated cleaning cycles with hypochlorite solutions (500 ppm as sodium hypochlorite) at pH 8 (un-buffered) and at pH 12 according to an embodiment, respectively. There is significant retention of cross flow water permeability when the inventive cleaning composition made at pH 12.0 is used to clean the dialyzers.

Merely using a cleaning composition without hypochlorite salt at pH greater than 12.0 is only sufficient to remove some proteins from dialysis membranes, but not sufficient to remove all membrane fouling proteins, notably those that control convective clearance of middle molecules (Example 2). More novel features of various embodiments will now be described.

Nearly HOCl-Free Compositions

Figure 4:
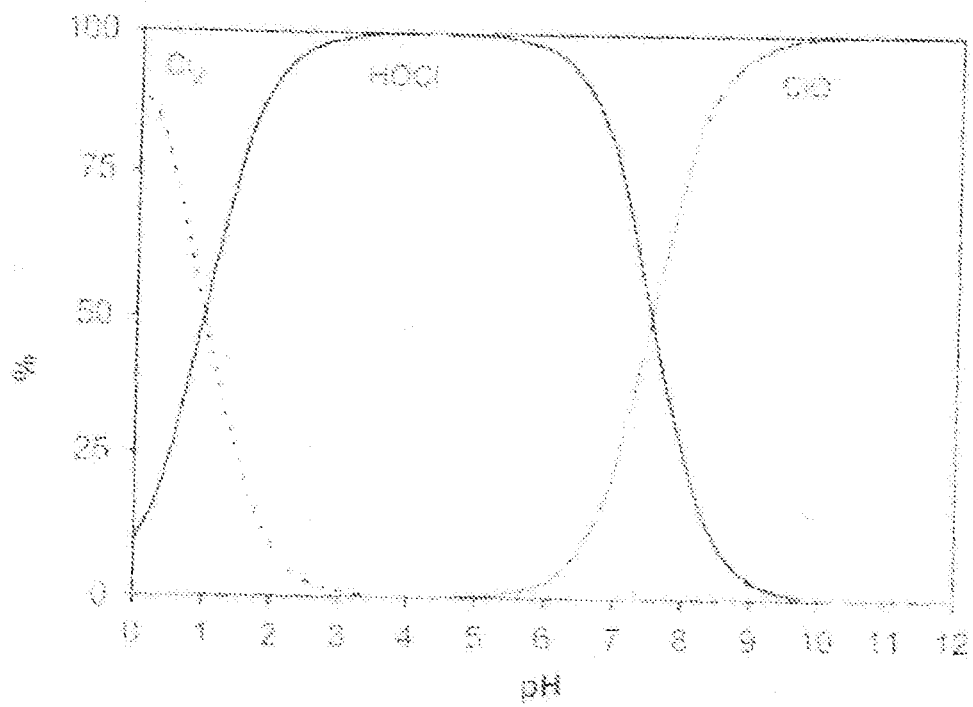
FIG. 4 is the ionization/dissociation diagram of hypochlorite showing the percent distribution of HOCl and ClO$^-$ as a function of pH.

Use of hypochlorite salts for disinfection is well known in the art. Consumption of hypochlorite due to reaction with proteins is also known and well recognized in the art. In physical chemistry, there is a well-established correlation between pH and the percentages of hypochlorous acid (HOCl) versus hypochlorite ion —OCl as defined the ionization constant of HOCl. FIG. 4 describes this relationship. HOCl is generally considered a fast-acting free chlorine disinfectant whereas —OCl is a slow acting sanitizer and a very poor disinfectant. —OCl has a much lower oxidation-reduction potential as described in the specification. Looking at FIG. 4, most protocols for disinfection employ hypochlorite salts at the condition necessary to maintain the highest possible concentration of HOCl, as it has the highest oxidation-reduction potential and would therefore use solutions generally recommended at a pH between 5.0 to 8.0.

Notice that pH 12.0 to 12.5 is at the extreme end of the ionization curve for hypochlorite where there is almost no change in percent dissociation values (FIG. 4). This leads to the second novel feature of an embodiment of the composition of the present invention in that at pH at least 12.0 to about 12.5, there should be essentially all —OCl (hypochlorite anion) and no HOCl molecules present. That is, mole % of hypochlorous acid, HOCl, relative to the sum of hypochlorous acid plus hypochlorite anion (—OCl) is less than 0.004%.

In contrast to commonly employed methods of cleaning PVP-containing hemodialysis membranes with commercial chlorine bleach delivered without pH adjustment or without other means of controlling the dissociation properties such as in the DRS-4 method, we have found that the level of inorganic base present (defined also in terms of total alkalinity) in the embodiments of compositions of the invention must be chosen to minimize the concentration of hypochlorous acid (HOCl), also known as "free chlorine". Specifically, the % of (HOCl), defined as the molar concentration of hypochlorous acid [HOCl] divided by the molar concentration of hypochlorous acid plus the molar concentration of hypochlorite anion, [—OCl], should be substantially zero to minimize chemical attack and erosion of the PVP from PVP-containing dialysis membranes. The term "substantially zero" is a % HOCl less than about 0.004%, preferably less than 0.003% and most preferably less than 0.002%.

The % HOCl is related to the pH of a hypochlorite solution through the well know dissociation equilibrium and is given by the Equation 1:

$$\% \text{ HOCl} = 100/(1+K_d/(10^{-pH}))  \qquad \text{Equation 1}$$

where $K_d$ is the dissociation constant for hypochlorous acid and is around $2.5 \times 10^{-8}$ at 20° C.

Embodiments of the compositions are novel in that very low concentrations of hypochlorous acid are present during cleaning of PVP-containing dialysis membranes. The result of a composition having low concentration of added hypochlorite salts at a pH between at least 12.0 and about 12.5 is a nearly HOCl free composition.

In an embodiment, the cleaning mixture is based on a nearly HOCl free composition. More specifically, the concentration of HOCl is between 0.001 ppm to 0.03 ppm, or about 0.005 ppm on the average as shown in Table 1A. The experimental discovery of this range in this extreme flat region of the dissociation curve (FIG. 4) was entirely unexpected since the common HOCl concentration used in cleaning dialysis membrane assemblies in the well-known DRS-4 method (otherwise know the beach-formaldehyde method) is about 5584 ppm or at least about 1000 ppm on the average, according to Table 1A.

TABLE 1A

| | | Effective HOCl at Different pHs | | | | | | | | | | | |
|---|---|---|---|---|---|---|---|---|---|---|---|---|---|
| pH | % HOCl | 10000 | 7500 | 5000 | 2500 | 2250 | 1000 | 750 | 500 | 400 | 300 | 200 | 100 |
| 4.0 | 99.97501 | 9997.50 | 7498.13 | 4998.75 | 2499.38 | 2249.44 | 999.75 | 749.81 | 499.88 | 399.90 | 299.93 | 199.95 | 99.98 |
| 5.0 | 99.75062 | 9975.06 | 7481.30 | 4987.53 | 2493.77 | 2244.39 | 997.51 | 748.13 | 498.75 | 399.00 | 299.25 | 199.50 | 99.75 |
| 5.5 | 99.21563 | 9921.56 | 7441.17 | 4960.78 | 2480.39 | 2232.35 | 992.16 | 744.12 | 496.08 | 396.86 | 297.65 | 198.43 | 99.22 |
| 6.0 | 97.56098 | 9756.10 | 7317.07 | 4878.05 | 2439.02 | 2195.12 | 975.61 | 731.71 | 487.80 | 390.24 | 292.68 | 195.12 | 97.56 |
| 6.5 | 92.67352 | 9267.35 | 6950.51 | 4633.68 | 2316.84 | 2085.15 | 926.74 | 695.05 | 463.37 | 370.69 | 278.02 | 185.35 | 92.67 |
| 7.0 | 80.00000 | 8000.00 | 6000.00 | 4000.00 | 2000.00 | 1800.00 | 800.00 | 600.00 | 400.00 | 320.00 | 240.00 | 160.00 | 80.00 |
| 7.5 | 55.84816 | 5584.82 | 4188.61 | 2792.41 | 1396.20 | 1256.58 | 558.48 | 418.86 | 279.24 | 223.39 | 167.54 | 111.70 | 55.85 |
| 8.0 | 28.57143 | 2857.14 | 2142.86 | 1428.57 | 714.29 | 642.86 | 285.71 | 214.29 | 142.86 | 114.29 | 85.71 | 57.14 | 28.57 |
| 8.5 | 11.22877 | 1122.88 | 842.16 | 561.44 | 280.72 | 252.65 | 112.29 | 84.22 | 56.14 | 44.92 | 33.69 | 22.46 | 11.23 |
| 9.0 | 3.84615 | 384.62 | 288.46 | 192.31 | 96.15 | 86.54 | 38.46 | 28.85 | 19.23 | 15.38 | 11.54 | 7.69 | 3.85 |
| 9.5 | 1.24911 | 124.91 | 93.68 | 62.46 | 31.23 | 28.10 | 12.49 | 9.37 | 6.25 | 5.00 | 3.75 | 2.50 | 1.25 |
| 10.0 | 0.39841 | 39.84064 | 29.88048 | 19.92032 | 9.96016 | 8.96414 | 3.98406 | 2.98805 | 1.99203 | 1.59363 | 1.19522 | 0.79681 | 0.39841 |
| 10.5 | 0.12633 | 12.63313 | 9.47485 | 6.31657 | 3.15828 | 2.84245 | 1.26331 | 0.94748 | 0.63166 | 0.50533 | 0.37899 | 0.25266 | 0.12633 |
| 11.0 | 0.03998 | 3.99840 | 2.99880 | 1.99920 | 0.99960 | 0.89964 | 0.39984 | 0.29988 | 0.19992 | 0.15994 | 0.11995 | 0.07997 | 0.03998 |
| 11.5 | 0.01265 | 1.26475 | 0.94856 | 0.63238 | 0.31619 | 0.28457 | 0.12648 | 0.09486 | 0.06324 | 0.05059 | 0.03794 | 0.02530 | 0.01265 |
| 12.0 | 0.00400 | 0.39998 | 0.29999 | 0.19999 | 0.10000 | 0.09000 | 0.04000 | 0.03000 | 0.02000 | 0.01600 | 0.01200 | 0.00800 | 0.00400 |
| 12.5 | 0.00126 | 0.12649 | 0.09487 | 0.06324 | 0.03162 | 0.02846 | 0.01265 | 0.00949 | 0.00632 | 0.00506 | 0.00379 | 0.00253 | 0.00126 |
| 13.0 | 0.00040 | 0.04000 | 0.03000 | 0.02000 | 0.01000 | 0.00900 | 0.00400 | 0.00300 | 0.00200 | 0.00160 | 0.00120 | 0.00080 | 0.00040 |
| 13.5 | 0.00013 | 0.01265 | 0.00949 | 0.00632 | 0.00316 | 0.00285 | 0.00126 | 0.00095 | 0.00063 | 0.00051 | 0.00038 | 0.00025 | 0.00013 |
| 14.0 | 0.00004 | 0.00400 | 0.00300 | 0.00200 | 0.00100 | 0.00090 | 0.00040 | 0.00030 | 0.00020 | 0.00016 | 0.00012 | 0.00008 | 0.00004 |

To better appreciate the unexpected composition of the embodiments, it is better to express the HOCl level in the compositions in parts per billion or ppb (Table 1B). In this case, acceptable concentration of HOCl in the inventive composition is in the range between 0.4 to 30 ppb or about between 0.4 and 50 ppb. This very low HOCl range can be established even in the presence of added hypochlorite salt as disclosed in embodiments.

membrane or cause stress cracking of dialyzer housing which is made from polycarbonate polymers. In practice, the level of inorganic base or total alkalinity of the use composition should be chosen to yield a pH of at least 12.0 to about 12.8, preferably at least 12.0 to 12.5, and most preferably 12.2 to 12.5 at the use concentration during cleaning.

The importance of having a nearly HOCl-free composition cannot be underestimated. Current cleaning protocols

TABLE 1B

| | | Effective HOCl at Different pHs and ppb | | | | | | |
|---|---|---|---|---|---|---|---|---|
| pH | % HOCl | 1000 | 750 | 500 | 400 | 300 | 200 | 100 |
| 4.0 | 99.97501 | 999750.06 | 749812.55 | 499875.03 | 399900.02 | 299925.02 | 199950.01 | 99975.01 |
| 5.0 | 99.75062 | 997506.23 | 748129.68 | 498753.12 | 399002.49 | 299251.87 | 199501.25 | 99750.62 |
| 5.5 | 99.21563 | 992156.32 | 744117.24 | 496078.16 | 396862.53 | 297646.89 | 198431.26 | 99215.63 |
| 6.0 | 97.56098 | 975609.76 | 731707.32 | 487804.88 | 390243.90 | 292682.93 | 195121.95 | 97560.98 |
| 6.5 | 92.67352 | 926735.15 | 695051.36 | 463367.58 | 370694.06 | 278020.55 | 185347.03 | 92673.52 |
| 7.0 | 80.00000 | 800000.00 | 600000.00 | 400000.00 | 320000.00 | 240000.00 | 160000.00 | 80000.00 |
| 7.5 | 55.84816 | 558481.56 | 418861.17 | 279240.78 | 223392.62 | 167544.47 | 111696.31 | 55848.16 |
| 8.0 | 28.57143 | 285714.29 | 214285.71 | 142857.14 | 114285.71 | 85714.29 | 57142.86 | 28571.43 |
| 8.5 | 11.22877 | 112287.71 | 84215.78 | 56143.85 | 44915.08 | 33686.31 | 22457.54 | 11228.77 |
| 9.0 | 3.84615 | 38461.54 | 28846.15 | 19230.77 | 15384.62 | 11538.46 | 7692.31 | 3846.15 |
| 9.5 | 1.24911 | 12491.11 | 9368.33 | 6245.55 | 4996.44 | 3747.33 | 2498.22 | 1249.11 |
| 10.0 | 0.39841 | 3984.06 | 2988.05 | 1992.03 | 1593.63 | 1195.22 | 796.81 | 398.41 |
| 10.5 | 0.12633 | 1263.31 | 947.48 | 631.66 | 505.33 | 378.99 | 252.66 | 126.33 |
| 11.0 | 0.03998 | 399.84 | 299.88 | 199.92 | 159.94 | 119.95 | 79.97 | 39.98 |
| 11.5 | 0.01265 | 126.48 | 94.86 | 63.24 | 50.59 | 37.94 | 25.30 | 12.65 |
| 12.0 | 0.00400 | 40.00 | 30.00 | 20.00 | 16.00 | 12.00 | 8.00 | 4.00 |
| 12.5 | 0.00126 | 12.65 | 9.49 | 6.32 | 5.06 | 3.79 | 2.53 | 1.26 |
| 13.0 | 0.00040 | 4.00 | 3.00 | 2.00 | 1.60 | 1.20 | 0.80 | 0.40 |
| 13.5 | 0.00013 | 1.26 | 0.95 | 0.63 | 0.51 | 0.38 | 0.25 | 0.13 |
| 14.0 | 0.00004 | 0.40 | 0.30 | 0.20 | 0.16 | 0.12 | 0.08 | 0.04 |

This ppb concentration range may be expanded somewhat depending on the nature of the dialysis membrane considered and should thus not be considered as an absolute value according to the teaching of embodiments. The above very small HOCl concentration is determined by both the amount of NaOCl (hypochlorite salt) added and the high concentration of caustic (total alkalinity) used to make the inventive composition. As illustrated in the Examples, this very low ppb concentration of HOCl in the compositions may further desire additional considerations to make the composition effective and safe for cleaning the PVP-containing dialysis membranes and dialysis membrane assemblies made by different manufacturers.

Based on the above relationship (Equation 1), to achieve the desired substantially HOCl-free composition, that the pH of the mixture is at least 12.0. However, if the cleaning solution is too caustic, hydroxide ion can damage the encourage optimizing the amount of HOCl (free chlorine) in solution (7500 to 10,000 ppm NaOCl is use in the DRS-4 method at pH about 8.0), as this has been considered to be desirable to create higher oxidation-reduction potential which is associated with faster disinfection rates and higher rates of breaking down organic molecules including proteins. The finding of the present embodiments that nearly HOCl-free compositions are effective at cleaning dialysis membranes is on the face of it is counterintuitive to the art that use hypochlorite.

The presence of HOCl in the solution may be responsible for initiating a cascade of chemical reactions that can lead to PVP degradation as proposed by Wienk et al., (1995). HOCl can react with PVP and proteins (substrates) to produce oxidized compounds and releases HCl which is known to lower the pH of the solution (Equation 2). In basic solutions, HOCl reacts with OH— to produce hypochlorite ion as described by Equation 3. HOCl can react with OCl— to produce .ClO and —OH radicals (Equation 4). Hydroxyl radical can react with OCl— to further produce .ClO radical (Equation 5). Further, .ClO, OCl— and OH— can react together to produce oxygen and more .OH (Equation 6). Collectively, the above reactions appear to be involved in the degradation of the PVP component of the membrane. Accordingly, a nearly-free HOCl according to embodiments would be beneficial in preventing these reactions from taking place during cleaning and thus decreasing the rate of PVP degradation and erosion from the membrane.

HOCl+substrate→substrate .O+HCl  Equation 2

HOCl+OH⁻→OCl⁻+H_2O  Equation 3

HOCl+OCl⁻→.ClO+Cl⁻+.OH  Equation 4

.OH+OCl⁻→.ClO+OH⁻  Equation 5

.OCl+OCl⁻+OH⁻→2Cl⁻+O_2+⁻OH  Equation 6

Oxidation-Reduction Potential

Generally chlorine solutions for disinfection are to be used at maximum oxidation-reduction potential (ORP) where HOCl is the dominant species. In a finding of embodiments regarding the removal of the second class of irreversibly adsorbed fouling proteins from the dialysis membrane surface and pore structure, it was found that composition with a low ORP of less than 0.5 volts to be effective and at the same time protective to the PVP content of the membrane. In this regard, we found that hydrogen peroxide and proxy-acid compositions could not clean or remove this class of serum proteins. Accordingly, we found that the clearance of the middle molecules cannot be recovered with peracetic acid which includes high concentration of hydrogen peroxide despite the high oxidation potential (standard oxidation potential is about 1.7 volts).

Figure 5:
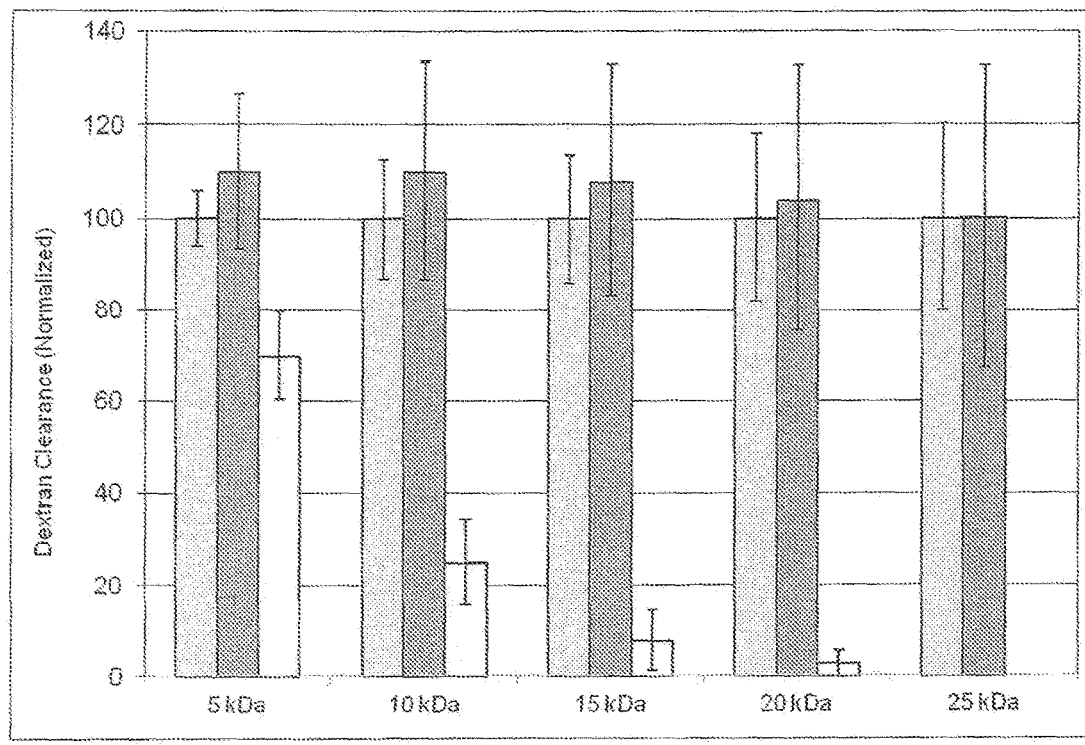
FIG. 5 is a graph showing the normalized clearance values of dextran probes of different molecular weights (5 kD, 10 kD, 15 kD, 20 kD and 25 kD) for a typical high-flux dialyzer. Three clearance values are included for each dextran molecular weight from left to right: new membrane, membrane cleaned with a composition and method of an embodiment, and membrane cleaned with conventional peracetic acid method.

FIG. 5 compares the effectiveness of cleaning with respect to restoring clearance of middle molecules of the dialyzers of prior art cleaning methods with those of embodiments. Example 1 shows a decrease in convective clearance of dextran probes with different molecular weights as a function of the reuse number when patient dialyzers are processed with the conventional peracetic acid method (See Table 4). That is the conventional prior art practices had the disadvantage of significant degradation in uremic molecule clearance particularly middle molecular weight proteins. In contrast, FIG. 5 shows a comparison of dextran probe clearance of new dialyzer (Polyflux® 17R) with dialyzers reprocessed with the inventive composition according to the treatment method embodiments. In contrast, the clearance of dextran probes of dialyzers is not recovered when processed with conventional peracetic acid (FIG. 5).

The compositions according to some embodiments have the lowest possible oxidation-reduction potential (Example 11) and nearly-free HOCl levels. According to embodiments, the hypochlorite species in an inventive composition consists almost entirely of OCl— ions as show in FIG. 4. To more appreciate this unexpected result, the concentration of HOCl of the embodiments is about 5 orders of magnitude lower than that used in the DRS-4 method, as shown in Tables 1A and 1B. Erosion of the PVP component of the membrane appears to be mostly dependent on the concentration of HOCl in the cleaning solution as supported by the data in Tables 1A and 1B. Also, the oxidation-reduction potential of hypochlorite solutions is highly dependent on the concentration of the HOCl concentration as illustrated in Example 11.

To quantitatively appreciate the low ORP arising from using nearly-free HOCl solutions where OCl⁻ is the main hypochlorite species, we consider the case of alkaline Clorox solution at pH 12.5.

The oxidation-reduction potential of alkaline Clorox solutions can be calculated as follows. Clorox is an aqueous solution of sodium hypochlorite, NaOCl, usually 6% by weight. The ORP, E, is determined by the half reaction:

ClO⁻+2OH⁻→ClO_2+H_2+2e  Equation 7

The concentration dependence of E is given by:

$E = E^0 - [RT/nF] \ln [ClO^-][OH^-]^2 = [0.059/2] \log 10[ClO^-][OH^-]^2$  Equation 8 where $E^0$ is the redox potential for the standard concentrations; F, Faraday's constant; n, the number of electrons involved in the half reaction; and T, the temperature, here taken to be 25° C.

The commercial Clorox concentration of 6% NaOCl (60 g/L) solution made at pH of 12.5 is considered. The molecular weight of NaOCl is 74.4 and it is assumed to be fully ionized in solution. The molar concentration of ClO—is: [ClO-]=60/74.4=0.81 mol/L At pH 12.5, [H+]=10-12.5, and, [OH—]=10-14/[H+]=10-1.5=3.16×10-2 mol/L. From "Oxidation Potentials", 2nd Ed., W. M. Latimer, Prentice Hall, Inc. [1956] p2, p55, E0=−0.66 Volts. [OH-]2=1×10-3 [mol/L]2

Equation 8 then becomes: E=−0.66-[0.059/2] log 10 [0.81] [1×10-3]=−0.66+0.09=−0.57 Volts. This is the ORP, E(s), for the starting solution. E(s)=−0.57 Volts.

The effect of dilution on E(s) can be calculated as follows. The ORP depends on [ClO⁻] and [OH⁻]² so let us consider two ways to dilute.

In dilution 1, both [ClO⁻] and [OH⁻] are diluted by a factor of 10. So that [ClO⁻]=0.081 mol/L and [OH⁻]=3.16× 10-3 mol/L, and [OH⁻]²=1.0×10⁻⁵ [mol/L]² so that: E(0.1)= −0.66-[059/2] log 10 [0.081][1×10-5]=−0.66+0.18=−0.48 Volts. In conclusion, the ORP, E(0.1) for a tenfold dilution of OCl⁻ is −0.48 Volts.

In a second dilution, Clorox is diluted by a factor of ten but pH is maintained at 12.5. So that [ClO⁻]=0.081 mol/L and [OH⁻]=3.16×10⁻² mol/L, [OH⁻]²=1.0×10⁻³ [mol/L]² so that: E(0.1, pH 12.5)=−0.66-[059/2] log 10 [0.081] [1×10-3]=−0.66+0.12=−0.54 Volts. In conclusion, the ORP or Redox potential, E(0.1, pH 12.5) for a tenfold dilution at pH 12.5 is −0.54 Volt. According this example, the Redox potential of the 6% NaOCl made at pH 12.5 should not be more than 0.54 Volts.

The low ORP value of less than 0.54 Volts and more preferably <0.5 Volts of the inventive composition is significantly important to protecting PVP-containing membranes from degradation. The ORP of the inventive composition is significantly lower than most hypochlorite-based dialyzer cleaning solutions such as those used in the DRS-4 method as provided in Example 11. The very low ORP properties of the inventive composition (<0.5 volts) appears to be needed for preventing PVP degradation and erosion from the dialysis membranes possibly by significantly decreasing rates of oxidation reactions with the PVP component of the membrane, both on the membrane surface and inside the pore structure. ORP of less than 0.5 Volts of the inventive composition is achieved by adjusting the level of added hypochlorite salt (50 to 1000 ppm) and the total alkalinity of the composition. According to embodiments, the ORP characteristics may be adjusted depending on the chemical composition of the dialysis membrane considered and may be in the range of 0.45 to 0.55 Volts.

This leads to yet another characteristic of the composition embodiments, namely that the oxidation-reduction potential of the composition advantageously may be about 0.5 volts or less. Since embodiments of the compositions may be nearly HOCl-free, oxidation-reduction potential of 0.5 volts or less is due to hypochlorite anion. Oxidation reduction potential (ORP) is determined according to the combination of the amount of the hypochlorite salt added and the alkalinity of the solution. The balance between the added hypochlorite and the level of alkalinity or excess alkalinity thus determines the ORP properties needed to provide sufficient protection against the degradation of PVP by oxidation. Advantageously, the hypochlorite ion under the selected alkaline condition is not a strong enough oxidant to degrade PVP but is sufficiently powerful to selectively breakdown membrane fouling proteins belonging to the second class. This threshold oxidation-reduction potential (0.5 volts) seems to be protective to the PVP present in dialysis membrane during cleaning with the inventive compositions.

About 50 to about 1,000 Ppm of a Hypochlorite Salt

Embodiments of the present compositions are also novel in that very low concentrations of hypochlorite salts are used. Preferably about 50 to about 1,000 ppm of a hypochlorite salt are used, more preferably about 100 to about 1,000 ppm of hypochlorite salt. The concentration of hypochlorite chosen for the compositions of the embodiments may be determined based on several factors.

For example, the desired ppb levels of available free chlorine is decided by the balance between the amount of added hypochlorite salt and caustic concentration (total alkalinity) and depends to a large extent on membrane composition and on how PVP is incorporated in the membrane microstructure and on its level in the membrane. It is thus desirable to select this balance to achieve cleaning of membrane surface and its pore structure without degrading other membrane properties at the same time. Too high caustic may also lead to membrane degradation or other components of the dialysis membrane assemble such as cracking of the dialyzer housing as described in the specification.

Therefore the amount of hypochlorite salt can be varied between about 100 to about 1000 ppm in order to achieve cleaning of any type of membrane, determined by such factors as the amount of PVP in the membrane, the molecular weight and distribution of the PVP component in the polymer blend and other variable process parameters which may vary depending on the manufacturing process of the hollow fiber membrane. However, the amount of hypochlorite salt used in the compositions needs to sufficient to provide high enough cleaning rates to completely remove membrane fouling proteins in no more than 10 minutes, and more preferably 5 to 7 minutes at temperatures between about 40° C. to 50° C., and more preferably between 45° C. to 50° C. at the high pH conditions of at least 12.0 to about 12.8 and more preferably about 12.2 to 12.5. All of these variations in the amount of hypochlorite salts are encompassed by embodiment, independent of the method of treatment of cleaning whether based on liquid only cleaning, or employ the gas-liquid cleaning method as described in embodiments.

Ratio of Hypochlorite Salt:Base

Another feature of embodiments of the compositions and methods is the ratio of base to hypochlorite salt. This relationship of the ratio of NaOH to NaOCl to pH and ORP is described in Table 2 which summarizes nine (9) compositions. Compositions A through F were made according to the acceptable ranges defined by the embodiment. Compositions G through I we made compare and demonstrate the existing art with the compositions of embodiments.

According to embodiments, the concentration of sodium hydroxide (NaOH) is between about 8.6 g/L to about 31.2 g/L. According to embodiments, the concentration of the hypochlorite salt (NaOCl) in the composition is between about 7.8 g/L to about 23.4 g/L. We experimentally discovered that the weight ratio between the alkali metal hydroxide and the hypochlorite salt is advantageous to describe the compositions according to an embodiment. The aforementioned above ratio between about 0.5 to about 4.0 is an acceptable range and a minimum ratio of less than 0.5 is not preferred according to embodiments. Compositions A through F having free hypochlorous acid (HOCl) between about 2.39 to about 17.99 ppb and ORP between about 376 mV to about 475 mV are within the ranges defined by the specification for effective and safe application to clean dialysis membrane assemblies without erosion of PVP.

On the other hand, compositions G through I are outside of the ranges recommended by the embodiments. For compositions G through I, the ratio between the alakali metal hydroxide (NaOH) and the hypochlorite salt (NaOCl) is between 0 and 0.02 which is much lower than the 0.5 recommended in embodiment. For these same compositions (G through I), the ORP is from about 546 mV to about 786 mV and the free hypochlorous acid concentration is in the range between 450 and 86,538 ppb. It is clear that both ORP and free hypchlorous acid for compositions G through I are outside the ranges found according to embodiments. Compositions A through F were tested to clean dialysis membrane assemblies multiple times and were found to achieve effective recovery of middle molecules without substantially affecting the PVP concentration in the membrane. On the other hand, when compositions G through I were used to clean the dialysis membrane assemblies, substantial erosion of the PVP from the membrane was found. Such compositions were deemed unacceptable for safe cleaning of PVP containing dialysis membranes as amply detailed in embodiments. Composition G was found to be marginally acceptable to clean the membrane few times only (about 13 times). This composition was found to result in the complete loss of PVP from the membrane as provided in Example 7.

In embodiments, the ratio of base:hypochlorite may be given by a number based on Table 2. It is appreciated that this ratio can also be described as a ratio of base:hypochlorite, ratio of OH:HOCl or a ratio of HOCl:OH. It is appreciated that while a ratio does not have any units per se, the ratio could be used to determine units such as %, ppm, ppb or other expression of concentration of both hypochlorite and base. It is appreciated that the phrase base, exemplary shown as OH of NaOH encompasses any source that may provide alkalinity.

TABLE 2

| Composition | A | B | C | D | E | F | G | H | I |
|---|---|---|---|---|---|---|---|---|---|
| NaOH (g/L) | 20.8 | 20.8 | 20.8 | 20.8 | 31.2 | 8.6 | 1.04 | 0 | 0 |
| NaOCl (g/L) | 7.8 | 15.6 | 23.4 | 7.8 | 7.8 | 16.9 | 58.5 | 58.5 | 195 |
| TSP (g/L)* | 16.3 | 16.3 | 16.3 | 0 | 16.3 | 16.3 | 0 | 0 | 0 |

TABLE 2-continued

| Composition | A | B | C | D | E | F | G | H | I |
|---|---|---|---|---|---|---|---|---|---|
| NaOH/NaOCl | 2.67 | 1.33 | 0.89 | 2.67 | 4.00 | 0.51 | 0.02 | 0.00 | 0.00 |
| ORP (mV) | 376 | 440 | 475 | 454 | 419 | 445 | 546 | 780 | 786 |
| pH | 12.51 | 12.51 | 12.48 | 12.5 | 12.7 | 12.16 | 11.3 | 9 | 9.6 |
| NaOCl (ppm) | 300 | 600 | 900 | 300 | 300 | 650 | 2250 | 2250 | 7500 |
| Free [HOCl] (ppm) | 0.00371 | 0.00742 | 0.01192 | 0.00379 | 0.00239 | 0.01799 | 0.45098 | 86.53846 | 74.60698 |
| Free [HOCl] (ppb) | 3.71 | 7.42 | 11.92 | 3.79 | 2.39 | 17.99 | 450.98 | 86538.46 | 74606.98 |

*Tri-sodium phosphate (TSP)

Summary of Composition

Although key elements of the composition have been discussed separately, it is appreciated that the novelty of the composition is in the combination of all of the elements in a single composition. That is, a composition having an inorganic base/s and from about 100 to 1,000 ppm of a hypochlorite salt; less than 50 ppb and more preferably less than 30 ppb, available free HOCl; base:hypochlorite ratio of at least 0.5 to about 4.0; a pH between at least 12.0 to about 12.8 and more preferably between 12.2 and 12.5; an oxidation-reduction potential of less than 0.5 volts; and a mole % of hypochlorous acid, HOCl, relative to the sum of hypochlorous acid plus hypochlorite anion, —OCl less than 0.004% hypochlorite will result in a solution that cleans many classes of fouling proteins from dialysis membranes at about 40° C. to about 55° C., and more preferably between 45° to 55° C., without harming the PVP of those membranes thus resulting in improved cleaning of membranes without harming the membrane structure.

It is appreciated that, while different elements of the compositions are interrelated, each can contribute to the novelty of the embodiments as a whole. For example, a hypochlorite salt at pH 12.0 is going to be nearly HOCl free, but not every hypochlorite solution at pH 12.0 will contain less than 30 ppb HOCl unless the composition also has about 100 to about 1000 ppm hypochlorite. Similarly, obtaining a composition having an oxidation-reduction potential of less than 0.5 volts means not only the pH to be at least 12.0 but also a specific ratio of hypochlorite ion to hydroxyl ion.

Sources of Compounds for the Composition

Suitable inorganic bases that provide alkalinity [OH⁻] include sodium hydroxide, potassium hydroxide, sodium carbonate, potassium carbonate, sodium phosphate, potassium phosphate, sodium silicates and their mixtures. One skilled in the art may expand this list to include other compounds that can adjust alkalinity. One property of the inorganic base is that it can be rinsed completely and removed from the membrane without leaving residue or adsorbed species that can be transferred to the patient during dialysis. Sodium hydroxide is a preferred inorganic base. Suitable hypochlorite salts are sodium hypochlorite, potassium hypochlorite and calcium hypochlorite. A preferred hypochlorite salt is sodium hypochlorite.

It was also found that the purity of the compounds used to make embodiments of the compositions of also can be important. It is advantageous that the starting materials be free or nearly free of transition metals to avoid catalyzing reactions with PVP or other polymers of dialysis membranes during cleaning.

Another finding of embodiments pertains to making compositions that have long shelf life for more than one year without loss in the hypochlorite content. We found that the addition of about 0.06% to about 0.2% of phosphate in the nearly HOCl-free composition results in highly a stable composition for more than one year and as long as two years as provided in the Examples 8.

Composition Concentrate

Preferably the composition embodiments can be made, stored and supplied to user as a concentrate, such as a 5×, 10×, 20×, 25×, 30×, 40× or more concentrate compared to the use concentration. Use concentration is the concentration of composition exposed to membrane. For convenience, in some embodiments a concentrate is provided that can be diluted to appropriate use concentration immediately before use. When the composition is stored as a concentrate at room temperature in an appropriate dark container that the stability and quality of the composition is retained for extended periods of time (Example 8). This is another property of the composition since commercial hypochlorite solutions are inherently unstable and are known to significantly degrade within few months.

In particularly preferred embodiments, the use concentration of hypochlorite salt in the compositions is between about 100 and about 1,000 ppm. If the composition is supplied as a 5× concentrate, then the concentrate would have 500 to 5,000 ppm and likewise a 40× concentrate would have 4,000 to 40,000 ppm. So that the range of hypochlorite salts in concentrated form would preferably be between about 500 and about 40,000 ppm. This concentration can be easily expressed as either ppm or % by weight using the following:

$$1\% = 1/100$$

$$1 \text{ ppm} = 1/1000000$$

So, 1 ppm=0.0001%

So to convert from ppm to percent, divide the ppm by 10000:

$$x(\%) = x(\text{ppm})/10000$$

So a composition having a range of hypochlorite salts from 500 to 40,000 ppm is equivalent to 0.05% to about 4%.

It can be appreciated that while composition concentrate of 2×, 5×, 10×, 20×, 25×, 30×, 40× are suggested above, they are merely illustrative of the larger inventive embodiment of making any concentrate of the compositions, from 2× to 250× or greater. Embodiments may encompass any cleaning composition concentrate effective for cleaning PVP-containing dialysis membrane assembly without substantial erosion of PVP provided that when the concentrate is diluted to in-use concentration, the composition has the following characteristics: from about 100 to about 1,000 ppm of a hypochlorite salt, less than 50 ppb free HOCl, a pH of from at least pH 12.0 to about 12.8, an oxidation-reduction potential less than 0.5 volts, a mole % of hypochlorous acid, HOCl, relative to the sum of hypochlorous acid plus hypochlorite anion, —OCl of less than 0.004%, and a ratio of base:hypochlorite of at least 0.5. Specifically, this cleaning composition concentrate comprises: from about 0.05% to about 4% by weight of a hypochlorite salt; an alkali metal hydroxide to provide alkalinity; from about 0.5% to about 20% by weight of an alkali metal salt of phosphate; and the balance being water. It is appreciated that the pH of the concentrate will be determined as that which will obtain the proper pH upon dilution. It is likely therefore that the pH of the concentrate may be greater than pH 12.8 and of course would be within the scope of some embodiments.

Salts

Figure 6:
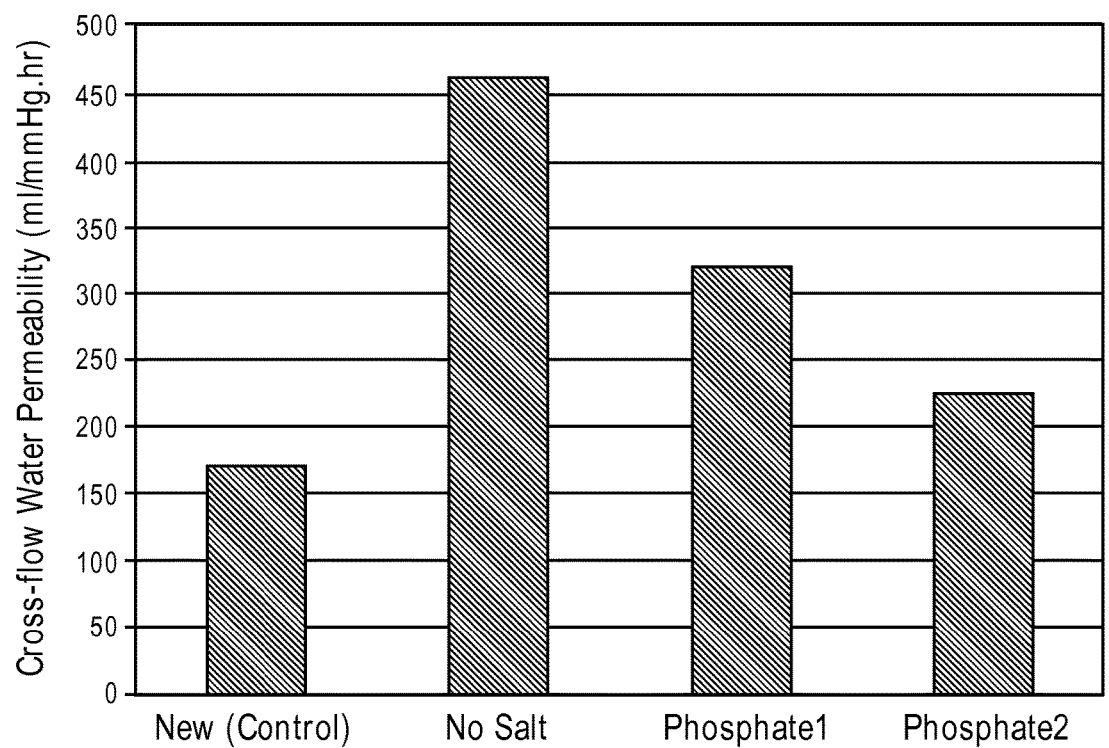
FIG. 6 is a graph showing the cross flow water permeability (Lp) of a Fresenius Optiflux® 200A dialyzer after twenty (20) simulated cleaning cycles with three compositions in the presence of a hypochlorite salt (500 ppm) with and without the addition of a phosphate salt. Composition 1 (entitled no salt) was made at 500 ppm hypochlorite at pH 12.3 without phosphate salt. Composition 2 (entitled phosphate 1) was made at 500 ppm hypochlorite at pH 12.3 with the addition of 0.1% tri-sodium phosphate. Composition 3 (entitled phosphate 2) was made at 500 ppm hypochlorite salt at pH 12.3 with the addition of 0.3% tri-sodium phosphate.
Figure 7:
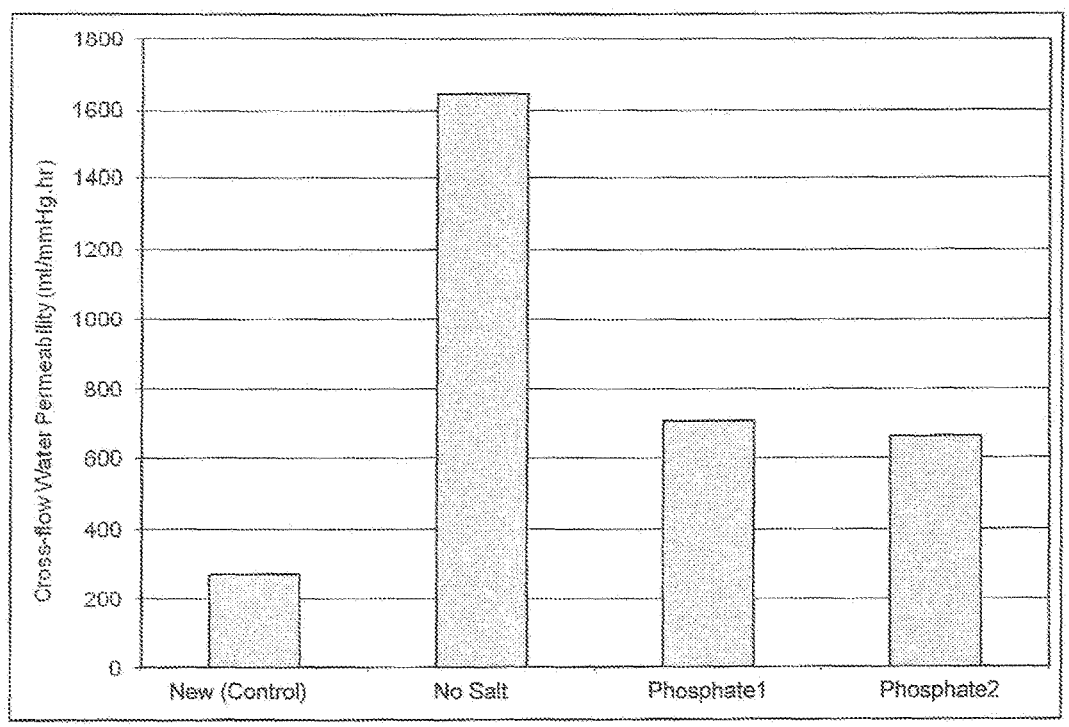
FIG. 7 is a graph showing the cross flow water permeability (Lp) of an Asahi APS® 21R dialyzer after twenty (20) simulated cleaning cycles with the composition of an embodiment made in the presence of a hypochlorite salt (500 ppm) and with the addition of a phosphate salt. Composition 1 (entitled no salt) was made at 500 ppm hypochlorite at pH 12.3 without phosphate salt. Composition 2 (entitled phosphate 1) was made at 500 ppm hypochlorite at pH 12.3 with the addition of 0.1% tri-sodium phosphate. Composition 3 (entitled phosphate 2) was made at 500 ppm hypochlorite salt at pH 12.3 with the addition of 0.3% tri-sodium phosphate. This figure demonstrates the effect of the phosphate salt concentration on preserving the permeability characteristics of the dialysis membrane.

It has been found that PVP-containing hemodialysis membranes from different manufacturers can exhibit different levels of resistance to hypochorite-based cleaning compositions in some embodiments even when the % HOCl is substantially zero. Some composite hollow fiber filter membranes that include PVP and PES (or PS) blends have been found to be much more sensitive to degradation than others. So a further embodiment pertains to further protection of the membrane against degradation by hypochlorite, as it pertains to both the membrane surface and the internal surfaces and size distribution of the pore structure, by including additional inorganic or water-soluble salts of lower organic acids in the inventive composition. The inclusion of salts notably those which include multivalent anions such as phosphate can further protect the membrane and decrease the rate of hypochlorite attack on the membrane as shown in FIGS. 6 and 7. Based on our findings, the role of salts in the composition may be related to a physical function due the ionic charge of the anion, there may also be some form of specific binding or interaction between the added salts and the reactive sites in the membrane. These findings indicate that the added salts, especially phosphate, may provide additional protection of the membrane possibly by two mechanisms: one is due to the increasing the ionic strength and the other may be due unknown specific binding to some reactive sites on the membrane surface or inside its pore structure. Salts that provide additional alkalinity such as phosphates are also preferred.

In a related embodiment, salts of some water-soluble lower aromatic acids notably benzoate and salicylate seem to possess some protection of the membrane surface and pore structure during cleaning with the inventive composition. It is not clear however as to the mechanisms of this protection. This may be related to some slight physical adsorption on the membrane surface due to some hydrophobic bonding of the organic moiety of these compounds during the cleaning step.

It is likely these ionic compounds may competitively bind to the PVP constituent of the membrane or some related reactive sites and reduce interaction with hypochlorite species in the composition. In addition, there may also be specific interactions or binding of these ionic components with surface PVP in the membrane layer and within the pore structure that provide some protection against its chemical degradation or physical erosion.

Particularly useful protection agents include salts of di- and trivalent anions such as phosphate and citrate, and to a lesser degree sulfates, and salts containing a phenyl groups such as benzoates and salicylates, and mixtures thereof. Sodium phosphate and potassium phosphate are especially suitable.

We further experimentally discovered that the addition of certain inorganic anions to the nearly hypochlorous acid-free high pH (high alkalinity) composition to further impart more protection to PVP-containing dialysis membranes. These unexpected results allowed us to formulate compositions to protect the most sensitive PVP-containing dialysis membranes and prevent their damage during processing/cleaning as provided in FIGS. 6 and 7. According to an embodiment, two main classes of additives were found to further protect the PVP-based dialysis membranes. The first is based on inorganic anions and preferably those which are multivalent such as phosphate. The second is based on salts of some lower aromatic acids such as benzoates and salicylates which are very soluble in water and have very low propensity to adsorb on the dialysis membrane. Phosphate appears to be especially useful compared to other anions. It appears that there may be an additional benefit to phosphate ion beyond its role in competitive electrostatic interactions as mentioned earlier in this disclosure. Measuring the cross flow water permeability of the dialyzer after multiple treatments with the intended compositions allowed us to further define the preferred compositions as described in FIGS. 6 and 7.

In this manner, the salts added to the compositions can be considered as ionic protecting agents. The concentration of the ionic protecting agents should be between 0.1% to 1%, preferably 0.1% to 0.5%, and most preferably 0.2% to 0.5% by weight of the composition. More examples of the ionic protection effect will now be described.

Our testing demonstrates improved retention of cross-flow permeability when a phosphate salt is added to the composition. This effect was seen in two different types of hemodialyzers: A) Asahi APS® 21R dialyzer; B) Fresenius Optiflux® 200A dialyzer.

FIG. 6 demonstrates improved retention of cross-flow permeability after 20 simulated cleaning cycles of a Fresenius Optiflux® 200A dialyzer using a composition of 500 ppm hypochlorite added salt at pH 12.2 in the presence of no salt, sodium phosphate tribasic ("phosphate 1") and ("phosphate 2").

FIG. 7 demonstrates improved retention of cross-flow permeability after 20 simulated cleaning cycles of an Asahi APS® 21R dialyzer using a composition of 500 ppm hypochlorite at pH 12.3 in the absence of tri-sodium phosphate, and in the presence of two concentrations of tri-sodium phosphate.

It can now be appreciated that while we have obtained a composition useful for cleaning hemodialysis membranes, the salts of the composition may be altered to optimize the cleaning of a particular membrane and may be encompassed by embodiments. Such variables have been amply described and explained in the present specification.

Two additional features of the use of the composition embodiments are the application of composition at a temperature of about 40° C. to about 55° C. and limiting the duration of cleaning to less than 10 minutes, more preferably 5-10 minutes, and even more preferably 5 to 7 minutes, during each cleaning cycle. These features will be discussed in greater detail in the description of the methods.

Compositions and the PVP Component of Membranes

The composition embodiments may be useful in cleaning and regenerating all dialysis membranes that contain PVP as a part of the polymer blend, regardless of manufacturer or type and cover the cleaning of both low and high flux dialyzers. The effectiveness and safety of the inventive cleaning compositions and methods according are demonstrated in several types of dialyzers.

The composition embodiments were found to be surprisingly excellent at cleaning PVP-containing membranes, and should also be safe to clean membranes based on PES, PS, polyamide or related polymers and blends made without PVP.

Yet according to another embodiment, the reactions that take place during cleaning of the inventive composition with residual fouling proteins, either present on the surface of the membrane, also sometimes called the protein layer, or in the pore structure do not affect the PVP component of the membrane or cause its loss at significant levels. The divergence in reactivity of the instant composition with membrane fouling proteins and with PVP is a major finding that allows achieving effective cleaning without causing erosion of PVP component from the dialysis membrane. In other words, the rate of removing membrane fouling proteins is high enough to achieve effective cleaning while the rate of attack on the PVP component is too low to degrade the function of the dialysis membrane, even after 40 or more cleaning cycles (one cycle after each dialysis treatment). The nearly HOCl-free composition is formulated to achieve the intended result by preferentially breaking down fouling proteins but not the PVP component of the dialysis membrane. The contrast, the difference between embodiments and the commonly practiced method used in DRS-4 may be due to the nearly HOCl-free properties and to the low oxidation-reduction potential of the inventive composition. In DRS-4, commercial un-buffered bleach is used at pH about 8.5 at high hypochlorite salt concentration between 5,000 and 10,000 ppm. In this pH range (about 7.5 to 9.0), high concentration of free HOCl in the solution aggressively and indiscriminately reacts with the proteins and with the PVP component of the membrane resulting in its erosion from the membrane.

Figure 2:
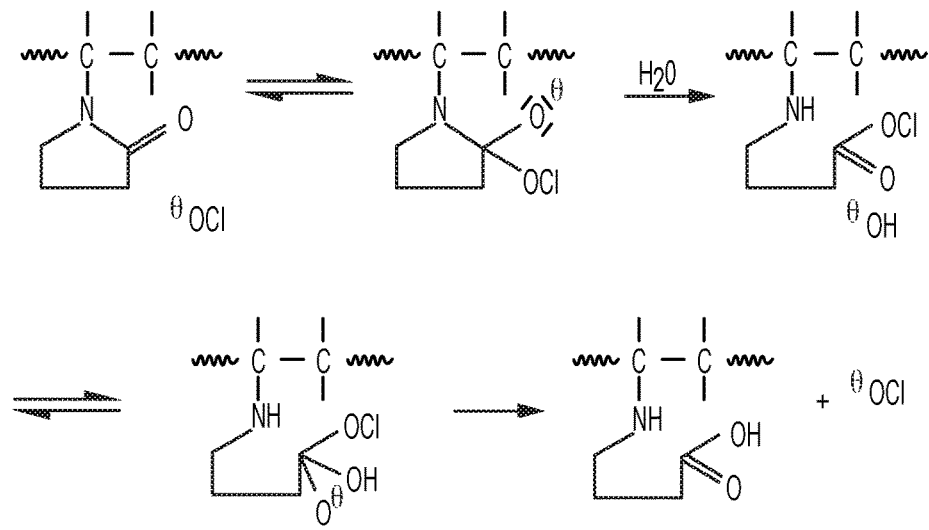
FIG. 2 includes the two reaction schemes involved in the degradation of polyvinylpyrrolidone (PVP) polymer with hypochlorite according to Weink et al (1995).
Figure 2:
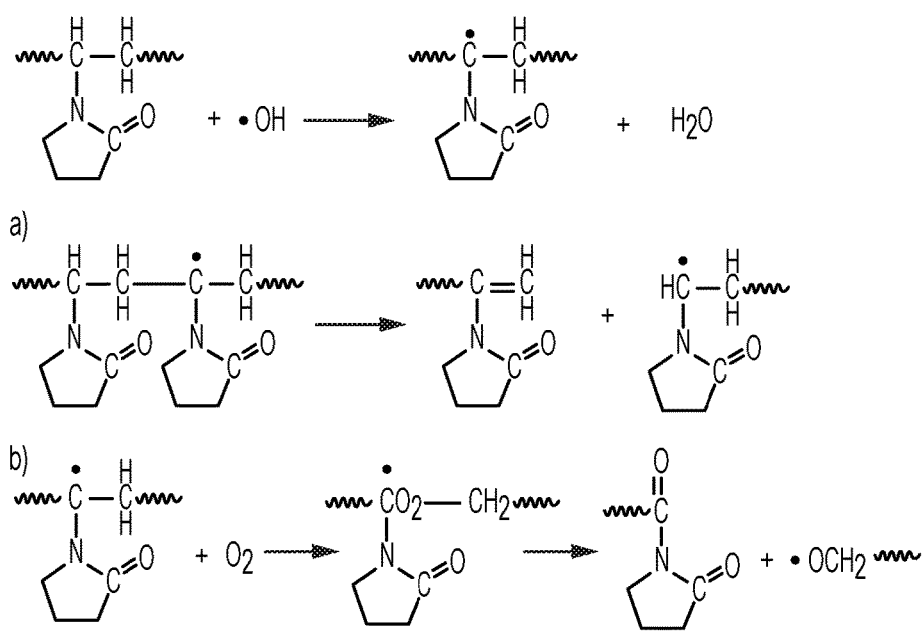

In yet another embodiment, the high concentration of caustic and other ingredients that increase alkalinity in the composition may satisfy two functions. Increasing the pH to 12.2-12.5 which ensures that the solution is nearly HOCl$^-$ free, and that OCl$^-$ is the main hypochlorite ion present in the composition which in turn ensures low oxidation-reduction potential of 0.5 volts or less during cleaning. This low ORP likely decreases oxidation rates of the composition with PVP as illustrated by the reaction schemes of FIG. 2. We suppose that the high alkalinity and high ionic strength of the composition decrease the reaction rates with the PVP component of the membrane. We hypothesize that the high ionic strength of the composition further leads to a thin double layer thickness at the surface of the membrane and this further suppresses the reaction rates at the surface of the dialysis membrane. The high ionic strength also effects high concentration of competing ions in the double layer and thus further decreases the reaction rates with PVP during cleaning by an additional mechanism. Specifically, the high concentration of hydroxyl ion in the double layer may minimize or diminish rates of reaction between OCl$^-$ and OH$^-$ and their free radicals and the membrane surface including the internal surfaces of the pore structure. It is thus possible that increasing the ionic strength and increasing the concentration of OH$^-$ (alkalinity) in the electric double layer may offer further protection against attack by reactive hypochlorite species and free radicals on the membrane material.

In an embodiment, the level and proportion (ratio) of hypochlorous acid and hypochlorite anion are critical variables in achieving effective cleaning of dialysis membrane assemblies to restore their original porosity level and pore size distribution to the original baseline state without significantly degrading the PVP-based hollow fiber hemodialysis membrane, either chemically or physically. Effective cleaning means that there is no essential loss of the intrinsic ultrafiltration flux or the sieving properties of the membrane with respect uremic middle molecules clearance and specifically without causing an increase in the original effective molecular weight cut-off specifications of the membrane. This pore size may leads albumin loss from patient during dialysis as in the case of DRS-4 method described in the specification. The effective cleaning process has been found to be primarily controlled by the amount of hypochlorite salt, the ratio of hypochlorous acid or available free chlorine to hypochlorite anion, the pH and total alkalinity of the mixture, the oxidation potential of the solution, the temperature and time of treatment and the manner of the treatment method.

We also found that using commercial hypochlorite solution as practiced in the bleach-formaldehyde DRS-4 method (pH 7.5 to 9.0) to largely remove the entire PVP content of the membrane and to render it very porous resulting in unacceptable albumin loss from patients during dialysis as reported by Kaplan et al., 1995. In Example 7, XPS testing of the PVP content of some membranes after treatment with hypochlorite solution even at pH 11.3 showed a complete removal of all the PVP from the membrane after a small number of cleaning cycles. This complete loss of PVP indicated that event pH 11.3 is not sufficient to provide protection of the dialysis membrane since this may lead to albumin loss and compromise of hemocompatibility. These findings thus indicate that raising the alkalinity of hypochlorite salt solutions even to pH 11.3 is insufficient to protect the erosion of the PVP of dialysis membranes. This example demonstrates that it is not sufficient to operate in the flat portion of the hypochlorite ionization curve (FIG. 4) for example at pH 11.3 but to operate in the extreme right at higher pH of 12.2 to 12.5 to achieve the nearly HOCl-free condition needed for safe cleaning of PVP-containing membranes.

We then found that in embodiments that compositions with almost hypochlorous acid-free levels provide near appropriate conditions when applied at pH about 12.2 to 12.5 and temperature between about 40° C. to about 55° C. to achieve the desired outcome, namely they provide effective cleaning of the membrane surface and pore structure without appreciable loss of the PVP component of the membrane. This means we are able to recover the sieving properties of the membrane and restore the clearance of middle molecules without adversely causing damage to the membrane even after 60 or more cleaning cycles, one cleaning cycle after each dialysis treatment. More surprisingly was the finding that even at very low levels (0.5 to 30 ppb) of hypochlorous acid in the mixture, the proportion of ingredients of the compositions are desirable and/or critical to achieving the above desired results. We also found that dialysis membranes made by different manufacturers use different forms of PVP and that the physical distribution of PVP within the membrane structure is also different among different manufacturers. This experimental discovery demanded that some adjustments in the compositions and treatment methods within the scope of various embodiments may be needed to address the cleaning of dialysis membranes made by different manufacturers.

Surfactants

In an embodiment, the nearly HOCl-free cleaning composition was found to react with membrane fouling proteins to produce amphiphilic protein fragments that lower the surface tension of the cleaning mixture during cleaning and that such protein fragments act as surfactants. This in-situ production of protein fragments that lower the surface tension of the solution during cleaning appears to further facilitate effective cleaning of the dialysis membrane and eliminate the need to add external organic surfactants in the instant composition. The reaction between the cleaning composition and membrane fouling proteins also facilitates the formation of bubbles, during cleaning with the gas-liquid treatment method and these bubbles act as collectors for other proteins which further increase the cleaning rates. This unexpected finding made it possible to formulate compositions from inorganic compounds only, and thus eliminated the risk that might arise from adding external organic surfactants. This finding is considered important since organic surfactant, if used, may irreversibly adsorb on the membrane and then be released into patient's blood during dialysis causing unknown health risks to the patient. Given this data it is preferred that the compositions are surfactant free.

Optional Ingredients

Builders or sequestering agents can also be optionally employed to make the inventive composition. These agents act by sequestering calcium and other di- and polyvalent metal ions, including transition metals. Examples of suitable builders/sequestering agents include complex phosphates such as sodium tripolyphosphate (STP) or tetrasodium pyrophosphate (TSPP) or their mixtures; EDTA or other organic chelating agents; polycarboxylates including citrates, and low molecular weight polyacrylates and acrylate-maleate copolymers.

Composition/Gas

The cleaning compositions according to embodiments may be defined according the method of treating the dialysis membrane assembly. For the static and liquid cleaning treatment methods, the composition is defined as the nearly HOCl-free compositions with the adjustment of pH and alkalinity and with the addition of the specific inorganic salts as provided in the specification. Compositions involving the use of gas-liquid mixture can be defined with the proportions of the liquid and gas fractions in the mixture where the liquid is based on the nearly HOCl-free composition as disclosed in embodiments.

The novel composition results in the removal of membrane fouling proteins from the surface and pore structure of the dialysis membrane In another embodiment, the nearly HOCl-free instant composition reacts with membrane fouling proteins that adhere, deposit on the membrane surface and clog the membrane pore structure resulting in their breakdown and removal from the dialysis membrane. These reactions combined with the removal of such proteins lead to the restoration of the sieving properties of the membrane and accordingly to the recovery of the convective clearance of uremic middle molecules during dialysis, a process which takes place because of liquid flow through the membrane due to ultrafiltration during dialysis. The presence of hypochlorite salt in the instant composition even at very low concentrations is needed to perform this function since compositions made at high pH alone (without hypochlorite salt) or those based on peracetic acid cannot achieve this effective cleaning of the dialysis membrane. According to this embodiment, the intended cleaning compositions in combination with the treatment parameters are together needed to provide effective breakdown and removal of the proteins that clog the pores of the membrane without degrading the membrane properties. Hence the nearly HOCl-free compositions as disclosed in the embodiments may be advantageous to perform this cleaning function and may be intended to be applied according to the treatment methods disclosed herein.

A further embodiment deals with maintaining the baseline of the pore size distribution of the dialysis membrane after each cleaning for as many as 60 or more dialysis treatments. In the DRS-4 method which employs 0.5 to 1.0% commercial hypochlorite solution to clean the dialyzers without pH adjustment, the pore size distribution of the membrane degrades very quickly leading to albumin loss from patients during dialysis and this limits the number of times a dialyzer can be used to as low as 5 to 6 depending on the membrane composition. Furthermore, the use of high concentration of un-buffered commercial bleach cannot be used universally to clean all dialysis membranes used in the field and is limited to possible one membrane type. In this case, the treatment of the membrane with high concentration of HOCl as in the bleach-formaldehyde method (DRS-4) increases the pore size and shifts its distribution very much to permit loss of albumin (66 kD) during dialysis. In contrast, the combination of the compositions and treatment methods of the embodiments can maintain the desired pore size distribution at nearly its baseline level without causing albumin loss during dialysis or other adverse effect on the hemocompatibility of the dialyzer. According to embodiments, the cleaning compositions and methods selectively maintain the desired the pore size distribution of the dialysis membrane and its hemocompatibility even after many uses as described in the specification.

Methods of Cleaning Hemodialyzers

This embodiment is illustrated by way of the following non-limiting examples which include a description of the methods used to evaluate cleaning performance and potential for membrane damage.

Generally, the methods of the present embodiment encompass application of the above described compositions to hemodialyzers and will now be described in detail.

Figure 8:
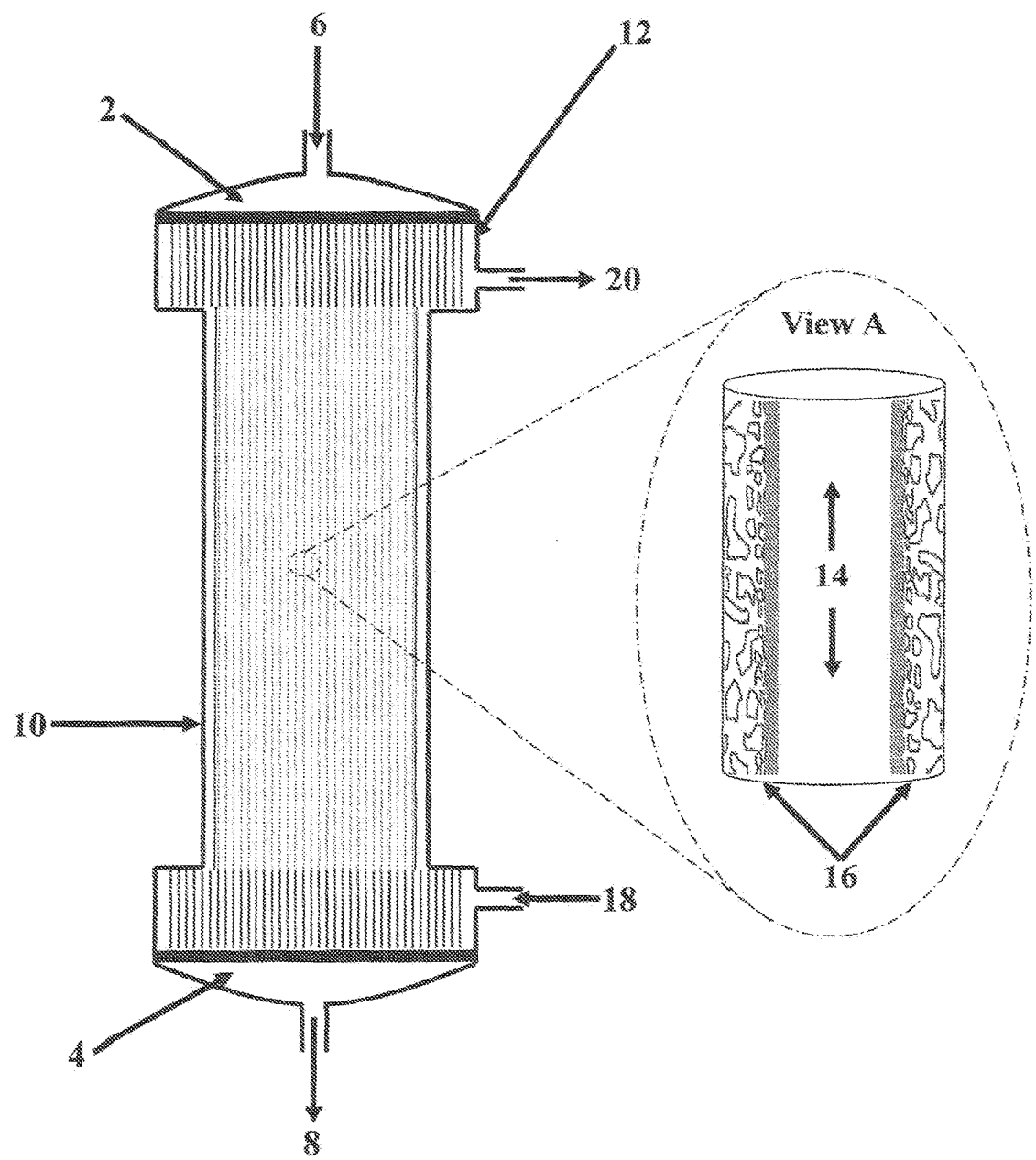
FIG. 8 is a schematic of a typical dialysis membrane assembly (dialyzer) 12 depicting its components as follows: inlet header 2 and outlet header 4 having blood inlet 6 and blood outlet 8 tubes. Headers 2, 4 are affixed to a cylindrical housing 10. In operation, the inlet 2 and outlet 4 headers channel patient's blood through a plurality of semi-permeable membrane hollow fibers, shown in exploded view A. Each hollow fiber consists of a lumen 14 and a porous membrane wall 16. Housing 10 includes a dialysate inlet tube 18 and a dialysate outlet tube 20 which allows dialysate to enter and bath the space surrounding the hollow fibers during dialysis.

FIG. 8 is a schematic of a typical dialysis membrane assembly (dialyzer) 12 depicting its components as follows: inlet header 2 and outlet header 4 having blood inlet 6 and blood outlet 8 tubes. Headers 2, 4 are affixed to a cylindrical housing 10. In operation, the inlet 2 and outlet 4 headers channel patient's blood through a plurality of semi-permeable membrane hollow fibers, shown in exploded view A. Each hollow fiber consists of a lumen 14 and a porous membrane wall 16. Housing 10 includes a dialysate inlet tube 18 and a dialysate outlet tube 20 which allows dialysate to enter and bath the space surrounding the hollow fibers during dialysis.

According to the present embodiment, three treatment methods can be employed in combination of the inventive composition to clean the hemodialyzers: static contact, liquid backflow or backfiltration and two-phase treatment. These modes of treatment can be used individually or in combination to achieve the desired cleaning results. For example a static treatment can be followed by back-flow or a combination of liquid backfiltration and two-phase treatment can be used.

The cleaning treatment can also employ various instruments to monitor variables such as solution conductivity, ORP, pH, hypochlorite concentration, pressures, temperature, and flow rates. Delivery devices to add and proportion the inventive composition concentrate during the course of cleaning and processing the dialyzers and considered as a part of the embodiment. The methods of the present embodiment can encompass both manual cleaning methods and/or automated processing systems.

Static Contact

In the "static treatment", the dialyzer assembly is filled with the cleaning mixture, normally with the aid of a pump at the use concentration, allowed to stand quiescently without flow for 5 to 10 minutes or longer, and then rinsed with RO water to remove residual cleaning mixture. The next steps of processing the dialyzer include measuring TCV and testing for fiber leaks. Afterwards, the dialyzer is filled with a designated disinfectant such as peracetic acid and then allowed to dwell for a specified period of time to achieve high-level disinfection before treating patients. This method is generally used as a pretreatment step during manual or during semi-automated processing of dialyzers.

Liquid Backflow or Backfiltration

In "liquid back-flow or backfiltration method": for high flux dialyzer, the blood outlet tube 8 and the dialysate inlet tube 18 are closed. The cleaning mixture at the use concentration as described in the embodiment can be pumped under pressure through the dialysate outlet tube 20. The cleaning mixture back-flows from the dialysate side to the blood side of the dialyzer through the membrane and then exits the assembly through the blood inlet tube 6 or 8. Additional fluid manipulation steps can be employed to ensure that all dialyzer surfaces are addressed during treatment to achieve effective cleaning of dialyzer, for example according to current art of dialyzer processing. For low flux dialyzers the composition at the recommended use concentration can be directed to flow through the lumen side of the dialyzer with periodically reversing the direction of flow.

The liquid flow rate during the backfiltration method is typically 250 to 600 ml/min, more preferably 300 to 500 ml/min which can be performed with the aid of a positive displacement metering pump, or by using negative pressure with the aid of a jet pump. The solution is heated to maintain the desired temperature at about 40° C. to about 55° C. during the treatment. One skilled in the art can determine the time needed to obtain the desired result as defined in the present in embodiment. The dialyzer is then rinsed with RO water, followed by measuring TCV and testing for fiber leaks. The dialyzer is then filled with a high-level disinfecting solution such as peracetic acid and allowed to dwell for the desired time before using to treat patients. During back-flow cleaning, the direction of flow can be periodically reversed to help dislodge blood clots for the headers and/or periodically pulsed.

Two-Phase Treatment

In "two-phase treatment", gas-liquid treatment or two-phase flow, the liquid cleaning composition is pumped through the dialysis membrane assembly as described above under liquid back-flow configuration. Simultaneously, a suitable gas, generally HEPA-filtered compressed air, is swept under pressure through the blood outlet tube 8 and exits the dialyzer through the blood inlet tube 6 and the direction of air is reversed periodically. As described in U.S. Pat. Nos. 6,945,257 and 7,367,346 incorporated by reference herein, the air creates a two-phase flow mixture inside the hollow fibers which increases the efficiency of the cleaning process, remover header clots and eliminates the need for manual intervention during dialyzer processing.

Typically, the flow rate of the gas is between 90 to 120 liters per minute at standard condition for temperature and pressure (STP) and more preferably at 72 to 100 liters/minute at STP. The volumetric flow rate of the gas can readily be controlled by suitable pressure regulators and flow controllers. The cleaning liquid fraction used to make the gas-liquid mixture comprises the compositions as detailed in the present embodiment. The liquid flow rates used to make gas-liquid cleaning mixture is about 200 to 600 ml/minute and preferably between 250 and 500 ml/minute and is supplied by back-filtration from the dialysate side into the lumen side of the high-flux dialyzer using a positive displacement metering pump system at about 40° C. to about 55° C. The gas-liquid mixture is formed in situ in the blood compartment of the dialyzer by mixing the back-filtered cleaning composition with the gas introduced into the lumen side of the dialyzer. The direction of gas flow is reversed periodically several times during cleaning to ensure that the dialyzer is uniformly cleaned during 5 to 7 minutes. The gas-liquid treatment method is effective in cleaning high-flux PES-based dialysis membranes that include PVP as detailed in the specification. In order to clean low-flux dialysis membrane assemblies that include PVP, some of the liquid cleaning composition may be provided by backfiltration and is mostly introduced by direct mixing with the gas introduced in the lumen side of the dialyzer, as described in U.S. Pat. Nos. 6,945,257 and 7,367,346, incorporated by reference herein.

The dialyzer is then rinsed with reverse osmosis (RO) water to remove residual cleaning mixture, followed by measuring TCV and testing for fiber leaks. The dialyzer is then filled with a high-level disinfectant and allowed to dwell for the desired time to achieve high-level disinfection before using it in dialysis treatment.

Time of Exposure to Cleaning Composition

Protection of dialysis membrane surface including its pore size distribution against degradation upon exposure to the inventive composition is made possible by controlling the parameters of treatment method. To assess the effect of HOCl (used as a disinfectant) on the integrity of membranes, the water treatment industry employs an index called CT. "CT" is the product of exposure time of membrane (T) and the concentration of free chlorine (HOCl) in the water, C. The cumulative CT index (termed $\Sigma$CT) is used by manufacturers to specify the expected life of the membrane based on how long the membrane is exposed to free chlorine and at what concentration. The compositions and methods of the present embodiment may provide very low $\Sigma$CT to allow successful use of the dialysis membrane for many treatments without degradation of its clearance performance, hemocompatibility or causing albumin loss during the dialysis treatment.

Table 3 provides a comparison of CT of the present embodiment with the method employed in DRS-4. The method of the present embodiment can limit the exposure time of the membrane to the cleaning composition to about 5-7 minutes per cleaning cycle and controls the HOCl concentration to 0.5 to 50 ppb as described in the specification. As demonstrated in Table 3, the $\Sigma$CT according to present embodiment is about 100,000 time less than what is practiced in the DRS-4 method. According to the present embodiment, the very small $\Sigma$CT allows the membrane to be reused at least 60 or more times without any significant change in its properties, specifically with respect to its effectiveness in the clearance of uremic middle molecules and in the prevention of albumin loss or deterioration of hemocompatibility properties of the dialyzer.

TABLE 3

| Prior Art @ 7500 ppm and pH 8.0 | | Composition A @ 500 ppm and pH 12.5 | | Ratio of Prior Art/Composition |
|---|---|---|---|---|
| [HOCl], C. | $\Sigma$CT | [HOCl], C. | $\Sigma$CT | A |
| 2142 ppm | 6.0E+5 ppm · min | 0.00632 ppm | 1.77 ppm · min | 3.39E+5 |

Time and Temperature of Cleaning Composition

Figure 9:
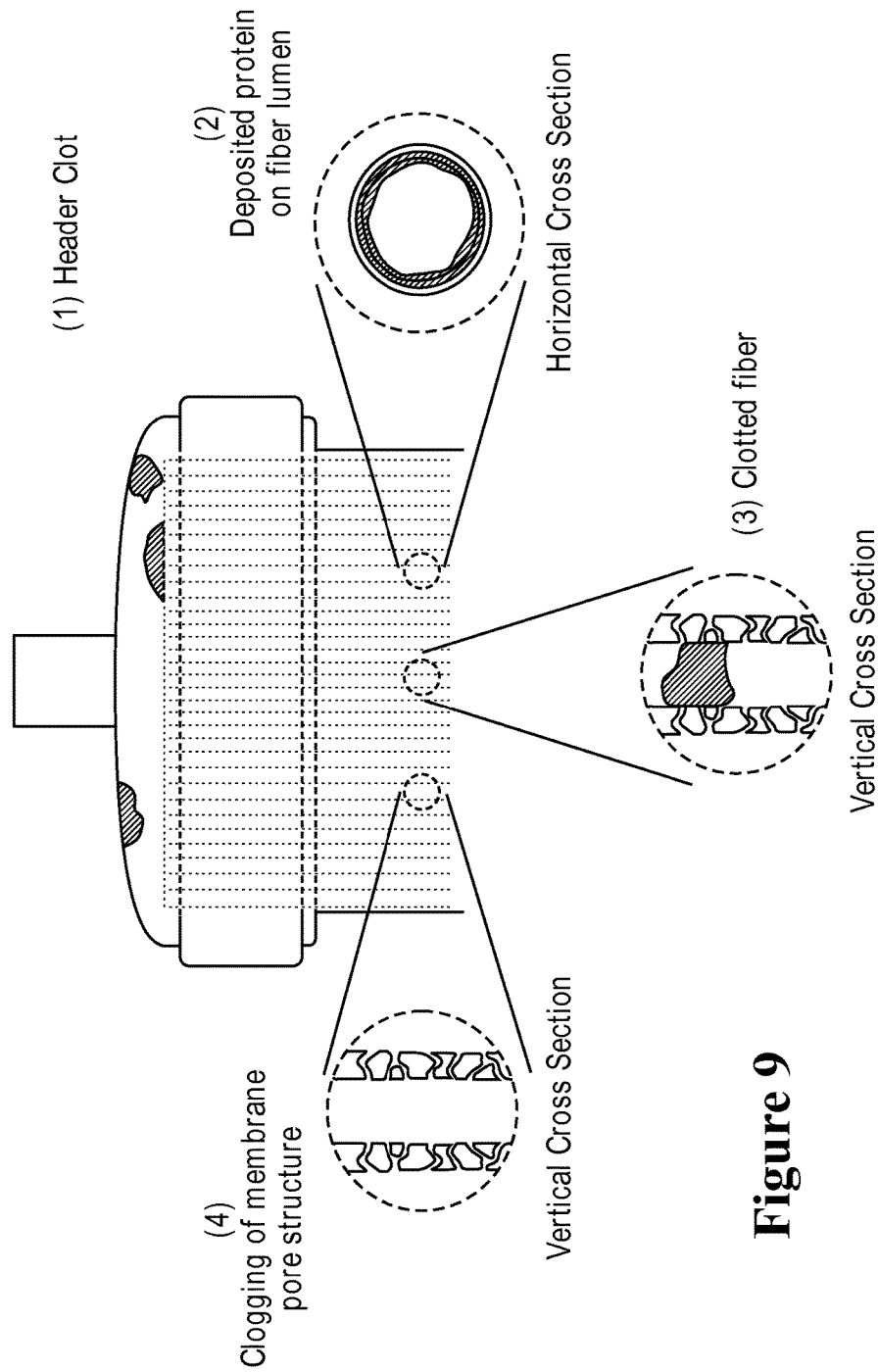
FIG. 9 depicts the modes and distribution of residual clots and proteins remaining in the dialyzer after dialysis treatment. Four modes of contamination/fouling are shown as follows: (1) header clots; (2) deposited protein on fiber lumen; (3) clotted fiber; (4) clogging of the membrane pore structure with protein.

Yet another embodiment of the invention deals with the preferred cleaning methods and treatment conditions. After dialysis, the membrane becomes fouled with serum proteins and blood clots as illustrated in FIG. 9. Proteins deposit on the surface of the membrane and inside its pore structure. The total time used in cleaning according to this embodiment of the invention is made short enough, only about 5-7 minutes per cleaning cycle, to allow the removal of fouling proteins while minimizing contact time between the bare surfaces of the membrane and the cleaning composition. The inventive methods are tailored to removing the two classes of membrane fouling proteins during approximately 80 percent of the exposure cleaning time, and hence the time fraction (about 20%) when the bare membrane surface may contact the cleaning composition is kept as short as possible.

It has been found that in order to achieve the most effective and efficient cleaning within 5-7 minutes according to the present embodiment, the temperature of the cleaning mixture should be at least about 40° C. However, the temperature of the cleaning mixture advantageously does not exceed about 55° C. to avoid damage to the membrane or other parts of the dialyzer including its housing or potting resin. According to the embodiment, the cleaning temperature can be adjusted in the range between about 40° C. to about 55° C. and the cleaning time can be kept very short to about 5 to 7 minutes per cleaning cycle. According to a preferred treatment method, the chemical action of the inventive composition is directly used to complete the reaction with membrane fouling proteins with minimal exposure of the bare membrane surface to the cleaning composition. It is important to note that the compositions of the present embodiment may have low cleaning rates if applied at room temperature of about 25° C. and it is not practical to clean the dialyzer at this low temperature since it will take a long time to complete. The rate of cleaning increases by increasing the treatment temperature which follows the Arrhenius rule where the reaction rates doubles for each 10° C. increase in temperature. According to the current embodiment, treatment temperature of about 40° C. to about 55° C. is advantageous to complete the cleaning of the dialysis membrane in 5-7 minutes. These conditions were found to be sufficient to achieve complete cleaning of the dialyzer while minimizing the degradation of the membrane itself, especially with respect to reactions with the PVP in the membrane. Hence, control of the treatment parameters including temperature and contact time during cleaning are needed when using the compositions disclosed in this embodiment.

The inventive methods and compositions are made to remove the membrane fouling proteins while at the same time minimizing reactions with the membrane material, notably the PVP component and possibly other components of the polymer blend used to make the membrane. This is made possible by using nearly HOCl-free composition, high pH (alkalinity), low oxidation-reduction potential less than 0.5 volts and the use of inorganic salts like phosphate as described earlier in the specification.

A Cleaning Protocol

The methods of the embodiment may call for using the fastest processes to complete the reaction of cleaning composition with membrane fouling proteins accumulated on the surface and in the pore structure for the purpose of effectively removing them as quickly as possible within may be 5-7 minutes or less. This can be achieved by backfiltration where the cleaning composition, heated to about 40° C. to about 55° C., is introduced from the dialysate side of the membrane assembly as described above. The rate of removing the degraded proteins can be made faster by the use of the gas-liquid method where a large number of volume exchanges with the gas-liquid cleaning mixture of the blood compartment of the dialyzer can be accomplished in 5-7 minutes during cleaning. As soon as the cleaning is finished, the membrane is immediately rinsed with RO water to remove any residual cleaning composition form the surface and pore structure of the membrane. This rinsing step takes about one minute to complete according to the methods of the embodiment. The rinsing is preferably done with RO water at ambient temperature (20-25° C.) to cool down the membrane quickly and thus minimize any reaction between the bare membrane surfaces and the cleaning composition during this rinsing step.

When the inventive composition is used to clean the dialysis membrane assembly, the data shows that nearly complete recovery of middle molecules clearance is achieved as provided in the Examples. The dextran probes used in assessing the clearance of molecular weight range of 0.5-30 kD covers the molecular weight/size range of uremic middle molecules relevant to hemodialysis. Also, we found that when the same dialysis membrane assembly is reused to perform dialysis 60 or more times, the recovery of middle molecules clearance was nearly complete after each treatment. These results support that the cleaning compositions and treatment methods according to the embodiment when used in combination may be sufficient to prevent cumulative deterioration of the clearance performance of the dialyzer after multiple uses.

Cleaning Protocol Using Backfiltration

An additional embodiment pertains to the preferred treatment method with the instant composition. The preferred treatment is when the cleaning composition is supplied by backfiltration where it enters the hollow fibers in the outside-in configuration. According to this configuration, the cleaning solution is forced from the dialysate compartment to flow through the membrane and enters the blood compartment (lumen side) for a period of time. This arrangement allows the cleaning composition to become in contact with all the pores and to cover all the fiber surfaces of the dialyzer at the same time. The cleaning composition needs to be applied at a temperature of more than about 40° C., and preferably 45° to 55° C. to be effective in cleaning the membrane in a short period of time, about 5-10 minutes. Again, the use of this temperature range was found to be desirable to achieve effective cleaning and to restore the pore size distribution to nearly its original level. It is recommended to limit the cleaning time to about 5 to 7 minutes to avoid exposing the bare membrane surfaces to the cleaning mixture. In a related embodiment, the flow conditions at the lumen side of the dialyzer during cleaning needs special consideration. For highly fouled dialyzers with blood clots, the use of the static method may be employed where the two compartments of the dialyzer are filled with the cleaning composition followed by allowing the dialyzer to stand quiescently for some time (15 to 30 minutes) before rinsing the dialyzer with (RO) water. After rinsing, the dialyzer is further processed to measure TCV and fiber leaks and then followed by filling the dialyzer with a high level disinfectant and allowing it to dwell for a defined period of time before using it to perform dialysis.

In another embodiment, the dialyzer is processed by introducing the cleaning composition by backfiltration and allowing the solution to exit the dialyzer through the ports of the blood compartment. During processing, flow arrangements where alternating cycles involving flow of the cleaning solution on the lumen side only for some time followed by backfiltration for another period of time are desirable to achieve effective cleaning. During cleaning, the cleaning composition as disclosed in the embodiment advantageously is applied at temperatures of more than 40° C. and preferably between 45°-55° C. for 5 to 7 minutes.

Cleaning Protocol with "Two-Phase" Flow

A preferred embodiment for cleaning PVP-containing dialysis membranes comprises a mixture of gas and liquid where the liquid fraction includes the composition according to the embodiment. According to this treatment, the liquid fraction of gas-liquid mixture is provided by backfiltration from the dialysate compartment at a temperature of about 40° C. to about 55° C. and the gas fraction is delivered as compressed air through the lumens of the hollow fiber membrane at the ambient temperature. The temperature of the cleaning liquid provided to the membrane is maintained at about 40° C. to about 55° C. to ensure effective reaction between cleaning composition and residual membrane fouling proteins. The nearly HOCl-free composition as described in the specification is delivered by backfiltration at volumetric flow rates between 100 and 600 ml/minute and preferably between 250 and 500 ml/minute. The gas fraction of the mixture is provided as compressed air via the lumen side of the dialyzer at volumetric flow rates between 56 to 150 liters per minute at STP, and preferably at 72 to 120 liters per minute at STP. According to this treatment, as the gas mixes with the backfiltered liquid, inside the fiber lumens, it forms a cleaning composition comprising the liquid-gas mixture. During a cleaning cycle lasting 5 to 7 minutes, the volume of the air-liquid mixture used to treat the membrane is about 500 liters at STP. The liquid to gas ratio is normally about 1:250 to 1:400 by volume. As the nearly HOCl-free composition reacts with residual protein in the dialyzer at about 40° C.-about 55° C., it produces surface active protein fragments that decrease surface tension of the liquid fraction to below 72 dynes/cm and supports the formation of bubbles and expansion of the air-liquid interface surface area which increase the cleaning rates. When this lower surface tension liquid is mixed with gas inside fiber lumens, it created large surface area of air-liquid interface where proteins can be readily extracted, become suspended during cleaning and removed readily from the dialyzer during cleaning. These processes enhance the mass transfer rates to remove dislodged proteins and blood clots from the dialyzers during the 5-7 minutes cleaning cycle.

This highly enhanced extraction rate process increases the rate of membrane cleaning significantly while at the same time shortening the time where the native membrane surface becomes exposed to the cleaning composition. In this embodiment, we define an index to measure the effectiveness of the extraction rate and cleaning effectiveness called "number of volume exchanges or NVE." NVE is defined as the number of volume exchanges of the blood compartment of the dialyzer with the air-liquid mixture during one cleaning cycle. It is assumed that one volume exchange of the inventive air-liquid composition will result in completely sweeping the surface of the membrane, including its pore structure, one time. The use of NVE as an index to express removal of fouling proteins is accepted in chemical engineering to express extraction rates in the continuous flow reactor case. For example, if the air-liquid mixture delivered during a 5-minute cleaning cycle is 500 liters and the volume of the blood compartment of a typical dialyzer is 0.1 liters, NVE is estimated at about 5,000. According to the present embodiment effective NVE resulting is sufficient cleaning with the air-liquid mixture is between 3,000 and 5,000 and preferably more than 4,000.

Yet another embodiment relates to a novel cleaning composition comprising the air-liquid mixture wherein the liquid fraction includes the composition and characteristics described in the specification. This inventive air-liquid cleaning composition is preferably described by the air-liquid ratio between about 1:250 to 1:400 by volume. During treatment according to the gas-liquid method, there are periods where backfiltration is used first, followed by an initial pulse with gas which is then followed by steady gas-liquid cleaning. These steps according to this sequence were found to effectively removal of blood clots and proteins from the fiber lumens of the dialyzer and from the rest of the dialysis membrane assembly without need for manual intervention.

The Steps Describing Gas-Liquid Treatment Method/Process

Figure 13:
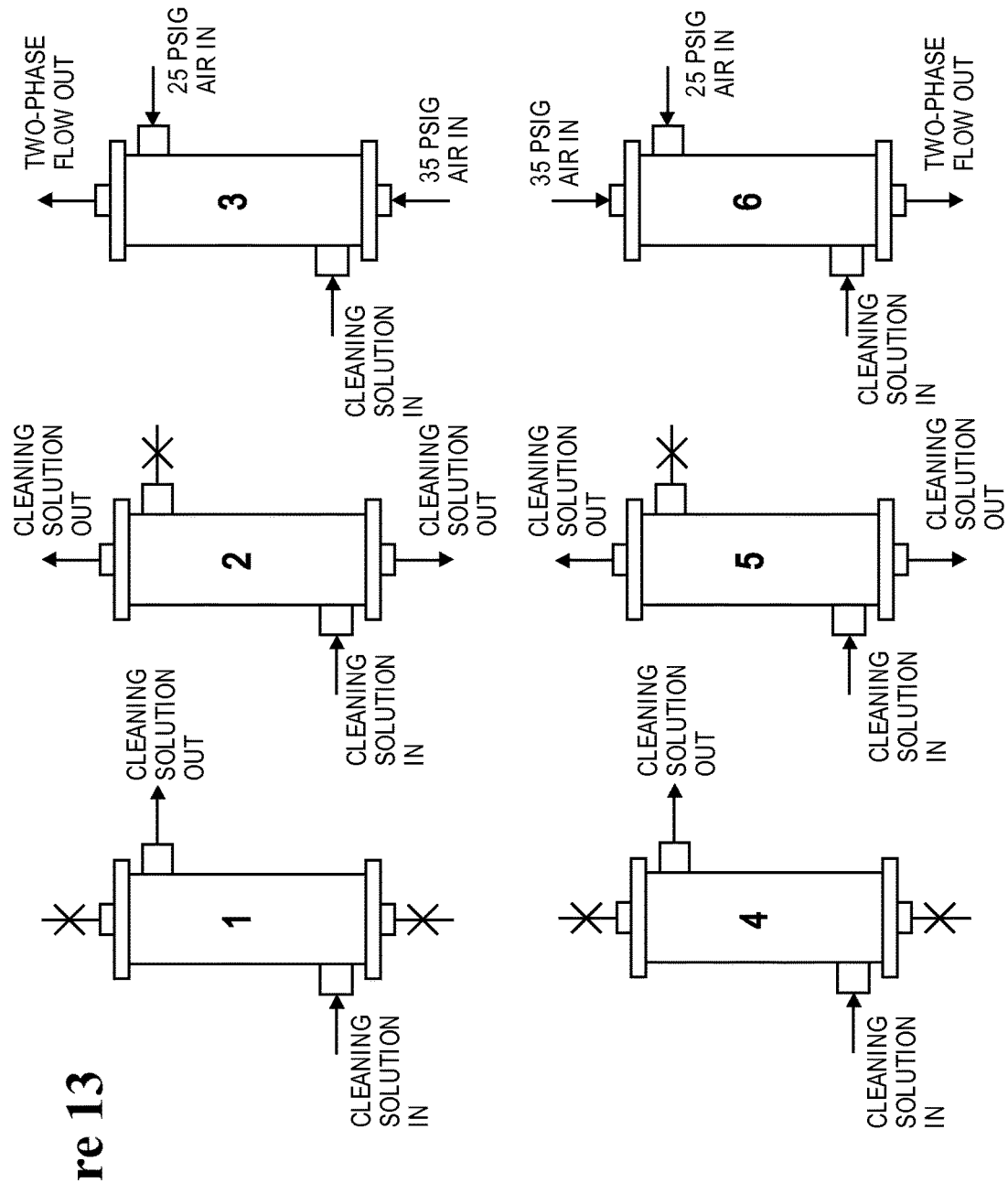
FIG. 13 is a diagram depicting the sequence of flow during dialyzer processing according to the gas-liquid treatment method. The six steps shown in this figure are detailed in the specification.

The heated cleaning composition at about 40° C. to about 55° C. is introduced into the dialyzer via backfiltration according to the following sequence of steps (FIG. 13):

Step 1: The purpose of this step is to displace and remove any air from the dialysate compartment of the dialyzer. In this step, the cleaning composition is introduced into the dialyzer by a special positive displacement metering pump via the bottom dialysate port. Residual air exits the dialysate compartment through the top dialysate port as it is replaced by the cleaning solution. At the end of this step, all the air is removed from the dialysate compartment, which then becomes filled with the cleaning solution at about 40° C. to about 55° C. The top and bottom ports of the lumen side are closed during this step (FIG. 13—[Step 1 of 6]).

Step 2: In this step, liquid cleaning composition at about 40° C. to about 55° C. is introduced from the dialysate side of the dialyzer into the fiber lumens. The in-use liquid cleaning composition enters the dialyzer via the bottom dialysate port, flows through the membrane pore structure by backfiltration, and then exits the dialyzer through both the top and bottom blood ports. The top dialysate port is closed during this step. At the end of this step, the cleaning solution has passed through the membrane pore structure for some time, and both the dialysate and blood compartments are filled with the cleaning solution (FIG. 13—[Step 2 of 6]).

Step 3: In this step, the gas-liquid mixture is formed inside the hollow fibers by mixing the back-filtered liquid with the air introduced via the lumen port of the dialyzer with the flow direction from the bottom to the top of the dialyzer. This gas-liquid mixture is made by passing the in-use cleaning solution at about 40° to about 55° C. through the membrane pore structure by backfiltration, while simultaneously introducing HEPA-filtered compressed air from the bottom blood port. As the HEPA-filtered air mixes with the back-filtered liquid cleaning composition, at about 1:200 to 1:400 liquid-to-air ratio, a high velocity gas-liquid mixture flows through the hollow fibers of the dialyzer. This high-velocity gas-liquid flow generates sufficient shear stresses at the fiber lumens to remove clots and proteins from the dialyzer, and automatically cleans the headers at the same time. In this step, the back-filtered cleaning solution at about 40° to about 55° C. mixes with about 100 Liters at STP filtered air at 2.4 atmosphere gage pressure introduced to the dialyzer via the bottom blood port to generate the gas-liquid mixture inside the fiber lumens. During this step, air is supplied at 1.7 atmosphere gage pressure to the top dialysate port of the dialyzer to keep the trans-membrane pressure (TMP) at below 0.8 atmosphere during cleaning, the limit recommended by dialyzer manufacturers. In this step, the gas-liquid mixture exits the dialyzer through the top blood port via the top header (FIG. 13—[Step 3 of 6]).

Step 4: This is the same as Step (1), above and is designed to displace the air from the dialysate compartment of the dialyzer (FIG. 13—[Step 4 of 6]).

Step 5: This is the same as Step (2), above and is designed to perform brief backfiltration and to fill both the dialysate and blood compartments of the dialyzer with the in-use cleaning composition at about 40° to about 55° C. (FIG. 13—[Step 5 of 6]).

Step 6: This is the gas-liquid flow cleaning step where the air-liquid mixture is formed as described above with the flow direction from the top to the bottom of the dialyzer. This is the same as Step (3), but with the flow direction reversed (FIG. 13—[Step 6 of 6]).

Steps 1 through 6 are repeated 5 to 10 times during the 5-7 minute cleaning cycle. During the gas-liquid treatment cycle, the arterial and venous sides of the dialyzer receive equal cleaning by reversing the flow direction so that each side receives the same amount of treatment.

The fluid manipulation during the gas-liquid cleaning method is desirable for the effective cleaning of the dialyzer. The simultaneous backfiltration of the in-use cleaning composition at about 40° C. to about 55° C. through the membrane pore structure and the formation of the high-velocity gas-liquid mixture inside the hollow fibers are optimized to recover the convective clearance (clearance of uremic middle molecules) and the TCV of the dialyzer. The combination of the inventive cleaning composition, the fluid delivery mode by backfiltration through the membrane pore structure, and the fluid dynamics of the gas-liquid flow inside the fibers and headers create the desirable conditions to effectively clean dialyzers without the need for any manual intervention.

An embodiment pertains to a fully automated process for cleaning and processing dialysis membrane assemblies by the combination of the composition and treatment method according to the gas-liquid treatment sequence of steps described above.

Cleaning Protocol with Acid Polishing Step

Example 13 shows yet another an embodiment of the present embodiment of the invention that a further acid polishing step further improve the result.

Method to Determine the Optimal Composition for Different Membranes

We have made another important finding in relation to dialysis membranes made by different manufacturers. Although all manufacturers use a blend of polyethersulfone (PES) and PVP (PES-PVP) to make dialysis membranes, different membranes respond somewhat differently to the cleaning composition and some adjustments are required. We have developed special methods to determine the optimal composition to be used with different form of PES-PVP dialysis membranes within the boundaries of the current embodiment of the invention. In this respect, we found that testing the membrane within a range between 0.5 to 30 ppb of free HOCl while assessing middle molecules clearance using dextran probes between 5 to 30 kD to provide reliable means to narrowing the composition to optimal values. The above methods include testing after simulated exposure to the cleaning composition and measuring albumin loss as detailed in Example 14. The need for adding other salts or additives is also determined according these predictive methods. Hence, one skilled in the art may use these methods to define compositions by varying the parameters according to the teaching of this embodiment of the invention. Therefore, the teaching of the embodiment of the invention is not intended to be limited to the composition of the dialysis membrane and should not to be limited to PES-PVP type. In other words, these cleaning compositions and related methods may apply to other polysulfone-based membranes and to other polymeric membranes that may be degraded by free chlorine.

Methods

Figure 10:
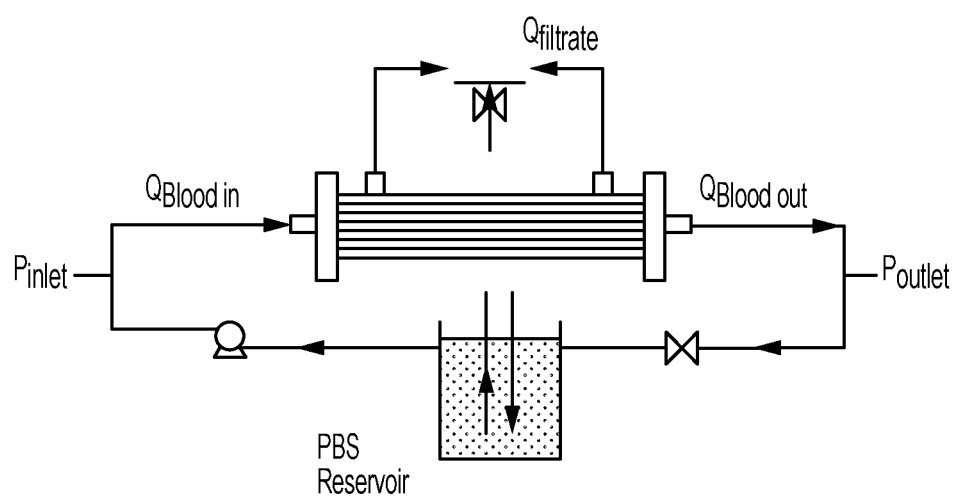
FIG. 10 is a schematic drawing of the experimental set-up for the cross flow permeability method.

Method A—Determination of the Cross Flow Permeability of Dialyzers:

The hydraulic cross flow test is performed with the dialyzer aligned horizontally (FIG. 10). The inlet and outlet pressures were measured using pressure ports connected to water manometers. PBS (or RO water) was pumped (300 mL/min) into the blood-side inlet port of the hemodialyzer with the dialysate compartment fully filled with the same solution. The system was allowed to stabilize for approximately 15 minutes. The blood outlet pressure (controlled by a valve in the blood outlet line) was slowly raised to obtain several data points with different pressure driving forces. The resulting ultrafiltration flow rate out of the dialysate side (Qfiltrate) was measured by timed collection, with two repeat measurements obtained at each pressure setting. The ultrafiltration rate was evaluated according to the following equation:

$$L_p = \frac{Q_{filtrate}}{0.5(P_{inlet} + P_{outlet})} \qquad \text{Equation 9}$$

where $Q_{filtrate}$ is the trans membrane flow rate and $P_{inlet}$ and $P_{outlet}$ are the pressures measured just before the blood-side inlet and just after the blood-side outlet, respectively. The denominator is the average trans-membrane pressure (assuming all pressures are relative to the dialysate-side pressure). The pressure drop across the blood-side inlet and blood-side outlet header regions, as well as the pressure drop through the fiber lumens, are essentially averaged out in this analysis since the inlet header loss would need to be subtracted from $P_{inlet}$ while the outlet header loss would need to be added to $P_{outlet}$ to calculate the pressures inside the dialyzer on the blood-side. In addition, by collecting the dialysate flow through both of the dialysate ports, we minimize the resistance provided by the flow through both the dialysate region and the exits.

Figure 11:
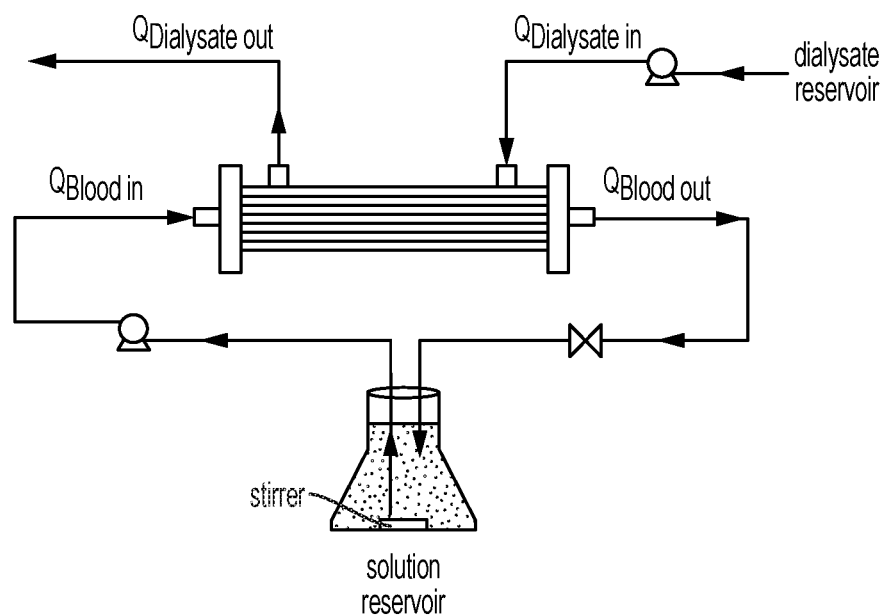
FIG. 11 is a schematic drawing of the experimental apparatus used to determine the clearance of small and middle molecules of the dialyzers.

Method B—Evaluation of Small Solute, Middle Molecule and Albumin Clearance of Dialyzers:

Solute clearance was evaluated using an automated dialysis apparatus (FIG. 11). Fluid was pumped counter-currently through both the blood and dialysate sides of dialyzers using three calibrated peristaltic pumps. Flow rates were monitored and controlled by K-flow flowmeters (ABB K-flow Inc., Millville, N.J.). Air traps with screens were placed in both the blood and dialysate lines to eliminate air bubbles and to reduce pressure fluctuations. The pumps, flowmeters and thermocouples were connected to a computer, with control and data acquisition done using LabView. This allowed the inlet and outlet flow rates, the ultrafiltration rate, and the blood/dialysate temperatures to be maintained constant throughout the experiments.

Clearance experiments were performed using urea, vitamin B12, bovine serum albumin, and polydisperse dextrans as model solutes (all obtained from Sigma Chemical, St. Louis, Mo.). The use of polydisperse dextrans to study the clearance characteristics of large solutes during hemodialysis is well-established in the literature. Bovine serum albumin was used to examine the effects of dialyzer reprocessing on albumin loss. Phosphate buffered saline (PBS) was prepared by dissolving 0.67 g NaOH, 4.08 g KH2PO4, and 8.04 g Na2HPO4.7H2O in one liter of de-ionized distilled water. The pH of the solution was adjusted to 7.4 by the addition of H3PO4 or NaOH as needed.

Urea, vitamin B12, and albumin concentrations were evaluated spectrophotometrically using a Lambda 4B UV-VIS spectrophotometer (Perkin-Elmer Corp.). Vitamin B12 concentrations were determined using vitamin B12's natural absorbance at 360.2 nm. Urea concentrations were determined by using a commercial diagnostic (BUN Endpoint 50, Sigma Chemical) with the absorbance evaluated at 340 nm. Albumin concentrations were determined by a dye-binding assay using bromcresol green. Dextran samples were analyzed by gel permeation chromatography (Agilent HPLC system) using a TSK3000SW column with a nominal pore size of 200 Å (Toyo Soda Manufacturing Co., Ltd., Tokyo, Japan). 0.15 M PBS was used as the eluent at a flow rate of 0.80±0.01 ml/min. Dextran concentrations were determined from the refractive index. The data was expressed as chromatograms showing the dextran concentration as a function of the dextran molecular weight, with the latter determined from a calibration curve constructed using dextran standards (American Polymer Standards Corporation, Mentor, Ohio).

The dialysate solution (pure PBS) was used in a single-pass mode at a flow rate of 500 ml/min. PBS containing the solutes of interest was used as the blood-side fluid at a flow rate of 350 ml/min. The system was allowed to stabilize by passing about 1 liter of solution through both the blood and dialysate inlets in a single-pass mode. After stabilization, the inlet and exit tubing on the blood-side were placed in the solution reservoir to begin the experiment. Samples were collected from the reservoir over time for off-line analysis of the solute concentrations.

The solute clearance was evaluated from the change in solute concentration in the solution reservoir as a function of time. A simple mass balance of the fluid within the reservoir can be written as:

$$V \frac{dC}{dt} = Q_B (C_{return} - C) \qquad \text{Equation 10}$$

where $C$ and $C_{return}$ are the solute concentrations in the stream leaving and returning to the reservoir, respectively. $C_{return}$ can be related to the solute concentration that entered the dialysis circuit at time $t-\Delta t$, where $\Delta t$ is the time lag between the solute leaving the reservoir in the outlet line and returning to the reservoir after passing through the dialyzer. For experiments performed at zero ultrafiltration, $C_{return}$ is given as:

$$C_{return} = \left(1 - \frac{K}{Q_B}\right) C_{t-\Delta t} \qquad \text{Equation 11}$$

where K is the solute clearance. For times greater than $\Delta t$, Equation 12 has a solution of the form:

$$\ln\left(\frac{C}{C_0}\right) = -\alpha_t \qquad \text{Equation 12}$$

Morti and Zydney, (1998) and Wolff and Zydney et al., (2004 and 2005) showed that the experimental data is in excellent agreement with this linear relationship, allowing the parameter $\alpha$ to be evaluated by simple linear regression. The solute clearance is then determined as:

$$K = \frac{\alpha V}{\exp(\alpha \Delta t)} - \frac{Q_B}{\exp(\alpha \Delta t)} [1 - \exp(\alpha \Delta t)] \qquad \text{Equation 13}$$

where the mean time lag ($\Delta t$) can be evaluated from the total circuit volume (dialyzer plus external tubing) as $\Delta t = V_{circuit}/Q_B$. This approach provides a much more accurate analysis of the solute clearance since the results are much less sensitive to any errors in the solute concentration measurements. Note that the volume of the solution reservoir can be adjusted based on the expected solute clearance to insure reasonable experimental times and concentration variations.

Method C—Determination of Albumin Loss of Dialyzers:

The albumin loss of dialyzers was determined by measuring the protein concentration in the collected bicarbonate dialysate during in-vitro simulated dialysis testing using human and bovine blood. Typically one (1) liter of blood was used in each experiment. The simulated dialysis was performed using a dialysis machine for the case of human blood. The in-vitro set up (FIG. 11) was employed in the case of bovine blood as described in Method B. Blood and dialysate flow rates were 300 and 400 ml/minute, respectively. Typically the simulated dialysis session lasted at least two (2) hours and the amount of collected dialysate used to determine albumin loss of the dialyzers was about 50 to 60 liters. The protein analysis method was used to determine the concentration of protein in the dialysate. The total protein lost in the dialysate was computed and the data is expressed in grams per dialysis session as normally accepted in the literature (Bosch et al.).

Method D—Determination of the Oxidation-Reduction Potential (ORP) of Cleaning Solutions/Compositions:

The ORP of the cleaning solutions was measured with a platinum electrode assembly with a Ag/AgCl half-cell reference using an ORP analyzer/meter made by the Thermo Fisher Scientific company (Vernon Hills, Ill.). The measurement proceeds as follows: the electrode calibration is checked by reading two standards based on quinhydron solutions made in pH 4.0 and 7.0 buffers according the Beckman-Coulter Calibration Bulletin, and then the sample ORP is measured in millivolts (mV) from the analyzer/meter. The recorded reading provides the actual ORP, i.e., the analyzer/meter is programmed to subtract the potential of the reference half-cell from the total mV measured. The data provided in this embodiment represents the actual ORP of the cleaning composition tested as normally used in the water industry.

Method E—Determination of Alkalinity:

The alkalinity of the cleaning solutions was determined by direct acid-base titration with 0.1N H2SO4 standard solution according to standard methods used in water analysis. The amount of consumed acid per liter is converted to mg/L CaCO3 which is normally used as units to express total alkalinity in the water industry. This method is important since total alkalinity of the cleaning compositions mentioned in the embodiment is due to contributions from all the ingredients used: caustic NaOH, commercial NaOCl and phosphates.

EXAMPLES

Example 1: Loss of Convective Clearance of Dialysis Membranes Processed with Peracetic Acid and Relationship Between Cross-Flow Permeability and Middle Molecules Clearance This example demonstrates that peracetic acid processing causes a significant decrease in the convective clearance of the dialyzers (clearance of middle molecules), and establishes the relationship between the loss of convective clearance and cross-flow ultrafiltration rate (Lp). Patient dialyzers were selected at random after one or more reuses/processing with the peracetic acid method. The cross-flow permeability (Lp) and clearance of middle molecules (dextran probes) of the same dialyzers were measured according to Methods A and B, respectively.

Table 4 shows a significant decrease in the convective clearance of dialyzers used by patients and reprocessed by the peracetic acid method as a function of the reuse number. This data indicates that deposited and adsorbed proteins in the membrane pore structure of the dialyzer results in a significant decrease in the convective clearance as evidenced by the results of the accepted dextran clearance methodology. This dextran method has been established in the literature for the determination of the convective clearance of ultrafiltration membranes. The data also shows that the ultrafiltration rate (permeability) of the dialyzer decreases as a function of the number of reuses. The rate of decrease in the convective clearance differs depending on the molecular weight of the dextran probes used.

In conclusion, peracetic acid processing of high-flux dialyzers leads to a significant decrease in both the convective clearance of dextran probes and the cross-flow ultrafiltration rate (Lp) compared to new dialyzers. This example clearly supports a close relationship between the convective clearance of middle molecules and the cross-flow ultrafiltration rate (Lp) of the dialysis membrane. Hence, the cross-flow ultrafiltration rate (Lp) can be used as a good predictor for middle molecules convective clearance per the current embodiment.

TABLE 4

| | Percentage of Lp decrease of Polyflux - 17R | | | |
|---|---|---|---|---|
| Number of uses | 0 (New) | 1 | 3 | 7 |
| $L_P$ (% of new) | 100 | 60 | 60 | 55 |
| Dextran Clearance (% of new) | | | | |
| 5 kD | 100 | 75 | 65 | 53 |
| 10 kD | 100 | 57 | 38 | 20 |
| 15 kD | 100 | 40 | 20 | 7 |
| 20 kD | 100 | 21 | 10 | 5 |
| 25 kD | 100 | 10 | 5 | 0 |

Example 2: Cleaning Dialysis Membrane Assemblies with High-Caustic/High Alkalinity Only Polyflux® Gambro dialyzers used to perform dialysis treatment were cleaned with a high pH sodium hydroxide solution (pH 12.3) at 45°-50° C. according to the gas-liquid method described in the embodiment. The cross-flow permeability (Lp) and the dextran clearance of the dialyzers were measured according to Methods A and B, respectively. Table 5 shows that cleaning the dialysis membrane assemblies with high pH caustic solution even at 45°-50° C. does not fully recover the cross-flow permeability or the middle molecules clearance as assessed by dextran probes (Table 6). This treatment was only capable of restoring 70% of the cross-flow permeability compared to new dialyzer levels. The clearance of 5 kD dextran was close to new dialyzer levels; however, there was a significant decrease in the clearance of large dextrans as shown in Table 6. When dialyzers used by the same group of patients multiple times and then cleaned with the above caustic solution (NaOH and pH 12.3) according to the gas-liquid method of the embodiment, a significant decrease in cross-flow permeability and dextran clearance was found. In conclusion, compositions based on high pH (high alkalinity) only are ineffective in cleaning the dialysis membrane and specifically with respect to restoring the middle molecules clearance function.

TABLE 5

| Dialyzer | $L_p$ (New Dialyzer) (ml/min/mmHg) | $L_p$ (1 Reuse) (ml/min/mmHg) | $L_p$ (3 Reuses) (ml/min/mmHg) | $L_p$ (7 Reuses) (ml/min/mmHg) |
|---|---|---|---|---|
| Polyflux-17R | 452 | 314 | 197 | 125 |
| % of New | 100% | 70% | 44% | 28% |

TABLE 6

| Dextran Probe | New | 1 Reuse | 3 Reuses | 7 Reuses |
|---|---|---|---|---|
| 5 kD | 82 | 80 | 28 | 40 |
| 10 kD | 47 | 36 | 20 | 10.5 |
| 15 kD | 30 | 19 | 8.5 | 3.0 |
| 20 kD | 20 | 10.9 | 5.2 | 2.0 |
| 25 kD | 14 | 6.4 | 3.4 | 1.5 |

Example 3: Effect of Hypochlorite Salt Concentration on the Recovery of Middle Molecules Clearance of Dialysis Membranes In this example, two cleaning mixtures were made at the same pH (12.3) to demonstrate the effect of the concentration of the hypochlorite salt used in the inventive composition on the clearance of middle molecules of a dialysis membrane type made by one manufacturer. Composition A had 625 ppm NaOCl and Composition B has 1000 ppm NaOCl. The pH was adjusted with NaOH as described in the specification. The dialyzers were used to treat the same group of patients with each treatment lasting 4 hours. The dialyzers were cleaned at 45°-50° C. using the gas liquid treatment method according to the embodiment. Table 7 summarizes the results for Compositions A and B, respectively.

The results demonstrate that the Composition A (1000 ppm NaOCl) provides effective recovery of dextran probes clearance but causes an increase the clearance levels of dextran probes above those of new dialyzers. On the other hand, Composition B (650 ppm NaOCl) is not sufficient enough to restore fully dextran clearances to the levels of new dialyzers. Based on the results of this example, NaOCl concentration between 625 and 1000 ppm can be made to achieve full recovery of middle molecules without altering the sieving properties of the dialysis membrane.

This example also describes a definitive method to define the optimal composition needed to clean and restore the clearance functions of middle molecules of dialysis membranes made by different manufacturers as described in the embodiment. The compositions used in this example are effective at high pH (12.3), defined level of hypochlorite salt, nearly HOCl-free composition, low ORP and needs to be applied at 45° C.–55° C. as detailed in the embodiment.

TABLE 7

| Dextran Probe | New (Control) | (Composition A) (625 ppm) | (Composition B) (1000 ppm) |
|---|---|---|---|
| 5 kD | 72.5 | 67.0 | 81.3 |
| 10 kD | 27.5 | 22.3 | 32.0 |
| 15 kD | 13.0 | 10.0 | 15.3 |
| 20 kD | 7.0 | 7.7 | 8.1 |
| 25 kD | 3.9 | 2.5 | 4.5 |

Example 4: Recovery of Middle Molecules Clearance of Dialysis Membranes According to the Compositions and Methods of the Embodiment Dialyzers used to treat random dialysis patients were processed with the inventive compositions by employing the gas-liquid treatment method at about 40° C. to about 55° C. The convective clearance of the dialyzers was measured by the dextran probe Method B. The data shows that the composition according to the embodiment may fully recover the convective clearance of patient dialyzers (Table 8). Further testing shows that there is no deterioration on the dialyzer clearance function when these dialyzers were used to treat the patients multiple times.

TABLE 8

| | Solute Clearance (mL/min) | |
|---|---|---|
| Solute | New (Average of 3 dialyzers) | Patient-Used Dialyzers Cleaned According to the Embodiment (Average of 6 patients) |
| 5 kD | 72.5 ± 2.1 | 80.0 ± 12.1 |
| 10 kD | 27.5 ± 3.5 | 30.3 ± 6.4 |
| 15 kD | 13.0 ± 1.4 | 14.0 ± 3.2 |
| 20 kD | 7.0 ± 1.1 | 7.3 ± 2.0 |
| 25 kD | 4.0 ± 0.8 | 4.0 ± 1.3 |

In conclusion, testing the recovery of the convective clearance of dialyzers with the composition and method according to the embodiment demonstrates that full recovery of the convective clearance (middle molecules) of the dialyzers. It should be noted that the effectiveness of the convective clearance recovery was determined by comparison with new dialyzers from the same lot. The recovery of clearance indicates that treating the dialyzers according to the embodiment completely cleans the pore structure of the dialysis membrane and restores both the sieving coefficient and ultrafiltration rate.

Example 5: Effect of pH (Alkalinity) on the Cross-Flow Permeability of PVP-Containing Dialysis Membranes Dialysis membrane assemblies made by Gambro® (Polyflux® 21R) were subjected to 20 simulated cleaning cycles according to the gas-liquid treatment method of the embodiment using two cleaning mixtures. Both mixtures had the same concentration of added hypochlorite salt (NaOCl) of 500 ppm but had different pH. The first cleaning mixture was made without pH adjustment (about 7.5) while the second mixture was made at pH of about 12. The cross-flow water permeability was measured according to Method A after exposure to the 20 simulated cleaning cycles and compared with control new dialyzers. The results in FIG. 3 show that added hypochlorite salt used without pH adjustment increases the cross-flow permeability by a factor of 4 from about 500 to 2000 ml/mmHg·hr compared to control new dialyzers. In contrast, when the same concentration of added hypochlorite salt is made at pH of about 12 according to the embodiment, there was only a very small increase in the cross-flow permeability. We have established previously that an increase in cross-flow permeability correlates with an increase in the middle molecules clearance of the membrane. It is clear that compositions based hypochlorite salts without pH adjustment, such as in DRS-4, lead to severe degradation of the PVP-containing dialysis membranes resulting in an increase in their pore size which is not desirable because this leads to albumin loss during dialysis as described in the specification. On the other hand, compositions made according to the embodiment at high pH (high alkalinity) are nearly HOCl-free and do not lead to degradation of the PVP-containing dialysis membrane. The results of this example were found to be valid for many of the dialysis membranes made by different manufacturers; however, the level of degradation varies among the different membranes. Further adjustment of the composition leads to even better performance as detailed in the embodiment.

Example 6: X-Ray Photoelectron Spectroscopy (XPS) Analysis after Cleaning According to the Compositions and Methods of the Embodiment A. Dialyzer Preparation for XPS Analysis:
1. Control/New Dialyzers:

Control/new dialyzers were prepared by filling them with AAMI RO water and then storing them at 5° C. until the time of XPS analysis. Both control and simulated dialyzers were picked from the same production lot to allow for reliable analysis.

2. Simulated Cleaning According to the Embodiment:

The simulated dialyzers were cleaned 40 times according to the compositions and methods described in the embodiment. After completing the simulations, the dialyzers were rinsed with AAMI RO water. The dialyzers were then filled with AAMI RO water and preserved at 5° C. until the time of the XPS analysis. Typically, the dialyzers were stored in the refrigerator until they were tested.

3. X-Ray Photoelectron Spectroscopy (XPS):

The testing was performed according to recommended methods for XPS analysis specifically to prevent surface contamination or degradation due to the x-ray beam during the analysis. XPS is an established surface analytical technique that provides chemical bonding information from the topmost 40-100 Angstroms of a surface. XPS is well suited to assessing the surface chemistry of polymeric materials, such as those used to make dialysis membranes. The technique provides elemental composition information of surfaces as well as chemical bonding details of the atoms present in such surfaces.

B. Method of Preparing the Dialyzers:

To prepare fiber lumen samples, the dialyzers were cut with a special saw to separate a 6-inch long fiber bundle in the middle of the dialyzer. Fibers from different sections of the bundle were selected at random to make a representative sample. The fibers selected were then sliced at a low angle to expose fiber lumens for the XPS analysis. The fiber lumen surfaces were then analyzed according to established protocols.

C. Results and Conclusions:

Surface Chemical Composition of Dialyzers—XPS Results: Table 9 provides a summary of all dialyzers used for the XPS analysis.

TABLE 9

| Dialyzer Manufacturer | Dialyzer Model | Treatment | Nitrogen (Atom %) |
|---|---|---|---|
| Gambro ® | Polyflux 17R | New | 2.4 |
| | Polyflux 21R | 19 ClearFlux Cycles | 3.2 |
| | Polyflux 21R | 40 ClearFlux Cycles | 3.1 |
| Fresenius ® | Optiflux 200A | New | 2.3 |
| | Optiflux 200A | 40 ClearFlux Cycles | 2.4 |
| | Optiflux 200B | New | 2.2 |
| | Optiflux 200B | 40 ClearFlux Cycles | 2.4 |

The elemental composition and chemical bonding information of the dialyzers' fiber lumen surface were analyzed by XPS, otherwise known as Electron Spectroscopy for Chemical Analysis (ESCA). The detailed XPS spectra of new dialyzers and simulated dialyzers were compared and analyzed. Both surface elemental analysis and chemical composition (based on binding energies) were carefully analyzed for each dialyzer type.

Elemental analysis of the topmost 40-100 Angstroms of lumen surface indicated that control/new and simulated dialyzers have the same elements (C, S, O and N) at more or less the same level within the sensitivity of the XPS technique (0.05% to 1%), and within the variability between samples of the same dialyzers. Study of the chemical bonding spectra of all of the elements present at the surface (C, O, S, and N) indicated that cleaning according to the embodiment does not alter or change the surface chemistry of any of the dialyzers examined.

Notably, the nitrogen level (expressed as atom %) remains at more or less the same level after 40 simulated cycles compared to new dialyzers. These results support the safety of cleaning according to the embodiment with respect to the level of polyvinyl pyrrolidone (PVP) present at the surface of the dialyzers; note that PVP is the only nitrogen bearing molecule in the polymer blend used to make the dialysis membrane. In all cases, the level of PVP (3-5%) after dialyzer cleaning according to the embodiment can be sufficient to retain the hydrophilic nature of fiber lumens. The chemical compositions of the fiber lumens, as expressed by the binding energy spectra, show that the composition of fiber lumens is super-imposable (new and simulated) and that there is no discernible effect of treating the dialyzer according to the methods and compositions of the embodiment on the surface chemistry of the dialyzers. These results have been generalized for high-flux dialyzers made by Gambro® and Fresenius®.

In conclusion, the surface composition and elemental analysis obtained by XPS indicate that the cleaning of the dialyzers according to the compositions and methods of the embodiment does not alter the chemical composition of the fiber lumen surface of high-flux dialyzers made by Fresenius® and Gambro®. In this respect, cleaning according to the compositions and methods of the embodiment is safe to PVP-containing dialysis membranes.

Example 7: Loss of PVP from Dialysis Membranes Processed at pH 11.3

Figure 12A:
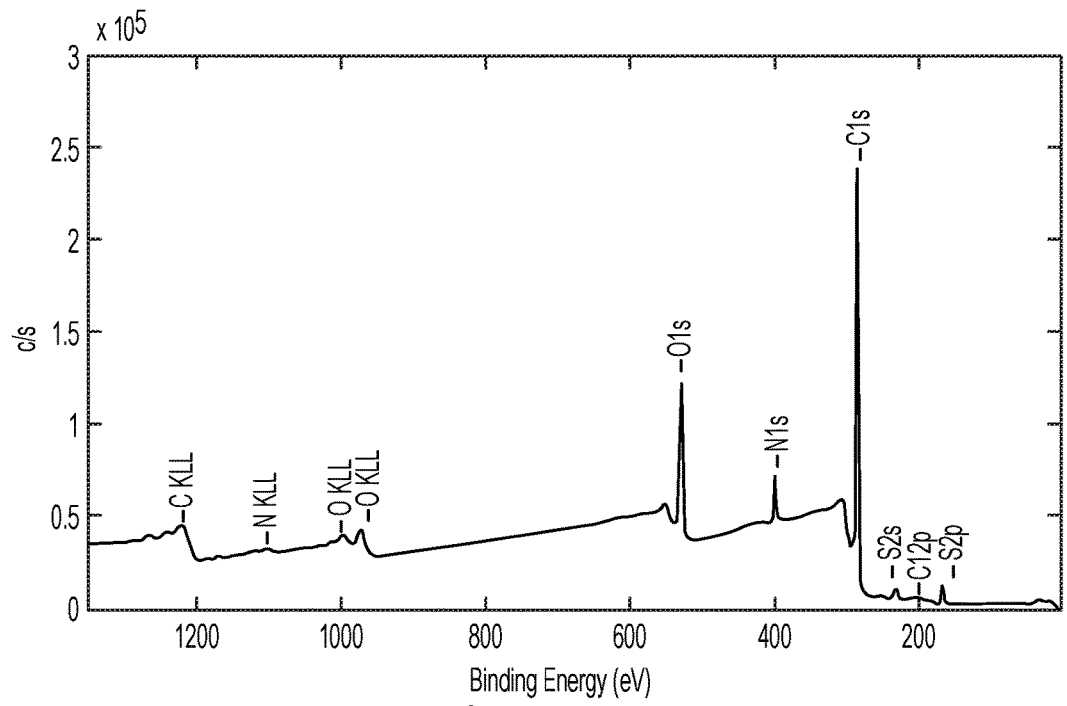
FIG. 12A and FIG. 12B (collectively, "FIG. 12") shows the XPS spectra of a new dialyzer (A) top and of a dialyzer processed using a composition including hypochlorite salt at pH 11.3 (B) bottom. Comparison of the two spectra (A and B) shows that processing the dialyzer for 13 to 20 times with this composition resulted in the complete erosion of PVP as indicated by the complete disappearance of the nitrogen peak in the XPS spectrum of the processed dialyzer (B).
Figure 12B:
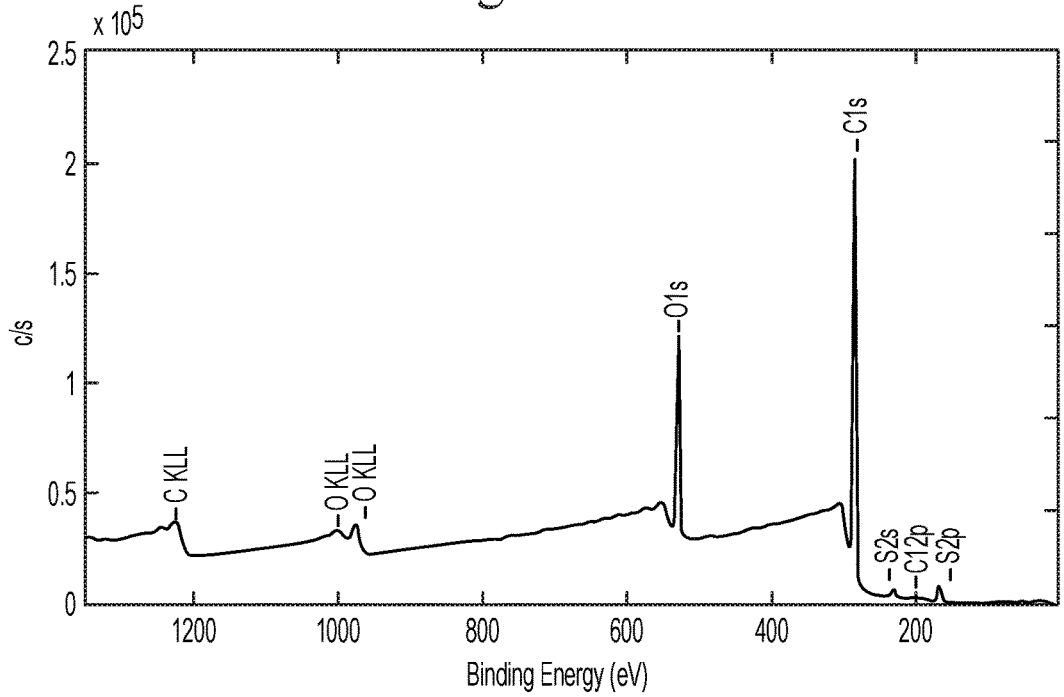

In a controlled study, eight (8) PVP-containing Fresenius Optiflux® F80A dialyzers were used to treat dialysis patients for 13 to 20 times and were processed with a solution having 2200 ppm hypochlorite salt solution (NaOCl) with the pH adjusted at 11.3 using sodium hydroxide at 45° C. following the steps of the gas-liquid method described in the specification. After cleaning, the dialyzers were rinsed with RO water, filled with 1300 ppm peracetic acid and then allowed to dwell for 15 hours before they were used to treat patients. After 13 to 20 cleaning cycles, the dialyzers were analyzed by XPS to determine the PVP content using atom percent nitrogen (a/o) as a metric since PVP is the only nitrogen bearing polymer in the membrane. We found that cleaning the dialyzer a few times with 2200 added hypochlorite at pH 11.3 does not provide protection against PVP erosion as shown in FIG. 12. FIG. 12 shows the complete loss of nitrogen from the surface of the dialyzers cleaned as described above (compared to new dialyzers). The results clearly show that operating in the flat region of the dissociation curve of hypochlorite is not sufficient to provide protection against PVP erosion form the membrane even after a small number of cleaning cycles. Accordingly, the concentration of free HOCl computed by Equation 1 at pH 11.3 is about 0.44 ppm or 440 ppb, and ORP is 0.546 volts or 546 mV. Even at these very low levels of free HOCl at pH 11.3, the degradation and erosion of PVP from the membrane remains unacceptable for treating patients without concern about albumin loss or inducement of hemo-incompatibility. It should also ne noted clear that the ORP of this composition is higher than the acceptable range of <0.5 volts according to the embodiment. Hence, adjusting both the concentration of added NaOCl and alkalinity of the cleaning solution is advantageous to provide safe and effective cleaning of PVP-containing membranes for forty (40) or more times at the ranges specified according to the present embodiment.

Example 8: Shelf-Life of the Compositions

Eleven concentrate compositions made according to the present embodiment were stored under ambient conditions and assayed periodically for available chlorine as a function of storing time using ASTM Procedure—D22022-64 (1980). The pH of tested composition concentrates was between 13.02 and 13.23 and all were made at high alkalinity using NaOH and phosphate salt. Table 10 demonstrates an outstanding stability of the inventive concentrate composition for up to two years. The concentration of added hypochlorite salt remained at more than 95% of the original value after 2 years which represents a significant advantage since hypochlorite solutions are inherently unstable. The pH of the solution was also measured as a function of time and was found to be stable over the 2 year storing period. It should be noted that the data according to ASTM Procedure—D22022-64 (1980) gives the amount of hypochlorite used to make the composition and that the concentration of free HOCl is computed according to Equation 1 at the use concentration.

TABLE 10

| Time (Months) | 1 | 3 | 6 | 12 | 18 | 24 |
|---|---|---|---|---|---|---|
| % NaOCl Remaining | 100% | 100% | 99% | 100% | 96% | 95% |
| pH | 13.21 | 13.20 | 13.22 | 13.12 | 13.25 | 13.02 |

Example 9: Effect of the Number of Cleaning Cycles on the Clearance of Urea and Vitamin B12 of PVP-Containing Dialysis Membranes Cleaning PVP-containing dialyzers made by Fresenius Optiflux® 200B and Gambro Polyflux® 21R twenty (20) and forty (40) times with the cleaning composition made at 1000 ppm hypochlorite salt and at high alkalinity according to the embodiment was found to maintain the clearance of urea and Vitamin B12 at baseline values of new dialyzers without any deterioration in performance. These results are summarized in Table 11, respectively. Notably, there was no effect of repeatedly exposing the membrane to forty (40) cleaning cycles on the pore size distribution of the membrane as determined by Vitamin B12 clearance which is recognized as an important probe to determine the clearance of hemodialysis membranes. This clearly demonstrates the effectiveness and safety of the cleaning composition of the embodiment.

TABLE 11

| Dialyzer | Urea Clearance (ml/min) | Vitamin B12 Clearance (ml/min) |
| --- | --- | --- |
| Gambro Polyflux ® 21R - New | 257 +/- 3 | 145 +/- 3 |
| Gambro Polyflux ® 21R - 20 Cycles | 251 +/- 6 | 152 +/- 3 |
| Gambro Polyflux ® 21R - 40 Cycles | 258 +/- 8 | 155 +/- 3 |
| Fresenius Optiflux ® F200B - New | 258 +/- 5 | 156 +/- 2 |
| Fresenius Optiflux ® F200B - 20 Cycles | 269 +/- 1 | 165 +/- 4 |
| Fresenius Optiflux ® F200B - 40 Cycles | 264 +/- 4 | 167 +/- 2 |

Example 10: Method for Measuring and Predicting the Effect of Repeated Cleaning Cycles on the Albumin Clearance Properties of Dialysis Membranes Measuring the albumin clearance of hemodialyzers (Method B) as a function of the number of cleaning cycles according to the embodiment was found to provide a reliable method for predicting the albumin loss behavior of the membrane. The data in Table 12 shows that when the cleaning composition was optimized for the concentration of added hypochlorite salt, alkalinity, oxidation-reduction potential and the amount of HOCl, the albumin clearance was nearly maintained at the baseline level of new dialyzers. When the above method was verified by measuring the actual albumin loss of the dialyzers in simulated dialysis using bovine blood, the resulted demonstrated that the albumin clearance method can predict albumin loss properties of the dialysis membrane. Also, when the clearance of middle molecules is assessed by the Dextran clearance (Method B) is combined with the data albumin clearance, optimal compositions for the different PVP-containing dialysis membranes can be realized according to the embodiment.

TABLE 12

| Solute | Gambro Polyflux ® 21R (New) | Gambro Polyflux ® 21R (20 cycles processed) | Gambro Polyflux ® 21R (40 cycles processed) |
| --- | --- | --- | --- |
| Albumin | 0.7 +/- 0.1 | 1.2 +/- 0.3 | 1.2 +/- 0.3 |
| | Fresenius Optiflux ® 200B (New) | Fresenius Optiflux ® 200B (20 cycles processed) | Fresenius Optiflux ® 200B (40 cycles processed) |
| Albumin | 0.3 +/- 0.3 | 0.5 +/- 0.1 | 1.4 +/- 0.1 |

Example 11: Preferred Ranges of Composition Parameters of Embodiments

Table 2 summarizes nine (9) compositions. Compositions A through F were made according to the acceptable ranges defined by the embodiment. Compositions G through I we made compare and demonstrate the existing art with the compositions of the present embodiment.

According to the embodiment, the concentration of sodium hydroxide (NaOH) is between about 8.6 g/L to about 31.2 g/L. According to the embodiment, the concentration of the hypochlorite salt (NaOCl) in the composition is between about 7.8 g/L to about 23.4 g/L. The weight ratio between the alkali metal hydroxide and the hypochlorite salt is advantageous to describe the compositions according to the embodiment. The aforementioned above ratio between about 0.5 to about 4.0 is an acceptable range and a minimum ratio of less than 0.5 is not preferred according to the embodiment of the invention. At least compositions A through F having free hypochlorous acid (HOCl) between about 2.39 to about 17.99 ppb and ORP between about 376 mV to about 475 mV are included within the ranges defined by the specification for effective and safe application to clean dialysis membrane assemblies without erosion of PVP.

On the other hand, compositions G through I are outside of the ranges recommended by the current embodiment. For compositions G through I, the ratio between the alakali metal hydroxide (NaOH) and the hypochlorite salt (NaOCl) is between 0 and 0.02 which is much lower than the 0.5 recommended in the embodiment. For these same compositions (G through I), the ORP is from about 546 mV to about 786 mV and the free hypochlorous acid concentration is in the range between 450 and 86,538 ppb. It is clear that both ORP and free hypochlorous acid for compositions G through I are outside the ranges found according to the present embodiment. Compositions A through F were tested to clean dialysis membrane assemblies multiple times and were found to achieve effective recovery of middle molecules without substantially affecting the PVP concentration in the membrane. On the other hand, when compositions G through I were used to clean the dialysis membrane assemblies, substantial erosion of the PVP from the membrane was found. Such compositions were deemed unacceptable for safe cleaning of PVP containing dialysis membranes as amply detailed in the present embodiment. Composition G was found to be marginally acceptable to clean the membrane few times only (about 13 times). This composition was found to result in the complete loss of PVP from the membrane as provided in Example 7.

Example 12: Recovery of Middle Molecular Weight Protein Clearance (Beta-2 Microglobulin and Cytochrome c)

The clearance of uremic middle molecular weight proteins was assessed when patient dialyzers were cleaned with the compositions and methods of the embodiment and compared with dialyzers cleaned with the conventional peracetic acid methods. The inventive cleaning compositions used were based on 500 ppm added hypochlorite salt (NaOCl) at an alkalinity level to result in pH 12.2 and ORP about 0.45 volts or 450 mV. The cleaning of the dialyzers was performed according to the gas-liquid method at about 40° C. to about 55° C. as detailed in the specification. Two studies were performed to assess: 1) the effect of the cleaning composition on beta-2 microglobulin clearance in dialysis patients after multiple dialysis treatments and 2) the effectiveness of the composition in recovering the dialyzer's clearance of uremic middle molecules Cytochrome c which is acceptable in the literature as a surrogate for beta-2 microglobulin.

In the first study, Fresenius® F80A dialyzers were used to treat two groups of dialysis patients (total of 16 patients) for 13 treatments. Dialyzers of 8 patients were cleaned and processed with the conventional peracetic acid method (Group 1). Dialyzers of the other 8 patients were cleaned with the inventive composition according to the gas-liquid treatment method (Group 2). Cleaning the dialyzers according to the composition and methods of the embodiment showed a reduction ratio (RR) of beta-2 microglobulin (post-dialysis beta-2 microglobulin level divided by pre-dialysis level) of 27% compared to 57.8% of patients in Group 2 where the dialyzers were processed with peracetic acid (Table 13). Moreover, after 13 treatments the patients serum concentration of beta-2 microglobulin remained low levels, 27.7 mg/L, which is identical to that when patients are treated with a new dialyzer every time as published in the literature (Diaz et al, 1993). Table 13 summarizes the results of this study.

TABLE 13

| | $\beta_2$-microglobulin | | |
|---|---|---|---|
| Method | Pre-dialysis $\beta_2$ (mg/L) | Post-dialysis $\beta_2$ (mg/L) | $\beta_2$ Reduction Ratio (%) |
| Peracetic Acid Method | 48.0 | 36.7 | 27.10 |
| Current Embodiment | 27.7 | 11.3 | 57.53 |

In the second study, when the Nephros mid-dilution hemodiafiltration filters used to perform simulated hemodiafiltration with bovine blood were cleaned with the inventive compositions and the gas-liquid method, nearly complete recovery of clearance of (Cytochrome c) of the dialyzers was achieved (Table 14). This study also demonstrated that compositions and methods of the embodiment can be effective in recovering the TCV of the dialyzers at the same time.

TABLE 14

| Conventional Peracetic Acid Method | | | Present Embodiment | | |
|---|---|---|---|---|---|
| Dialyzer # | Urea | Cytochrome c | Dialyzer # | Urea | Cytochrome c |
| New Dialyzer Clearance | | | | | |
| NF05-099 | 374.2 | 243.4 | NF05-098 | 372.6 | 242.7 |
| NF05-101 | 382.6 | 244.5 | NF05-100 | 377.0 | 250.0 |
| Avg. | 378.4 | 244.0 | Avg. | 374.8 | 246.4 |
| Post - Cleaning Clearance | | | | | |
| NF05-099 | 346.0 | 203.4 | NF05-098 | 334.3 | 239.6 |
| NF05-101 | 369.7 | 226.4 | NF05-100 | 376.9 | 248.2 |
| Avg. | 357.9 | 214.9 | Avg. | 355.6 | 243.9 |
| % Loss | −5.4% | −11.9% | % Loss | −5.1% | −1.0% |

This example clearly demonstrates the effectiveness of the compositions and methods of the embodiment in recovering the clearance of uremic middle molecular weight proteins compared to the existing methods employed in the industry. These results are significant since the sieving coefficients for proteins are somewhat different compared with those measured with dextran probes. This is because the adsorption properties of proteins and dextrans with the membrane surface are significantly different.

Example 13: Acid Polishing Step

This example demonstrates the effectiveness of an additional acid polishing step on achieving a complete recovery of the cross flow permeability of the dialyzers when such acid polishing step is applied after cleaning the dialyzer with the compositions and methods of the embodiment. The data in Table 15 shows that when dialyzers cleaned with the inventive composition at 1000 ppm added sodium hypochlorite with the alkalinity adjusted to pH 12.3 were stored in 1300 ppm solution of peracetic acid (pH 3.0) for 1 to 2 days, the cross flow permeability increased by about 5%. Storing dialyzers cleaned with the alkaline compositions of the embodiment in an oxidative acidic solution at pH 3.0 resulted in a complete recovery of the cross flow permeability to the new baselines values of such dialyzers. As detailed in the specification, recovery of the cross flow permeability correlated very well with the clearance of the middle molecules as provided in Example 1. Based on is data, exposure of the dialyzers to the acidic and oxidative conditions provided by peracetic acid results in further removal of residual proteins remaining in the dialysis membrane leading to almost full recovery of the clearance of middle molecules of the dialyzer to the baseline new conditions. According to the present embodiment, the acid polishing step may be included as a terminal final step when processing the dialyzers.

The preferred sequence of steps of cleaning and processing the dialyzers (that is hemodialysis membrane assembly having polyvinylpyrrolidone-containing membranes) according to one embodiment are, in this order: exposing the dialyzer with the inventive composition according to the steps of the gas-liquid method or other treatment methods as detailed in the specification; rinsing the dialyzer with RO (reverse osmosis treated) water at ambient temperature to remove all residual cleaning composition/solution from the dialyzer; store dialyzer acid for 1 to 2 days; followed by a second cold wash with RO water at ambient temperature to remove all residual peracetic acid.

In another preferred embodiment, the acid used is preferably peracetic acid at pH 3.0, and more preferably 1300 ppm solution of peracetic acid (pH 3.0). Preferably the dialyzer is treated with acid for 1-2 days, however in an embodiment, any time sufficient to effect disinfection or polishing is acceptable.

The preferred sequence of steps of cleaning and processing the dialyzers according to one embodiment are, in this order:

a) pre-cleaning the dialyzer with RO water to remove residual blood remaining after dialysis treatment;
b) cleaning the dialyzer with the inventive composition according to the steps of the gas-liquid method or other treatment methods as detailed in the specification;
c) rinsing the dialyzer with RO water at ambient temperature to remove all residual cleaning composition/solution from the dialyzer;
d) testing TCV and fiber leaks of the dialyzer; and
e) filling the dialyzer with an acidic (pH about 3.0) high-level peroxy-acid disinfectant such as peracetic acid and storing the dialyzer for more than 11 hours to execute the acid polishing step as detailed above.

TABLE 15

| Cross Flow Water Permeability Before Acid Polishing Step (ml/mmHg · hr) | Cross Flow Water Permeability After Acid Polishing Step (ml/mmHg · hr) |
| --- | --- |
| 279 | 282 |
| 291 | 303 |
| 237 | 250 |
| 339 | 360 |
| 281 | 304 |
| 213 | 218 |
| 279 | 300 |
| 243 | 243 |
| 277 | 303 |
| 260 | 272 |
| 373 | 394 |
| 381 | 383 |
| 252 | 257 |
| 224 | 234 |
| 293 | 306 |
| 198 | 207 |
| 193 | 202 |
| 180 | 194 |
| 196 | 200 |
| Average: 262.6 | Average: 274.3 |
| Standard Deviation: 59.9 | Standard Deviation: 60.6 |

Although there are other approved germicides available for achieving high-level disinfection of dialyzers such as aldehydes (formaldehyde or glutraldehyde), the use of peracetic acid is a preferred agent for performing the acid polishing step needed to provide the terminal removal of residual proteins from the dialysis membrane according to this embodiment. Alternatively, other organic or inorganic acids can be used to perform the acid polishing step before filling the dialyzer with a high-level disinfectant according to the AAMI guidelines.

Example 14: Albumin Loss

This example provides supporting data regarding the safety of the cleaning compositions and methods of the embodiment with respect to PVP erosion from dialysis membranes which has been linked to albumin loss from patients during dialysis when the membranes were cleaned with unbuffered commercial hypochlorite solution at 0.75 to 1.0% using the DRS-4 method as reported by Kaplan et al., (1995). As detailed in the specification, cleaning the dialyzers with proxy-acids such as peracetic acetic acid does not recover the clearance of uremic middle molecules which is unacceptable for treating dialysis patients due to the development of cardiovascular disease in this patient group. Therefore, it has been established in this embodiment that the use of a hypochlorite salt-containing composition is advantageous to recover the clearance properties of the dialyzer without causing albumin loss from patients during dialysis.

The albumin loss from the dialyzers after cleaning them according to the compositions and methods of the embodiment was assessed for different dialysis membrane types according to Method C. The results summarized in Table 16 clearly demonstrate that when the compositions of the embodiment were used to clean different PVP-containing dialysis membrane assemblies 40 to 60 times, the level of albumin loss remained at nearly the baseline levels of the new dialyzers. The inventive compositions may be thus able to restore the clearance properties of the dialyzers without PVP erosion and without increasing albumin loss during dialysis.

TABLE 16

Summary of albumin loss into the dialysate during in vitro recirculation of blood through dialyzers.

| | Dialysate Albumin (mg) | |
| --- | --- | --- |
| Processing History | 60 minutes | 120 minutes |
| New (Control) Gambro Polyflux ® 17R Dialyzers | 81 ± 29 | 105 ± 19 |
| Simulated Dialyzers Cleaned According to the Embodiment (no blood exposure) | 172 ± 67 | 139 ± 125 |
| Patient Dialyzers Processed According to the Embodiment (human blood exposure) | 204 ± 61 | 225 ± 116 |

Example 15: Fully Automated Cleaning of Dialysis Membrane Assemblies According to the Methods and Compositions of the Embodiment of the Invention Due to the complex nature of the process and the need to adjust and control many variables at the same time, the treatment methods and protocols of the embodiment are preferably executed as a fully automated process. This automated process may be employed to perform all cleaning and processing steps as follows:

Automated Step 1: Pre-cleaning of a patient dialyzer after dialysis to remove residual blood before executing the gas-liquid cleaning step is automated by delivering RO water to enter the dialyzer from blood Port 6 to exit from blood Port 8 (FIG. 8). The direction of flow is automatically reversed to direct RO water to enter the dialyzer form blood Port 8 and exit from blood Port 6. During this step, the dialyzer is flushed with RO water introduced from the dialysate side of the dialyzer via Ports 18 and/or 20 allowing the RO water to exit the dialyzer in an alternating manner from Ports 6 and 8. According to this step, the water is applied to the dialyzer under pressure and Ports 6, 8, 18, and 20 are open and closed with solenoid valves according to a specified control system.

Automated Step 2: The gas-liquid treatment of the dialyzer is automated by introducing the cleaning composition of the embodiment at about 40° C. to about 55° C. into the dialyzer via backfiltration according to the following sequence of steps (FIG. 13):

Gas-Liquid Treatment Step 1: In this step, the cleaning composition is introduced into the dialyzer by a special positive displacement metering pump via dialysate Port 18 (FIG. 8). Residual air exits the dialysate compartment through the dialysate Port 20 as it is replaced by the cleaning solution. At the end of this step, all the air is removed from the dialysate compartment, which then becomes filled with the cleaning composition at about 40° C. to about 55° C. Blood Ports 6 and 8 are closed during this step (FIG. 13—[Step 1 of 6]). Opening and closing designated ports is automated with a programmed algorithm to control a set of solenoid valves.

Gas-Liquid Treatment Step 2: In this step, liquid cleaning composition at about 40° C. to about 55° C. is introduced from the dialysate side of the dialyzer into the fiber lumens. The liquid cleaning composition enters the dialyzer via dialysate Port 18, flows through the membrane pore structure by backfiltration, and then exits the dialyzer through both blood Ports 6 and 8. The top dialysate Port 20 is closed during this step. At the end of this step, the cleaning solution has passed through the membrane pore structure for some time, and both the dialysate and blood compartments are filled with the cleaning solution (FIG. 13—[Step 2 of 6]). Opening and closing designated ports is automated with a programmed algorithm to control a set of solenoid valves.

Gas-Liquid Treatment Step 3: In this step, the gas-liquid mixture is formed inside the hollow fibers with an automated process by mixing the back-filtered liquid with the air introduced via the lumen port of the dialyzer with the flow direction from the bottom to the top of the dialyzer. This gas-liquid mixture is made by passing the in-use cleaning solution at about 40° C. to about 55° C. through the membrane pore structure by backfiltration, while simultaneously introducing HEPA-filtered compressed air from the bottom blood Port 8. As the HEPA-filtered air mixes with the back-filtered liquid cleaning composition, at about 1:200 to 1:400 liquid-to-air ratio, a high velocity gas-liquid mixture flows through the hollow fibers of the dialyzer. This high-velocity gas-liquid flow generates sufficient shear stresses at the fiber lumens to remove clots and proteins from the dialyzer, and automatically cleans the headers at the same time. In this step, the back-filtered cleaning solution at about 40° C. to about 55° C. mixes with about 100 Liters at STP filtered air at 2.4 atmosphere gage pressure introduced to the dialyzer via the bottom blood Port 8 to create the gas-liquid mixture inside the fiber lumens. During this step, air is supplied at 1.7 atmosphere gage pressure to the top dialysate port of the dialyzer to keep the trans-membrane pressure (TMP) at below 0.8 atmosphere during cleaning, the limit recommended by dialyzer manufacturers. In this step, the gas-liquid mixture exits the dialyzer through the top blood Port 6 via the top header 2 (FIG. 13—[Step 3 of 6]). Opening and closing designated ports is automated with a programmed algorithm to control a set of solenoid valves.

Gas-Liquid Treatment Step 4: This is an automated step and is the same as Step (1) above and is designed to displace the air from the dialysate compartment of the dialyzer (FIG. 13—[Step 4 of 6]). Opening and closing designated ports is automated with a programmed algorithm to control a set of solenoid valves.

Gas-Liquid Treatment Step 5: This automated process is the same as Step (2) above and is designed to perform brief backfiltration and to fill both the dialysate and blood compartments of the dialyzer with the in-use cleaning composition at about 40° C. to about 55° C. (FIG. 13—[Step 5 of 6]). Opening and closing designated ports is automated with a programmed algorithm to control a set of solenoid valves.

Gas-Liquid Treatment Step 6: This is the gas-liquid flow cleaning step where the air-liquid mixture is formed as described above with the flow direction from the top blood Port 6 to the bottom blood Port 8 of the dialyzer. This is the same as Step (3), but with the flow direction reversed (FIG. 13—[Step 6 of 6]). Opening and closing designated ports is automated with a programmed algorithm to control a set of solenoid valves. Opening and closing designated ports is automated with a programmed algorithm to control a set of solenoid valves.

Steps 1 through 6 are repeated 5 to 10 times during the 5 to 7 minute gas-liquid treatment cycle. During the gas-liquid treatment cycle, the arterial and venous sides of the dialyzer receive equal cleaning by reversing the flow direction so that each side receives the same amount of treatment.

Automated Step 3: Rinsing the dialyzer with RO water at the ambient temperature is fully automated and is performed using the same flow sequence as the pre-cleaning cycle described in Automated Step 1, above. Opening and closing designated ports is automated with a programmed algorithm to control a set of solenoid valves.

Automated Step 4: The TCV measurement is an automated process and is performed by: a) filling both blood and dialysate compartments of the dialyzer with RO water and then closing Ports 6, 8, 18 and 20; b) displacing the water in the blood compartment by introduction air from Port 6 and collecting the water in a vessel via Port 8; c) determining the volume or weight of the water by an automated measuring instrument to determine the TCV of the dialyzer. Opening and closing designated ports is automated with a programmed algorithm to control a set of solenoid valves.

Automated Step 5: Testing the integrity of the blood compartment of the dialyzer automated by measuring pressure decay as a function of time, as follows: a) the blood compartment is pressurized with air and the pressured decay is measured with a sensitive pressure transducer as a function of time; b) the pressure data is analyzed to determine the presence or absence of fiber leaks according to a special algorithm. Opening and closing designated ports is automated with a programmed algorithm to control a set of solenoid valves.

Automated Step 6: The dialyzer is finally filled with the designated high-level disinfectant according an automated process as a follows: a) the desired concentration of the high-level disinfectant is made by mixing a disinfectant concentrate and RO water in a special vessel; b) the dialysate compartment of the dialyzer is filled with the disinfectant solution via Port 18 until it overflows from Port 20; c) the blood compartment is filled with the disinfectant solution via Port 8 until it overflows from Port 6; d) all ports of the dialyzer are capped. Opening and closing designated ports is automated with a programmed algorithm to control a set of solenoid valves.

The dialyzer is stored at ambient temperature for 15 hours before it can used to treat patients.

An embodiment pertains to a fully automated process for cleaning and processing dialysis membrane assemblies by the combination of the composition and treatment method according to the gas-liquid treatment sequence of steps described above. According to the present embodiment, the application of the automated process described above does not require any manual handling of the dialyzer in contrast to conventional dialyzer processing methods used in the industry such as those based on the peracetic acid method.

Terms used in the claims are intended to be interpreted, first, as would be understood by one of skill in the art; and then second if not definable as understood by one of skill in the art, according to a more general scientific dictionary used in the technical field; and then third if not definable according to the first and second interpretations according to a general dictionary. As used herein % or wt % refers to percent by weight of an ingredient as compared to the total weight of the composition or component that is being discussed. The unit "part per million" (PPM) has its ordinary meaning of one part of the component being discussed per million parts per weight of the mixture, i.e. 1 ppm=1×10-4%. The unit "part per billion" (PPB) has its ordinary meaning of one part of the component being discussed per billion parts per weight of the mixture, i.e. 1 ppb=1×10-7%.

Except in the operating and comparative examples, or where otherwise explicitly indicated, all numbers in this description indicating amounts of material or conditions of reaction, physical properties of materials and/or use are to be understood as modified by the word "about." All amounts are by weight of the final composition, unless otherwise specified.

For the avoidance of doubt the word "comprising" is intended to mean "including" but not necessarily "consisting of" or "composed of." In other words, the listed steps or options need not be exhaustive.

The terms composition, compositions, aqueous mixture, solution are all used to refer to the liquid used to clean dialysis membranes irrespective of the treatment method used. The term HOCl, free chlorine, available chlorine and hypochlorous acid are all intended to refer to the same chlorine based compound or species. Likewise hypochlorite refers to the hypochlorite salt (NaOCl) or to the ion —OCl or OCl—. The terms ORP, oxidation potential and oxidation-reduction potential all refer to the same measurement.

The terms membrane, dialyzer, hemodialyzer, dialysis membrane and dialysis membrane assembly or assemblies are all used interchangeably to refer to the device used to perform hemodialysis or other treatments such as hemodiafiltration, hemofiltration where the blood is handled with the aid or an extracorporeal circuit. What is meant by a membrane assembly having or employing PVP-containing membranes is that the membranes have PVP, PS, PES, polyamide or other polymers used as an integral component of the membrane itself. The numerous embodiments may comprise methods and/or compositions for cleaning a dialysis membrane having PVP, PS, PES, and/or polyamide and/or other polymers generally. For illustrative purposes only the Fresenius Optiflux® 200A dialyzer, Asahi APS® 21R dialyzer, and Gambro Polyflux® 21R dialyzer have been used to illustrate the effective cleaning of embodiments. The examples described below indicate that the cleaning composition and method embodiments may be applicable to dialysis membranes generically and need not be limited to specific manufacturer or type of membrane.

The present embodiment is drawn to novel compositions, methods, processes, delivery instruments and/or apparatus developed to improve cleaning and processing of dialysis filtration membranes and dialysis membrane assemblies. The present embodiment can provide improved methods for cleaning of dialysis filtration membranes without decrease in the membrane performance or function when it is reused to treat dialysis patients multiple times. The present embodiment can substantially improve the length of filter life and significantly increase number of times (number of reuses) a filter can be reused without degradation or loss of clearance functions of both small and middle molecules during dialysis treatment. Embodiments can include fully automating dialyzer processing and eliminated the need for manual handling during processing.

This disclosure is intended to explain how to fashion and use various embodiments in accordance with the invention rather than to limit the true, intended, and fair scope and spirit thereof. The invention is defined solely by the appended claims, as they may be amended during the pendency of this application for patent, and all equivalents thereof. The foregoing description is not intended to be exhaustive or to limit the invention to the precise form disclosed. Modifications or variations are possible in light of the above teachings. The embodiment(s) was chosen and described to provide the best illustration of the principles of the invention and its practical application, and to enable one of ordinary skill in the art to utilize the invention in various embodiments and with various modifications as are suited to the particular use contemplated. All such modifications and variations are within the scope of the invention as determined by the appended claims, as may be amended during the pendency of this application for patent, and all equivalents thereof, when interpreted in accordance with the breadth to which they are fairly, legally, and equitably entitled.

What is claimed is:

1. A method of cleaning a hemodialysis membrane assembly and removing protein from the pore structure of the membrane, the hemodialysis membrane assembly comprising inlet and outlet ports for a blood compartment, and inlet and outlet ports for a dialysate compartment wherein, in use, blood flows through a plurality of semi-permeable membrane hollow fibers of the blood compartment, each hollow fiber consisting of a lumen and a porous membrane wall, the method comprising:
   (a) applying a surfactant free composition to the hemodialysis membrane assembly for 5 to 10 minutes at a temperature of about 40° to about 55° C., the composition comprising:
      an inorganic base;
      from about 100 to about 1,000 ppm of a hypochlorite salt;
      between 0.4 ppb and 50 ppb free HOCl;
      a pH between at least 12.0 and about 12.8; and
      an oxidation-reduction potential greater than 0.376 volts but less than 0.5 volts; and
   (b) removing the composition from the hemodialysis membrane assembly with water.

2. The method of claim 1, wherein the hemodialysis membrane assembly comprises a polyvinylpyrrolidone (PVP)-containing membrane.

3. The method of claim 1, further comprising:
   (c) storing the hemodialysis membrane assembly in acid after step (b); and
   (d) removing the acid from the hemodialysis membrane assembly.

4. The method of claim 3, wherein peracetic acid solution is used to perform step (c).

5. The method of claim 1, wherein prior to step (a) the composition is in the form of a concentrate, and the method further comprises diluting the concentrate to the composition set forth in step (a).

6. The method of claim 5, wherein the step of diluting the concentrate composition is automated.

7. The method of claim 1, step (a) further comprises:
   pumping the composition under pressure through a dialysate compartment port and allowing the composition to exit the hemodialysis membrane assembly through the inlet and outlet ports of the blood compartment; wherein cleaning includes alternating cycles involving flow of the composition on the lumen side for a period of time followed by backfiltration through the membrane for another period of time and the composition is maintained simultaneously in contact with entire fiber surfaces of the hollow fibers of the hemodialysis membrane assembly, and the total time of membrane exposure to the cleaning composition does not exceed 10 minutes.

8. The method of claim 1, wherein the composition is applied to the hemodialysis membrane assembly in step (a) as a mixture of gas and the composition for 5 to 7 minutes and is provided to the assembly wherein the composition is delivered to the membrane by backfiltration from the dialysate compartment of the hemodialysis membrane assembly at a temperature of about 40° to about 55° C. and at volumetric flow rates between 100 and 600 ml/minute and the gas fraction comprises compressed air and is delivered through the lumens of the semi-permeable membrane hollow fibers at the ambient temperature and at volumetric flow rates between 56 to 150 liters per minute at STP.

9. The method of claim 1, wherein the hypochlorite salt is sodium hypochlorite, and the inorganic base is sodium hydroxide.

10. The method of claim 1, wherein the composition further comprises an additional salt that is a member selected from the group consisting of phosphates, benzoates, salicylates, citrates and mixtures thereof.

11. The method of claim 10, wherein the composition further comprises about 0.1% to about 0.5% by weight of sodium or potassium triphosphate.

12. The method of claim 10, wherein prior to step (a), the additional salt and the additional salt concentration is determined for a hemodialysis assembly model of the hemodialysis membrane assembly to be cleaned.

13. The method of claim 1, wherein the composition comprises: about 250 to about 1,000 ppm sodium hypochlorite; about 0.1 to about 0.5% sodium triphosphate and sodium hydroxide to provide a pH of about 12.2 to 12.5.

14. A surfactant free cleaning composition concentrate effective for cleaning polyvinylpyrrolidone (PVP)-containing dialysis membrane assemblies and removing protein from the pore structure of the membrane without erosion of PVP, said cleaning composition comprising:
    (a) from about 0.05% to about 4% by weight of a hypochlorite salt;
    (b) an alkali metal hydroxide to provide alkalinity;
    (c) the balance being water,
    wherein the cleaning composition is diluted prior to cleaning the PVP-containing dialysis membrane assemblies without substantial erosion of PVP to a diluted composition comprising:
    from about 100 to about 1,000 ppm of a hypochlorite salt,
    between 0.4 ppb and 50 ppb free HOCl,
    a pH of from at least pH 12.0 to about 12.8, and
    an oxidation-reduction potential greater than 0.376 volts but less than 0.5 volts,
    and
    a ratio of base:hypochlorite of at least 0.5.

15. The cleaning composition of claim 14 wherein the cleaning composition is provided in a 5×, 10×, 20×, 25×, 30×, 40× concentrate and the diluted composition is from about 100 ppm and about 1,000 ppm hypochlorite salt.

16. A composition of claim 14, wherein the composition further comprises 0.5% to about 20% by weight of an additional alkali metal salt of phosphate.

17. A composition of claim 14, wherein said alkali metal hydroxide is sodium hydroxide.

18. A composition of claim 14, wherein the hypochlorite salt is sodium hypochlorite.

19. The method of claim 1, wherein after cleaning steps (a) and (b), recovery of function of the hemodialysis membrane assembly is demonstrable by beta-2 microglobulin, urea, or cytochrome c measurement.

* * * * *